US010590406B2

(12) United States Patent
Koepke et al.

(10) Patent No.: US 10,590,406 B2
(45) Date of Patent: Mar. 17, 2020

(54) RECOMBINANT MICROORGANISMS EXHIBITING INCREASED FLUX THROUGH A FERMENTATION PATHWAY

(71) Applicant: LanzaTech New Zealand Limited, Skokie, IL (US)

(72) Inventors: Michael Koepke, Skokie, IL (US); Alexander Paul Mueller, Skokie, IL (US); Loan Phuong Tran, Skokie, IL (US)

(73) Assignee: LANZATECH NEW ZEALAND LIMITED, Skokie, IL (US)

( * ) Notice: Subject to any disclaimer, the term of this patent is extended or adjusted under 35 U.S.C. 154(b) by 0 days.

(21) Appl. No.: 14/961,146

(22) Filed: Dec. 7, 2015

(65) Prior Publication Data

US 2016/0160223 A1 Jun. 9, 2016

Related U.S. Application Data

(60) Provisional application No. 62/168,969, filed on Jun. 1, 2015, provisional application No. 62/089,053, filed on Dec. 8, 2014.

(51) Int. Cl.
| | |
|---|---|
| *C12P 7/18* | (2006.01) |
| *C12N 9/88* | (2006.01) |
| *C12N 9/02* | (2006.01) |
| *C12N 9/04* | (2006.01) |
| *C12N 1/21* | (2006.01) |
| *C12N 15/52* | (2006.01) |
| *C12N 15/53* | (2006.01) |
| *C12N 9/10* | (2006.01) |

(52) U.S. Cl.
CPC ............ *C12N 9/88* (2013.01); *C12N 9/0008* (2013.01); *C12N 9/1022* (2013.01); *C12N 15/52* (2013.01); *C12P 7/18* (2013.01); *C12Y 102/07001* (2013.01); *C12Y 202/01006* (2013.01); *C12Y 401/01005* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,173,429 A | 12/1992 | Gaddy et al. | |
| 5,593,886 A | 1/1997 | Gaddy | |
| 6,368,819 B1 | 4/2002 | Gaddy et al. | |
| 8,143,037 B2 | 3/2012 | Zahn et al. | |
| 10,174,303 B2* | 1/2019 | Behrendorff | C12P 1/04 |
| 2007/0259410 A1* | 11/2007 | Donaldson | C12N 9/0006 |
| | | | 435/148 |
| 2009/0203097 A1 | 8/2009 | Flint et al. | |
| 2011/0129904 A1* | 6/2011 | Burgard | C12N 15/52 |
| | | | 435/252.33 |
| 2011/0229947 A1 | 9/2011 | Zahn et al. | |
| 2012/0252083 A1* | 10/2012 | Koepke | C12P 7/04 |
| | | | 435/150 |
| 2013/0210090 A1 | 8/2013 | Pearlman et al. | |
| 2014/0256008 A1 | 9/2014 | Boisart, Sr. et al. | |
| 2015/0093796 A1 | 4/2015 | Ying | |
| 2018/0142265 A1* | 5/2018 | Chen | C12N 15/74 |

FOREIGN PATENT DOCUMENTS

| | | | |
|---|---|---|---|
| CN | 103320335 A | 9/2013 | |
| CN | 103436479 A | 12/2013 | |
| WO | 2002/008438 | 1/2002 | |
| WO | WO-2007130518 A2 * | 11/2007 | ........... C12N 9/0006 |
| WO | 2008/028055 | 6/2008 | |
| WO | 2009/064200 | 5/2009 | |
| WO | 2010063766 A1 | 6/2010 | |
| WO | WO-2012033832 A2 * | 3/2012 | ........... C12N 9/0006 |
| WO | 2012/053905 | 4/2012 | |
| WO | 2012/115527 | 4/2012 | |
| WO | WO-2013115659 A2 * | 8/2013 | ............... C12N 1/20 |
| WO | WO 2014052920 A2 * | 4/2014 | ..... C12Y 401/01005 |
| WO | 2014197746 A1 | 12/2014 | |
| WO | 2015042550 A1 | 3/2015 | |
| WO | 2017015642 A1 | 1/2017 | |

OTHER PUBLICATIONS

Kopke et al., 2,3-Butanediol Production by Acetogenic Bacteria, an Alternative Route to Chemical Synthesis, Using Industrial Waste Gas, Appl. Environ. Microbiol., 2011, 77, 5467-75.*
Tyurin et al., Synthetic 2,3-Butanediol Pathway Integrated Using Tn7-tool and Powered Via Elimination of Sporulation and Acetate Production in Acetogen Biocatalyst, Appl. Biochem. Biotechnol., May 2013, 170, 1502-24.*
Nagaraju et al., Identification of acetogenic 2,3butanediol and lactate production pathways and reconstruction in metabolically engineered E. coli, SIMB Annual Meeting & Exhibition, Aug. 2012, Washington, DC, Poster Session 1 Abstract P177.*
Ueki et al., Converting carbon dioxide to butyrate with an engineered strain of Clostridium ljungdahlii, mBio, Oct. 2014, 5, e01646-14.*

(Continued)

*Primary Examiner* — Robert B Mondesi
*Assistant Examiner* — Todd M Epstein
(74) *Attorney, Agent, or Firm* — Andrea Schoen

(57) ABSTRACT

The invention provides a recombinant, carboxydotrophic *Clostridium* bacterium that expresses one or more of pyruvate:ferredoxin oxidoreductase (EC 1.2.7.1), acetolactate synthase (EC 2.2.1.6), and acetolactate decarboxylase (EC 4.1.1.5). The invention further provides a method of producing a fermentation product by fermenting the recombinant bacterium in the presence of a gaseous substrate comprising CO to produce one or more of ethanol, butanol, isopropanol, isobutanol, higher alcohols, butanediol, 2,3-butanediol, succinate, isoprenoids, fatty acids, biopolymers, and mixtures thereof.

16 Claims, 8 Drawing Sheets
Specification includes a Sequence Listing.

(56) References Cited

OTHER PUBLICATIONS

Lagoa-Costa et al. ("Integrated bioconversion of syngas into bioethanol and biopolymers," Bioresource Tech., 2017, 239, 244-49.*
Humphreys et al., Advances in metabolic engineering in the microbial production of fuels and chemicals from C1 gas, Curr. Opinion Biotechnol., 2018, 50, 174-81.*
Liew et al., Gas Fermentation for Commercial Biofuels Production, Chapter 5 in Gas Fermentation for Commercial Biofuel Production, 2013.*
Breitkopf, Understanding the C4 dicarboxylic acid metabolism in Clostridium autoethanogenum, Dissertation, University of Nottingham, 2018, Abstract Only.*
Mendel et al., Acetohydroxyacid Synthase: A Proposed Structure for Regulatory Subunits Supported by Evidence from Mutagenesis , J. Mol. Biol., 2001, 307, 465-77.*
Japanese Office Action for Japanese Patent Application 2017-549170, Japanese Intellectual Property Office, English translation only, dated Oct. 8, 2019.*
International Search Report for International Patent Application No. PCT/US2015/064351, Korean Intellectual Property Office, dated Mar. 31, 2016.
Abrini, *Clostridium autoethanogenum*, sp. nov., an anaerobic bacterium that produces ethanol from carbon monoxide, Arch Microbiol, 161: 345-351, 1994.
Abubackar, Biological conversion of carbon monoxide to ethanol: Effect of pH, gas pressure, reducing agent and yeast extract, Bioresour Technol, 114: 518-522, 2012.
Collins, The phylogeny of the genus *Clostridium*: proposal of five new genera and eleven new species combinations, Int J System Bacteriol, 44; 812-826, 1994.
Furdi, The role of pyruvate ferredoxin oxidoreductase in pyruvate synthesis during autotrophic growth by the Wood-Ljungdahl pathway, J Biol Chem, 15: 28494-28499, 2000.
Heap, A modular system for Clostridium shuttle plasmids, J Microbiol Meth, 78: 79-85, 2009.
Hensirisak, Scale-up of microbubble dispersion generator for aerobic fermentation, Appl Biochem Biotechnol, 101: 211-227, 2002.
Herbert, Gene transfer into Clostridium difficile CD630 and characterisation of its methylase genes, FEMS Microbiol Lett, 229: 103-110, 2003.
Huang, Electron bifurcation involved in the energy metabolism of the acetogenic bacterium *Moorella thermoacetica* growing on glucose or H2 plus CO2, J Bacteriol, 194: 3689-3699, 2012.
International Search Report for International Patent Application PCT/US2014/041188, Korean Intellectual Property Office, dated Sep. 22, 2014.
Jennert, Gene transfer to Clostridium cellulolyticum ATCC 35319, Microbiol, 146: 3071-3080, 2000.
Kita, Development of genetic transformation and heterologous expression system in carboxydotrophic thermophilic acetogen *Moorella thermoacetica*, J Biosci Bioeng, 115: 347-352, 2013.
Köpke, 2,3-Butanediol production by acetogenic bacteria, an alternative route to chemical synthesis, using industrial waste gas, Appl Envrion Microbiol, 77: 5467-5475, 2011.
Köpke, Clostridium ljungdahlii represents a microbial production platform based on syngas, PNAS USA, 107: 13087-13092, 2010.
Köpke, Fermentative production of ethanol from carbon monoxide, Curr Opin Biotechnol, 22: 320-325, 2011.
Leang, Development of genetic systems for Clostridium ljungdahlii, 2011.
Mermelstein, Expression of cloned homologous fermentative genes in Clostridium acetobutylicum ATCC 824, Nat Biotechnol, 10: 190-195, 1992.
Murray, Type I restriction systems: sophisticated molecular machines (a legacy of Bertani and Weigle), Microbial Molec Biol Rev, 64: 412-434, 2000.
Ng, Production of 2,3-butanediol in *Saccharomyces cerevisiae* by in silico aided metabolic engineering, Microb Cell Factories, 11: 68, 2012.
Oliver, Combinatorial optimization of cyanobacterial 2,3-butanediol production, Metabol Eng, 22: 76-82, 2014.
Oliver, Cyanobacterial conversion of carbon dioxide to 2,3-butanediol, PNAS, 110: 1249-1254, 2013.
Parthasarathy, Development of a genetic modification system in Clostridium scatologenes ATCC 25775 for generation of mutants, Masters Project, Western Kentucky University, 2010.
Perez, Biocatalytic reduction of short chain carboxylic acids, Biotechnol Bioeng, 1-30, 2012.
Pieulle, Isolation and analysis of the gene encoding the pyruvate-ferredoxin oxidoreductase of Desulfovibrio africanus, production of the recombinant enzyme in *Escherichia coli*, and effect of carboxy-terminal deletions on its stability, J Bacteriol, 179: 5684-5692, 1997.
Schiel-Bengelsdorf, Pathway engineering and synthetic biology using acetogens, Synthetic Biol, 15: 2191-2198, 2012.
Strätz, Plasmid transfer into the homoacetogen *Acetobacterium woodii* by electroporation and conjugation, Appl Environ Microbiol, 60: 1033-1037, 1994.
Tanner, *Clostridium ljungdahlii* sp. nov., an acetogenic species in Clostridial rRNA homology group I, Int J System Bacteriol, 43: 232-236, 1993.
Tirado-Acevedo, Production of bioethanol from synthesis gas using Clostridium ljungdahlii, PhD thesis, North Carolina State University, 2010.
Tyurin, Electrofusion of cells of acetogen *Clostridium* sp. MT 351 with erm(B) or cat in the chromosome, J Biotech Res, 4: 1-12, 2012.
Tyurin, Electrotransformation of Clostridium thermocellum, Appl Environ Microbiol, 70: 883-890, 2004.
Williams, Conjugative plasmid transfer from *Escherichia coli* to Clostridium acetobutylicum, J Gen Microbiol, 136: 819-826, 1990.
Dürre, Handbook on Clostridia, CRC Press, pp. 813-814, 2005.
Bertsch, Biotechnol Biofuels, 8: 210, 2015.
Bengelsdorf, Environ Technol, 34: 1639-1651, 2013.
Durre, Curr Opin Biotechnol, 35: 63-72, 2015.
Durre, FEMS Microbiol Lett, 363, 2016.
Latif, Curr Opin Biotechnol, 27: 79-87, 2014.
Martin, Comparing Ethanol Production of Carboxydotrophic Clostridium Strains During Syngas Fermentation with a Two-State Continuous Culture, Thesis, Cornell University, 2014.
Syngas Biofuels Energy, Inc., www.syngasbiofuelsenergy.com, accessed Jan. 25, 2018.

* cited by examiner

SEQUENCE LISTING

<160> NUMBER OF SEQ ID NOS: 28

<210> SEQ ID NO 1
<211> LENGTH: 3513
<212> TYPE: DNA
<213> ORGANISM: Clostridium autoethanogenum LZ1561

<400> SEQUENCE: 1

```
atgcgtaaaa tgaaaactat ggatggaaat actgctgctg cttatatttc ctatgcattt        60
actgatgtag cagctattta tccaataact ccatcatcac caatggcaga acatgtagat       120
gaatgggtag ctaagggaaa gaaaaatatt tttggacaac aagtaaaagt tatggagatg       180
caatcagagg ctggagcatc aggagccgta catggttcac tacaagcagg agcattgact       240
agtacatata ctgcatctca aggcttatta cttatgatac ctaacatgta taagattgct       300
ggtgaattat taccaggagt attccatgta tcagctagag cagtagctgc aaattcactt       360
aacatatttg gtgatcacca agatgttatg gcaacaagac aaactggatt tgctttattt       420
gcagaaagtt cagtacaaca ggttatggat ctttcagcag tagcccattt atcagcaata       480
```

```
aaaggaagag ttccatttgt aaacttcttt gatggattca gaacttctca tgaaattcaa      540
aaaatcgaat tattagagta tgaagaatta gcaaaattag ttgatcagaa agctttgaat      600
gattttagaa gaagagcttt aaatccagat catccagtaa ctcgtggtac agctcaaaat     660
cctgatatat acttccagga aagagaagtt tcaaatacgt attacgaagc acttccagag     720
atagttgaag gatatatgca agaaatgact aaacttacag gaagagaata tcatctattc     780
aattactatg gagcaaaaga tgcagagaga attataatag ctatgggttc tgtctgtgaa     840
actgtagaag aagtaattga ttacttaacc acaaaaggtg aaaaagttgg attacttaca     900
gttcatttat atagaccatt ctcaataaaa cactttatga aatacatacc aaagactgtt     960
aagaaaattg cagtccttga tagaacaaaa gaaccaggat caattggaga acctctttat    1020
ttagatgtta agaatgcttt ctatggacaa gaagtacaac cagttatagt tggtggaaga    1080
tatggacttg gttcaaaaga tgtattacca tcacatattc taccagtatt tgaaaactta    1140
aaatcagata aacctaagga tagatttaca ttaagtatag ttgatgatgt tacaaatact    1200
tcattacctg taggagaaga tataaataca acaccagaag gaactacagc ttgtaagttc    1260
tggggactag gatcagatgg tactgttgga gcaaacaaga gtgctataaa gatcattgga    1320
gaccatacag atatgtatgc tcaaggatac tttgcatatg attcaaagaa atccggtggt    1380
ataacagttt ctcatttaag atttggtaaa tcaccaataa aatcaccata tcttatagat    1440
aaggctgatt ttgttgcagt tcataaccaa tcttatgttc ataagtatga tgtacttgca    1500
ggacttaaaa aaggcggtaa cttcttatta aatacagttt ggactcaaga agaattggaa    1560
aaagagttac cagcttctat gaagaaatat atagcaaaca atgatataaa attctataca    1620
ttaaatgctg ttaaaatagc tcaagaaatt ggacttggtg gaagaataaa tatgatatgt    1680
caatcagcat tctttaagat tgcaaatatc attccaatag atgatgctgt taagtactta    1740
aaagaagcag ttgtaacttc ttatggtaag aagggacaaa aagttgtaga tatgaataac    1800
gctgctatag acaagggcgt aaatgcagta gttaaaatag atgttccagc ttcatggaaa    1860
gatgcagaag atgaagcagc agctacaaag gaacttccta aatttataga aaaaatagtt    1920
aatcctatga atagacaaga aggagacaaa cttccagtaa gtgcatttgt aggaatggaa    1980
gatggtacat tcccagcagg aactgcagct tatgaaaaga gaggaatagc tataaatgtt    2040
ccagaatggc aagtagacaa atgtatacaa tgtaaccaat gttcatttgt atgtccacat    2100
gcagctataa gaccagttct tacaactgaa gaagaattag ctaaagcacc tcaaggattt    2160
gaagctaaag atgcaaatgg agcaaaagga cttaaattta caatggctat ttcaccactt    2220
gattgttcag gatgtggaaa ctgtgaagat gtatgtccag caaagaaaaa ggctcttgtt    2280
atgaagccag tagatactca gctgtcaaag acagaagctt gggattatgc tgttaatgct    2340
gtagctcata aggataaccc aatgaaggac aaatacagtg taaaagcaag tcagttcgaa    2400
caaccattac ttgagttctc aggagcttgt gcaggatgcg gagaaactcc ttatgttaaa    2460
cttgtaactc aattgtttgg tgatagaatg atgatagcaa atgctacagg atgttcatca    2520
atttggggag catcagcacc agcaactcca tacacaacta actatagagg acatggtcca    2580
tcttgggcta actcattatt tgaagacaat gctgaatatg gattaggtat gttccttgga    2640
gttaaacaga caagagaaag acttcaggat aaaattgaag aagctttaaa gggtagttta    2700
agtgcagaac ttaaagctgc ttttgaagac tggattaaaa actttgctga aggtgaagga    2760
acaagagaaa gagctgataa aataacagct ttacttgaaa aagaaaaggg aagcaatgat    2820
ttattaaatg atatttatga aaacagagac ttcctagtaa agagatccca ctggataatt    2880
```

```
ggtggagacg ttgggggcta tgatattgga tatggtggag tagatcatgt tttagcttca   2940
aatgaagatg taaatattct tgtacttgat acagaagtat attcaaatac aggtggacaa   3000
tcttcaaaat caactccaac agctgctgta gctaaatttg ctgcaagtgg taagaagact   3060
aagaagaaag atcttggaat gatggctatg agttatggat atgtttatgt agctcagatt   3120
tcaatgggtg ctgataagaa tcaggcatta aaggcaattc atgaagcaga agcttatcat   3180
ggaccatcac ttataatagc ttatgctcca tgtatcaatc atggcttaag agttggaatg   3240
ggtaagagcc agagagaagc taagagagct gttgattgtg gatattgggc actttacaga   3300
tacaatccag aattaaaaga agaaggaaag aaatcattta gcttggattc aaaagaacca   3360
actacagatt tcaaggaatt cttaatggga gaagtaagat actcttcact tgctaaacaa   3420
ttcccagatc aggcagatgc attatttgaa aagactaaga agatgctctc tcaaagaatt   3480
gcaggatata aaaagcttga taatgaacag taa                                3513
```

<210> SEQ ID NO 2
<211> LENGTH: 1170
<212> TYPE: PRT
<213> ORGANISM: Clostridium autoethanogenum LZ1561

<400> SEQUENCE: 2

```
Met Arg Lys Met Lys Thr Met Asp Gly Asn Thr Ala Ala Ala Tyr Ile
1               5                   10                  15

Ser Tyr Ala Phe Thr Asp Val Ala Ala Ile Tyr Pro Ile Thr Pro Ser
            20                  25                  30

Ser Pro Met Ala Glu His Val Asp Glu Trp Val Ala Lys Gly Lys Lys
        35                  40                  45

Asn Ile Phe Gly Gln Gln Val Lys Val Met Glu Met Gln Ser Glu Ala
    50                  55                  60

Gly Ala Ser Gly Ala Val His Gly Ser Leu Gln Ala Gly Ala Leu Thr
65                  70                  75                  80

Ser Thr Tyr Thr Ala Ser Gln Gly Leu Leu Leu Met Ile Pro Asn Met
                85                  90                  95

Tyr Lys Ile Ala Gly Glu Leu Leu Pro Gly Val Phe His Val Ser Ala
            100                 105                 110

Arg Ala Val Ala Ala Asn Ser Leu Asn Ile Phe Gly Asp His Gln Asp
        115                 120                 125

Val Met Ala Thr Arg Gln Thr Gly Phe Ala Leu Phe Ala Glu Ser Ser
    130                 135                 140

Val Gln Gln Val Met Asp Leu Ser Ala Val Ala His Leu Ser Ala Ile
145                 150                 155                 160

Lys Gly Arg Val Pro Phe Val Asn Phe Phe Asp Gly Phe Arg Thr Ser
                165                 170                 175

His Glu Ile Gln Lys Ile Glu Leu Leu Glu Tyr Glu Glu Leu Ala Lys
            180                 185                 190

Leu Val Asp Gln Lys Ala Leu Asn Asp Phe Arg Arg Ala Leu Asn
        195                 200                 205

Pro Asp His Pro Val Thr Arg Gly Thr Ala Gln Asn Pro Asp Ile Tyr
    210                 215                 220

Phe Gln Glu Arg Glu Val Ser Asn Thr Tyr Tyr Glu Ala Leu Pro Glu
225                 230                 235                 240

Ile Val Glu Gly Tyr Met Gln Glu Met Thr Lys Leu Thr Gly Arg Glu
                245                 250                 255
```

Tyr His Leu Phe Asn Tyr Tyr Gly Ala Lys Asp Ala Glu Arg Ile Ile
            260                 265                 270

Ile Ala Met Gly Ser Val Cys Glu Thr Val Glu Val Ile Asp Tyr
        275                 280                 285

Leu Thr Thr Lys Gly Glu Lys Val Gly Leu Leu Thr Val His Leu Tyr
        290                 295                 300

Arg Pro Phe Ser Ile Lys His Phe Met Lys Tyr Ile Pro Lys Thr Val
305                 310                 315                 320

Lys Lys Ile Ala Val Leu Asp Arg Thr Lys Glu Pro Gly Ser Ile Gly
                325                 330                 335

Glu Pro Leu Tyr Leu Asp Val Lys Asn Ala Phe Tyr Gly Gln Glu Val
                340                 345                 350

Gln Pro Val Ile Val Gly Gly Arg Tyr Gly Leu Gly Ser Lys Asp Val
                355                 360                 365

Leu Pro Ser His Ile Leu Pro Val Phe Glu Asn Leu Lys Ser Asp Lys
                370                 375                 380

Pro Lys Asp Arg Phe Thr Leu Ser Ile Val Asp Val Thr Asn Thr
385                 390                 395                 400

Ser Leu Pro Val Gly Glu Asp Ile Asn Thr Thr Pro Glu Gly Thr Thr
                405                 410                 415

Ala Cys Lys Phe Trp Gly Leu Gly Ser Asp Gly Thr Val Gly Ala Asn
                420                 425                 430

Lys Ser Ala Ile Lys Ile Ile Gly Asp His Thr Asp Met Tyr Ala Gln
                435                 440                 445

Gly Tyr Phe Ala Tyr Asp Ser Lys Lys Ser Gly Gly Ile Thr Val Ser
        450                 455                 460

His Leu Arg Phe Gly Lys Ser Pro Ile Lys Ser Pro Tyr Leu Ile Asp
465                 470                 475                 480

Lys Ala Asp Phe Val Ala Val His Asn Gln Ser Tyr Val His Lys Tyr
                485                 490                 495

Asp Val Leu Ala Gly Leu Lys Lys Gly Gly Asn Phe Leu Leu Asn Thr
                500                 505                 510

Val Trp Thr Gln Glu Glu Leu Glu Lys Glu Leu Pro Ala Ser Met Lys
        515                 520                 525

Lys Tyr Ile Ala Asn Asn Asp Ile Lys Phe Tyr Thr Leu Asn Ala Val
        530                 535                 540

Lys Ile Ala Gln Glu Ile Gly Leu Gly Gly Arg Ile Asn Met Ile Cys
545                 550                 555                 560

Gln Ser Ala Phe Phe Lys Ile Ala Asn Ile Ile Pro Ile Asp Asp Ala
                565                 570                 575

Val Lys Tyr Leu Lys Glu Ala Val Val Thr Ser Tyr Gly Lys Lys Gly
                580                 585                 590

Gln Lys Val Val Asp Met Asn Asn Ala Ala Ile Asp Lys Gly Val Asn
                595                 600                 605

Ala Val Val Lys Ile Asp Val Pro Ala Ser Trp Lys Asp Ala Glu Asp
        610                 615                 620

Glu Ala Ala Ala Thr Lys Glu Leu Pro Lys Phe Ile Glu Lys Ile Val
625                 630                 635                 640

Asn Pro Met Asn Arg Gln Glu Gly Asp Lys Leu Pro Val Ser Ala Phe
                645                 650                 655

Val Gly Met Glu Asp Gly Thr Phe Pro Ala Gly Thr Ala Ala Tyr Glu
        660                 665                 670

Lys Arg Gly Ile Ala Ile Asn Val Pro Glu Trp Gln Val Asp Lys Cys

```
              675                 680                 685
Ile Gln Cys Asn Gln Cys Ser Phe Val Cys Pro His Ala Ala Ile Arg
    690                 695                 700
Pro Val Leu Thr Thr Glu Glu Leu Ala Lys Ala Pro Gln Gly Phe
705                 710                 715                 720
Glu Ala Lys Asp Ala Asn Gly Ala Lys Gly Leu Lys Phe Thr Met Ala
                725                 730                 735
Ile Ser Pro Leu Asp Cys Ser Gly Cys Gly Asn Cys Glu Asp Val Cys
                740                 745                 750
Pro Ala Lys Glu Lys Ala Leu Val Met Lys Pro Val Asp Thr Gln Leu
                755                 760                 765
Ser Lys Thr Glu Ala Trp Asp Tyr Ala Val Asn Ala Val Ala His Lys
    770                 775                 780
Asp Asn Pro Met Lys Asp Lys Tyr Ser Val Lys Ala Ser Gln Phe Glu
785                 790                 795                 800
Gln Pro Leu Leu Glu Phe Ser Gly Ala Cys Ala Gly Cys Gly Glu Thr
                805                 810                 815
Pro Tyr Val Lys Leu Val Thr Gln Leu Phe Gly Asp Arg Met Met Ile
                820                 825                 830
Ala Asn Ala Thr Gly Cys Ser Ser Ile Trp Gly Ala Ser Ala Pro Ala
    835                 840                 845
Thr Pro Tyr Thr Thr Asn Tyr Arg Gly His Gly Pro Ser Trp Ala Asn
    850                 855                 860
Ser Leu Phe Glu Asp Asn Ala Glu Tyr Gly Leu Gly Met Phe Leu Gly
865                 870                 875                 880
Val Lys Gln Thr Arg Glu Arg Leu Gln Asp Lys Ile Glu Glu Ala Leu
                885                 890                 895
Lys Gly Ser Leu Ser Ala Glu Leu Lys Ala Ala Phe Glu Asp Trp Ile
                900                 905                 910
Lys Asn Phe Ala Glu Gly Glu Gly Thr Arg Glu Arg Ala Asp Lys Ile
                915                 920                 925
Thr Ala Leu Leu Glu Lys Glu Lys Gly Ser Asn Asp Leu Leu Asn Asp
    930                 935                 940
Ile Tyr Glu Asn Arg Asp Phe Leu Val Lys Arg Ser His Trp Ile Ile
945                 950                 955                 960
Gly Gly Asp Gly Trp Gly Tyr Asp Ile Gly Tyr Gly Gly Val Asp His
                965                 970                 975
Val Leu Ala Ser Asn Glu Asp Val Asn Ile Leu Val Leu Asp Thr Glu
                980                 985                 990
Val Tyr Ser Asn Thr Gly Gly Gln Ser Ser Lys Ser Thr Pro Thr Ala
    995                 1000                1005
Ala Val Ala Lys Phe Ala Ala Ser Gly Lys Lys Thr Lys Lys Lys
    1010                1015                1020
Asp Leu Gly Met Met Ala Met Ser Tyr Gly Tyr Val Tyr Val Ala
    1025                1030                1035
Gln Ile Ser Met Gly Ala Asp Lys Asn Gln Ala Leu Lys Ala Ile
    1040                1045                1050
His Glu Ala Glu Ala Tyr His Gly Pro Ser Leu Ile Ile Ala Tyr
    1055                1060                1065
Ala Pro Cys Ile Asn His Gly Leu Arg Val Gly Met Gly Lys Ser
    1070                1075                1080
Gln Arg Glu Ala Lys Arg Ala Val Asp Cys Gly Tyr Trp Ala Leu
    1085                1090                1095
```

| | | | | | | | | | | |
|---|---|---|---|---|---|---|---|---|---|---|
| Tyr | Arg | Tyr | Asn | Pro | Glu | Leu | Lys | Glu | Glu | Gly | Lys | Lys | Ser | Phe |
| 1100 | | | | 1105 | | | | | 1110 | | | | | |

Ser Leu Asp Ser Lys Glu Pro Thr Thr Asp Phe Lys Glu Phe Leu
     1115                1120                1125

Met Gly Glu Val Arg Tyr Ser Ser Leu Ala Lys Gln Phe Pro Asp
1130                1135                1140

Gln Ala Asp Ala Leu Phe Glu Lys Thr Lys Asp Ala Leu Gln
    1145                1150                1155

Arg Ile Ala Gly Tyr Lys Lys Leu Asp Asn Glu Gln
1160                1165                1170

<210> SEQ ID NO 3
<211> LENGTH: 3538
<212> TYPE: DNA
<213> ORGANISM: Artificial sequence
<220> FEATURE:
<223> OTHER INFORMATION: Codon-optimized Clostridium autoethanogenum
      LZ1561 pyruvate:ferredoxin oxidoreductase

<400> SEQUENCE: 3

```
tctagaagga ggtaactaaa tgagaaaaat gaaaactatg gatggaaata ctgcagcagc     60
atatataagt tatgcattta ctgatgtagc agcaatatat cctataactc ctagtagtcc    120
tatggcagaa catgtagatg aatgggtagc aaaaggaaaa aaaatatat ttggacaaca    180
agtaaaagta atggaaatgc aaagtgaagc tggagcaagt ggagcagtac atggaagttt    240
acaagctgga gcattaacta gtacttatac tgcaagtcaa ggattattat taatgatacc    300
taatatgtat aaaatagctg gagaattatt acctggagta tttcatgtaa gtgcaagagc    360
agtagcagca atagtttaa atatatttgg agatcatcaa gatgtaatgg caactagaca    420
aactggattt gcattatttg cagaaagtag tgtacaacaa gtaatggatt taagtgcagt    480
agcacattta gtgcaataa aaggaagagt accttttgta aattttttg atggatttag    540
aactagtcat gaaatacaaa aatagaatt attagaatat gaagaattag caaaattagt    600
agatcaaaaa gcattaaatg atttagaag aagagcatta aatcctgatc atcctgtaac    660
tagaggaact gcacaaaatc ctgatatata ttttcaagaa agagaagtaa gtaatactta    720
ttatgaagca ttacctgaaa tagtagaagg atatatgcaa gaaatgacta aattaactgg    780
aagagaatat catttattta ttattattgg agcaaaagat gcagaaagaa taataatagc    840
aatgggaagt gtatgtgaaa ctgtagaaga agtaatagat tatttaacta ctaaaggaga    900
aaaagtagga ttattaactg tacatttata tagaccttt agtataaaac attttatgaa    960
atatatacct aaaactgtaa aaaaatagc agtattagat agaactaaag aacctggaag   1020
tataggagaa cctttatatt tagatgtaaa aaatgctttt tatggacaag aagtacaacc   1080
tgtaatagtt ggaggaagat atggattagg atctaaagat gtattaccta gtcatatatt   1140
acctgtattt gaaaatttaa aaagtgataa acctaaagat agatttactt taagtatagt   1200
agatgatgta actaatacta gtttacctgt tggagaagat ataaatacta ctcctgaagg   1260
aactactgca tgtaaatttt ggggattagg aagtgatgga actgttggag caaataaatc   1320
tgcaataaaa ataataggag atcatactga tatgtatgca caaggatatt ttgcttatga   1380
tagtaaaaaa agtggaggaa taactgtaag tcatttaaga tttggaaaaa gtcctataaa   1440
aagtccttat ttaatagata aagcagattt tgtagcagta cataatcaaa gttatgttca   1500
taaatatgat gtattagcag gattaaaaaa aggaggaaat ttttattaa atactgtatg   1560
```

| | | |
|---|---|---|
| gactcaagaa gaattagaaa aagaattacc tgcaagtatg aaaaagtata tagcaaataa | 1620 | |
| tgatataaag ttttatactt taaatgcagt aaaaatagca caagaaatag gattaggagg | 1680 | |
| aagaataaat atgatatgtc aaagtgcatt ttttaaaata gcaaatataa tacctataga | 1740 | |
| tgatgcagta aaatatttaa aagaagcagt agtaactagt tatggaaaaa aaggacaaaa | 1800 | |
| agttgtagat atgaataatg cagcaataga taaaggagta aatgcagtag taaaaataga | 1860 | |
| tgtacctgca agttggaaag atgctgaaga tgaagcagca gcaactaaag aattacctaa | 1920 | |
| atttatagaa aaaatagtaa atcctatgaa tagacaagaa ggagataaat tacctgtaag | 1980 | |
| tgcatttgta ggaatggaag atggaacttt tcctgctgga actgcagctt atgaaaaaag | 2040 | |
| aggaatagca ataaatgtac ctgaatggca agtagataaa tgtatacaat gtaatcaatg | 2100 | |
| tagttttgta tgtcctcatg cagcaataag acctgtatta actactgaag aagaattagc | 2160 | |
| taaagcacct caaggatttg aagctaaaga tgcaaatgga gctaaaggat taaaatttac | 2220 | |
| tatggcaata agtcctttag attgtagtgg atgtggaaat tgtgaagatg tatgtcctgc | 2280 | |
| aaaagaaaaa gcattagtaa tgaaacctgt agatactcaa ttaagtaaaa ctgaagcatg | 2340 | |
| ggattatgca gtaaatgctg tagcacataa agataatcct atgaaagata aatatagtgt | 2400 | |
| aaaagcaagt caatttgaac aacctttatt agaatttagt ggagcatgtg caggatgtgg | 2460 | |
| agaaactcct tatgtaaaat tagtaactca attatttgga gatagaatga tgatagcaaa | 2520 | |
| tgcaactgga tgtagtagta tatggggagc aagtgctcct gcaactcctt atactactaa | 2580 | |
| ttatagagga catggaccta gttgggcaaa ttctttattt gaagataatg cagaatatgg | 2640 | |
| attaggaatg ttttttaggag taaaacaaac tagagaaaga ttacaagata aaatagaaga | 2700 | |
| agcattaaaa ggatctttaa gtgcagaatt aaaagcagca tttgaagatt ggataaaaaa | 2760 | |
| ttttgcagaa ggagaaggaa caagagaaag agcagataaa ataactgcat tattagaaaa | 2820 | |
| agaaaaagga tctaatgatt tattaaatga tatatatgaa aatagagatt ttttagtaaa | 2880 | |
| aagaagtcat tggataatag gaggagtgg atgggatat gatataggat atggaggagt | 2940 | |
| agatcatgta ttagcaagta atgaagatgt aaatatatta gtattagata ctgaagtata | 3000 | |
| tagtaatact ggaggacaaa gtagtaaaag tactcctact gcagcagtag caaaatttgc | 3060 | |
| agcaagtgga aaaaaaacta aaaaaaaaga tttaggaatg atggcaatga gttatggata | 3120 | |
| tgtatatgta gcacaaataa gtatgggagc tgataaaaat caagctttaa aagcaataca | 3180 | |
| tgaagctgaa gcatatcatg gaccaagttt aataatagct tatgcacctt gtataaatca | 3240 | |
| tggattaaga gtaggaatgg gaaaaagtca aagagaagca aaaagagcag tagattgtgg | 3300 | |
| atattgggca ttatatagat ataatcctga attaaaagaa gaaggaaaaa aatcttttag | 3360 | |
| tttagatagt aaagaaccta ctactgattt taaagaattt ttaatgggag aagtaagata | 3420 | |
| tagtagttta gcaaaacaat ttcctgatca agcagatgct ttatttgaaa aaacaaaaaa | 3480 | |
| agatgcatta caaagaatag ctggatataa aaaattagat aatgaacaat aagctagc | 3538 | |

<210> SEQ ID NO 4
<211> LENGTH: 1170
<212> TYPE: PRT
<213> ORGANISM: Artificial sequence
<220> FEATURE:
<223> OTHER INFORMATION: Codon-optimized Clostridium autoethanogenum
      LZ1561 pyruvate:ferredoxin oxidoreductase

<400> SEQUENCE: 4

Met Arg Lys Met Lys Thr Met Asp Gly Asn Thr Ala Ala Ala Tyr Ile
1               5                   10                  15

```
Ser Tyr Ala Phe Thr Asp Val Ala Ala Ile Tyr Pro Ile Thr Pro Ser
             20                  25                  30

Ser Pro Met Ala Glu His Val Asp Glu Trp Val Ala Lys Gly Lys Lys
             35                  40                  45

Asn Ile Phe Gly Gln Gln Val Lys Val Met Glu Met Gln Ser Glu Ala
 50                  55                  60

Gly Ala Ser Gly Ala Val His Gly Ser Leu Gln Ala Gly Ala Leu Thr
 65                  70                  75                  80

Ser Thr Tyr Thr Ala Ser Gln Gly Leu Leu Leu Met Ile Pro Asn Met
                 85                  90                  95

Tyr Lys Ile Ala Gly Glu Leu Leu Pro Gly Val Phe His Val Ser Ala
             100                 105                 110

Arg Ala Val Ala Ala Asn Ser Leu Asn Ile Phe Gly Asp His Gln Asp
             115                 120                 125

Val Met Ala Thr Arg Gln Thr Gly Phe Ala Leu Phe Ala Glu Ser Ser
 130                 135                 140

Val Gln Gln Val Met Asp Leu Ser Ala Val Ala His Leu Ser Ala Ile
 145                 150                 155                 160

Lys Gly Arg Val Pro Phe Val Asn Phe Phe Asp Gly Phe Arg Thr Ser
                 165                 170                 175

His Glu Ile Gln Lys Ile Glu Leu Leu Glu Tyr Glu Glu Leu Ala Lys
             180                 185                 190

Leu Val Asp Gln Lys Ala Leu Asn Asp Phe Arg Arg Arg Ala Leu Asn
             195                 200                 205

Pro Asp His Pro Val Thr Arg Gly Thr Ala Gln Asn Pro Asp Ile Tyr
210                 215                 220

Phe Gln Glu Arg Glu Val Ser Asn Thr Tyr Tyr Glu Ala Leu Pro Glu
225                 230                 235                 240

Ile Val Glu Gly Tyr Met Gln Glu Met Thr Lys Leu Thr Gly Arg Glu
                 245                 250                 255

Tyr His Leu Phe Asn Tyr Tyr Gly Ala Lys Asp Ala Glu Arg Ile Ile
             260                 265                 270

Ile Ala Met Gly Ser Val Cys Glu Thr Val Glu Glu Val Ile Asp Tyr
             275                 280                 285

Leu Thr Thr Lys Gly Glu Lys Val Gly Leu Leu Thr Val His Leu Tyr
290                 295                 300

Arg Pro Phe Ser Ile Lys His Phe Met Lys Tyr Ile Pro Lys Thr Val
305                 310                 315                 320

Lys Lys Ile Ala Val Leu Asp Arg Thr Lys Glu Pro Gly Ser Ile Gly
                 325                 330                 335

Glu Pro Leu Tyr Leu Asp Val Lys Asn Ala Phe Tyr Gly Gln Glu Val
             340                 345                 350

Gln Pro Val Ile Val Gly Gly Arg Tyr Gly Leu Gly Ser Lys Asp Val
             355                 360                 365

Leu Pro Ser His Ile Leu Pro Val Phe Glu Asn Leu Lys Ser Asp Lys
370                 375                 380

Pro Lys Asp Arg Phe Thr Leu Ser Ile Val Asp Asp Val Thr Asn Thr
385                 390                 395                 400

Ser Leu Pro Val Gly Glu Asp Ile Asn Thr Thr Pro Glu Gly Thr Thr
                 405                 410                 415

Ala Cys Lys Phe Trp Gly Leu Gly Ser Asp Gly Thr Val Gly Ala Asn
             420                 425                 430
```

-continued

```
Lys Ser Ala Ile Lys Ile Ile Gly Asp His Thr Asp Met Tyr Ala Gln
            435                 440                 445
Gly Tyr Phe Ala Tyr Asp Ser Lys Lys Ser Gly Gly Ile Thr Val Ser
450                 455                 460
His Leu Arg Phe Gly Lys Ser Pro Ile Lys Ser Pro Tyr Leu Ile Asp
465                 470                 475                 480
Lys Ala Asp Phe Val Ala Val His Asn Gln Ser Tyr Val His Lys Tyr
                485                 490                 495
Asp Val Leu Ala Gly Leu Lys Lys Gly Gly Asn Phe Leu Leu Asn Thr
            500                 505                 510
Val Trp Thr Gln Glu Glu Leu Glu Lys Glu Leu Pro Ala Ser Met Lys
        515                 520                 525
Lys Tyr Ile Ala Asn Asn Asp Ile Lys Phe Tyr Thr Leu Asn Ala Val
        530                 535                 540
Lys Ile Ala Gln Glu Ile Gly Leu Gly Gly Arg Ile Asn Met Ile Cys
545                 550                 555                 560
Gln Ser Ala Phe Phe Lys Ile Ala Asn Ile Ile Pro Ile Asp Asp Ala
                565                 570                 575
Val Lys Tyr Leu Lys Glu Ala Val Val Thr Ser Tyr Gly Lys Lys Gly
            580                 585                 590
Gln Lys Val Val Asp Met Asn Asn Ala Ala Ile Asp Lys Gly Val Asn
        595                 600                 605
Ala Val Val Lys Ile Asp Val Pro Ala Ser Trp Lys Asp Ala Glu Asp
        610                 615                 620
Glu Ala Ala Ala Thr Lys Glu Leu Pro Lys Phe Ile Glu Lys Ile Val
625                 630                 635                 640
Asn Pro Met Asn Arg Gln Glu Gly Asp Lys Leu Pro Val Ser Ala Phe
                645                 650                 655
Val Gly Met Glu Asp Gly Thr Phe Pro Ala Gly Thr Ala Ala Tyr Glu
            660                 665                 670
Lys Arg Gly Ile Ala Ile Asn Val Pro Glu Trp Gln Val Asp Lys Cys
        675                 680                 685
Ile Gln Cys Asn Gln Cys Ser Phe Val Cys Pro His Ala Ala Ile Arg
        690                 695                 700
Pro Val Leu Thr Thr Glu Glu Glu Leu Ala Lys Ala Pro Gln Gly Phe
705                 710                 715                 720
Glu Ala Lys Asp Ala Asn Gly Ala Lys Gly Leu Lys Phe Thr Met Ala
                725                 730                 735
Ile Ser Pro Leu Asp Cys Ser Gly Cys Gly Asn Cys Glu Asp Val Cys
            740                 745                 750
Pro Ala Lys Glu Lys Ala Leu Val Met Lys Pro Val Asp Thr Gln Leu
        755                 760                 765
Ser Lys Thr Glu Ala Trp Asp Tyr Ala Val Asn Ala Val Ala His Lys
        770                 775                 780
Asp Asn Pro Met Lys Asp Lys Tyr Ser Val Lys Ala Ser Gln Phe Glu
785                 790                 795                 800
Gln Pro Leu Leu Glu Phe Ser Gly Ala Cys Ala Gly Cys Gly Glu Thr
                805                 810                 815
Pro Tyr Val Lys Leu Val Thr Gln Leu Phe Gly Asp Arg Met Met Ile
            820                 825                 830
Ala Asn Ala Thr Gly Cys Ser Ser Ile Trp Gly Ala Ser Ala Pro Ala
        835                 840                 845
Thr Pro Tyr Thr Thr Asn Tyr Arg Gly His Gly Pro Ser Trp Ala Asn
```

```
      850               855                860
Ser Leu Phe Glu Asp Asn Ala Glu Tyr Gly Leu Gly Met Phe Leu Gly
865                 870                875                 880

Val Lys Gln Thr Arg Glu Arg Leu Gln Asp Lys Ile Glu Glu Ala Leu
            885                 890                895

Lys Gly Ser Leu Ser Ala Glu Leu Lys Ala Ala Phe Glu Asp Trp Ile
                900                 905                910

Lys Asn Phe Ala Glu Gly Glu Gly Thr Arg Glu Arg Ala Asp Lys Ile
            915                 920                925

Thr Ala Leu Leu Glu Lys Glu Lys Gly Ser Asn Asp Leu Leu Asn Asp
        930                 935                940

Ile Tyr Glu Asn Arg Asp Phe Leu Val Lys Arg Ser His Trp Ile Ile
945                 950                955                 960

Gly Gly Asp Gly Trp Gly Tyr Asp Ile Gly Tyr Gly Val Asp His
                965                 970                975

Val Leu Ala Ser Asn Glu Asp Val Asn Ile Leu Val Leu Asp Thr Glu
            980                 985                990

Val Tyr Ser Asn Thr Gly Gly Gln Ser Ser Lys Ser Thr Pro Thr Ala
            995                 1000                1005

Ala Val Ala Lys Phe Ala Ala Ser Gly Lys Lys Thr Lys Lys Lys
        1010                1015            1020

Asp Leu Gly Met Met Ala Met Ser Tyr Gly Tyr Val Tyr Val Ala
        1025            1030            1035

Gln Ile Ser Met Gly Ala Asp Lys Asn Gln Ala Leu Lys Ala Ile
        1040            1045            1050

His Glu Ala Glu Ala Tyr His Gly Pro Ser Leu Ile Ile Ala Tyr
        1055            1060            1065

Ala Pro Cys Ile Asn His Gly Leu Arg Val Gly Met Gly Lys Ser
        1070            1075            1080

Gln Arg Glu Ala Lys Arg Ala Val Asp Cys Gly Tyr Trp Ala Leu
        1085            1090            1095

Tyr Arg Tyr Asn Pro Glu Leu Lys Glu Glu Gly Lys Lys Ser Phe
        1100            1105            1110

Ser Leu Asp Ser Lys Glu Pro Thr Thr Asp Phe Lys Glu Phe Leu
        1115            1120            1125

Met Gly Glu Val Arg Tyr Ser Ser Leu Ala Lys Gln Phe Pro Asp
        1130            1135            1140

Gln Ala Asp Ala Leu Phe Glu Lys Thr Lys Asp Ala Leu Gln
        1145            1150            1155

Arg Ile Ala Gly Tyr Lys Lys Leu Asp Asn Glu Gln
        1160            1165            1170

<210> SEQ ID NO 5
<211> LENGTH: 3725
<212> TYPE: DNA
<213> ORGANISM: Desulfovibrio africanus

<400> SEQUENCE: 5
tctagataag gaggtcggac atgggaaaaa aaatgatgac tactgatgga atactgcaa      60 ctgcacatgt agcttatgca atgagtgaag tagcagcaat atatcctata actcctagta    120
gtactatggg agaagaagca gacgattggg cagcacaggg aagaaaaaat atatttggac    180
aaactttaac tataagagaa atgcaaagtg aagctggtgc tgctggtgca gtacatggtg    240
cattagcagc tggtgcatta actactactt ttactgcaag tcagggatta ttacttatga    300
```

```
tacctaatat gtacaaaata agtggtgaat tattacctgg tgtatttcat gtaactgcaa        360
gagcaatagc agcacatgca cttagtatat ttggagatca tcaagatata tatgcagcaa        420
gacagactgg atttgcaatg ttagcaagta gtagtgtaca agaggcacat gatatggcac        480
ttgtagcaca tttagcagca atagaaagta atgtaccttt tatgcatttt tttgatggat        540
ttagaactag tcatgaaata caaaaaatag aagtattaga ttatgcagat atggcaagtt        600
tagtaaatca aaaagcatta gcagaattta gagcaaaaag tatgaatcct gaacatcctc        660
atgtaagagg aactgcacaa atcctgata tatattttca gggaagagaa gcagcaaatc        720
cttattatct taaagtacct ggaatagtag ctgaatatat gcaaaaagta gcaagtttaa        780
ctggaagaag ttataaactt tttgattatg ttggagcacc tgatgcagaa agggtaatag        840
taagtatggg aagtagttgt gaaactatag aagaagtaat aaatcatctt gcagcaaaag        900
gtgaaaaaat aggacttata aaagtaagac tttatagacc ttttgtaagt gaagcatttt        960
ttgcagcatt acctgcaagt gcaaaagtaa taactgtatt agatagaact aaagaacctg       1020
gtgcacctgg tgatccttta tatcttgatg tatgtagtgc atttgtagaa aggggtgaag       1080
caatgcctaa aatacttgct ggaagatatg gattaggaag taaagaattt agtcctgcaa       1140
tggtaaaaag tgtatatgat aatatgagtg gtgcaaaaaa aaatcatttc actgtaggaa       1200
tagaagatga tgtaactgga actagtttac ctgtagataa tgcatttgca gatactactc       1260
ctaaaggtac tatacaatgt caattttggg gacttggagc agatggaact gttggagcaa       1320
ataaacaagc aataaaaata attggagata atactgattt atttgcacaa ggatatttta       1380
gttatgatag taaaaaagt ggtggaataa ctataagtca tttaagattt ggagaaaaac       1440
ctatacaaag tacttattta gtaaatagag cagattatgt agcatgtcat aatcctgctt       1500
atgtaggaat atatgatata ttagaaggta taaaagatgg tggaactttt gtacttaata       1560
gtccttggag tagtttagaa gatatggata acatttacc tagtggaata aaaagaacta       1620
tagcaaataa gaaattaaaa ttttataata tagatgcagt aaaaatagca actgatgtag       1680
gattaggtgg aagaataaat atgataatgc aaactgcatt ttttaaatta gctggtgtat       1740 tacctttga aaaagcagta gatttattaa aaaaaagtat acataaagct tatggaaaaa       1800
aaggtgaaaa aattgtaaaa atgaatactg atgcagtaga tcaagcagta actagtttac       1860
aagaatttaa atatcctgat agttggaaag atgcaccagc agaaactaaa gcagaaccta       1920
tgactaatga ttttttaaa aatgtagtaa aacctatatt aactcaacaa ggtgataaat       1980
tacctgtatc tgcatttgaa gcagatggaa gatttcctct tggaactagt caatttgaaa       2040
aaagaggtgt agctataaac gtacctcagt gggttcctga aaattgtata cagtgtaatc       2100
aatgtgcatt tgtatgtcct catagtgcaa tacttccagt attagcaaaa gaagaagaat       2160
tagttggagc accagcaaat tttactgcac ttgaagcaaa gggaaaagaa cttaaaggat       2220
ataaatttag aatacagata aatactttag attgtatggg atgtgaaat tgtgcagata       2280 tatgtcctcc taaagaaaaa gcacttgtaa tgcagcctct tgatactcaa agagatgcac       2340
aagtacctaa tttagaatat gcagctagaa tacctgtaaa aagtgaagta ttacctagag       2400
atagttaaaa aggatctcaa tttcaagaac ctttaatgga atttagtggt gcatgtagtg       2460
gatgtggtga aactccttat gtaagagtaa taactcaatt attttggagaa agaatgtta       2520 tagcaaatgc aactggatgt agtagtatat ggggagcaag tgcacctagt atgccttata       2580
aaactaatag acttggacaa ggacctgcat ggggaaatag tttatttgaa gatgcagcag       2640
```

```
aatatggatt tggaatgaat atgagtatgt ttgcaagaag aactcattta gcagatttag    2700
ctgcaaaagc attagaaagt gatgcaagtg gtgatgtaaa agaagcatta caaggttggt    2760
tagctggaaa aaatgatcct ataaaaagta aagaatatgg tgataaactt aaaaaacttt    2820
tagcaggaca aaaagatgga ttattaggac aaatagcagc aatgagtgat ctttatacta    2880
aaaaaagtgt atggatattt ggaggtgatg gatgggctta tgatataagga tatggtggac    2940 ttgatcatgt acttgcatct ggtgaagatg taaatgtatt tgtaatggat actgaagtat    3000
atagtaatac tggtggacaa agtagtaaag caactcctac tggtgcagta gcaaaatttg    3060
cagcagctgg aaaagaact ggaaaaaaag atttagcaag aatggtaatg acttatggat    3120
atgtatatgt agcaactgta tctatgggat atagtaaaca acaatttctt aaagtattaa    3180
aagaagcaga aagttttcct ggacctagtt tagtaatagc ttatgctact tgtataaatc    3240
aaggattaag aaaaggtatg ggaaaaagtc aagatgtaat gaatactgca gtaaaaagtg    3300
gatattggcc tttatttaga tatgatccta gacttgcagc tcagggaaaa aatccttttc    3360
aattagatag taaagcacct gatggaagtg tagaagaatt tcttatgcca caaaatagat    3420
ttgcagtact tgatagaagt tttcctgaag atgcaaaaag attaagagca caagtagcac    3480
atgaattaga tgtaagattt aaagaattag aacacatggc agcaactaat atatttgaaa    3540
gttttgcacc agccggtggt aaagcagatg gatctgtaga ttttggagaa ggtgcagaat    3600
tttgtactag agatgatact cctatgatgg caagacctga tagtggtgaa gcatgtgatc    3660
aaaatagagc tggaactagt gaacaacagg gtgatcttag taaaagaact aaaaaataag    3720
ctagc                                                                3725

<210> SEQ ID NO 6
<211> LENGTH: 1232
<212> TYPE: PRT
<213> ORGANISM: Desulfovibrio africanus

<400> SEQUENCE: 6

Met Gly Lys Lys Met Met Thr Thr Asp Gly Asn Thr Ala Thr Ala His
1               5                   10                  15

Val Ala Tyr Ala Met Ser Glu Val Ala Ala Ile Tyr Pro Ile Thr Pro
                20                  25                  30

Ser Ser Thr Met Gly Glu Glu Ala Asp Asp Trp Ala Ala Gln Gly Arg
            35                  40                  45

Lys Asn Ile Phe Gly Gln Thr Leu Thr Ile Arg Glu Met Gln Ser Glu
        50                  55                  60

Ala Gly Ala Ala Gly Ala Val His Gly Ala Leu Ala Ala Gly Ala Leu
65                  70                  75                  80

Thr Thr Thr Phe Thr Ala Ser Gln Gly Leu Leu Leu Met Ile Pro Asn
                85                  90                  95

Met Tyr Lys Ile Ser Gly Glu Leu Leu Pro Gly Val Phe His Val Thr
                100                 105                 110

Ala Arg Ala Ile Ala Ala His Ala Leu Ser Ile Phe Gly Asp His Gln
            115                 120                 125

Asp Ile Tyr Ala Ala Arg Gln Thr Gly Phe Ala Met Leu Ala Ser Ser
        130                 135                 140

Ser Val Gln Glu Ala His Asp Met Ala Leu Val Ala His Leu Ala Ala
145                 150                 155                 160

Ile Glu Ser Asn Val Pro Phe Met His Phe Phe Asp Gly Phe Arg Thr
                165                 170                 175
```

```
Ser His Glu Ile Gln Lys Ile Glu Val Leu Asp Tyr Ala Asp Met Ala
                180                 185                 190
Ser Leu Val Asn Gln Lys Ala Leu Ala Glu Phe Arg Ala Lys Ser Met
            195                 200                 205
Asn Pro Glu His Pro His Val Arg Gly Thr Ala Gln Asn Pro Asp Ile
        210                 215                 220
Tyr Phe Gln Gly Arg Glu Ala Ala Asn Pro Tyr Tyr Leu Lys Val Pro
225                 230                 235                 240
Gly Ile Val Ala Glu Tyr Met Gln Lys Val Ala Ser Leu Thr Gly Arg
                245                 250                 255
Ser Tyr Lys Leu Phe Asp Tyr Val Gly Ala Pro Asp Ala Glu Arg Val
            260                 265                 270
Ile Val Ser Met Gly Ser Ser Cys Glu Thr Ile Glu Glu Val Ile Asn
        275                 280                 285
His Leu Ala Ala Lys Gly Glu Lys Ile Gly Leu Ile Lys Val Arg Leu
        290                 295                 300
Tyr Arg Pro Phe Val Ser Glu Ala Phe Phe Ala Ala Leu Pro Ala Ser
305                 310                 315                 320
Ala Lys Val Ile Thr Val Leu Asp Arg Thr Lys Glu Pro Gly Ala Pro
                325                 330                 335
Gly Asp Pro Leu Tyr Leu Asp Val Cys Ser Ala Phe Val Glu Arg Gly
            340                 345                 350
Glu Ala Met Pro Lys Ile Leu Ala Gly Arg Tyr Gly Leu Gly Ser Lys
        355                 360                 365
Glu Phe Ser Pro Ala Met Val Lys Ser Val Tyr Asp Asn Met Ser Gly
        370                 375                 380
Ala Lys Lys Asn His Phe Thr Val Gly Ile Glu Asp Asp Val Thr Gly
385                 390                 395                 400
Thr Ser Leu Pro Val Asp Asn Ala Phe Ala Asp Thr Thr Pro Lys Gly
                405                 410                 415
Thr Ile Gln Cys Gln Phe Trp Gly Leu Gly Ala Asp Gly Thr Val Gly
            420                 425                 430
Ala Asn Lys Gln Ala Ile Lys Ile Ile Gly Asp Asn Thr Asp Leu Phe
        435                 440                 445
Ala Gln Gly Tyr Phe Ser Tyr Asp Ser Lys Lys Ser Gly Gly Ile Thr
450                 455                 460
Ile Ser His Leu Arg Phe Gly Glu Lys Pro Ile Gln Ser Thr Tyr Leu
465                 470                 475                 480
Val Asn Arg Ala Asp Tyr Val Ala Cys His Asn Pro Ala Tyr Val Gly
            485                 490                 495
Ile Tyr Asp Ile Leu Glu Gly Ile Lys Asp Gly Gly Thr Phe Val Leu
        500                 505                 510
Asn Ser Pro Trp Ser Ser Leu Glu Asp Met Asp Lys His Leu Pro Ser
        515                 520                 525
Gly Ile Lys Arg Thr Ile Ala Asn Lys Leu Lys Phe Tyr Asn Ile
530                 535                 540
Asp Ala Val Lys Ile Ala Thr Asp Val Gly Leu Gly Gly Arg Ile Asn
545                 550                 555                 560
Met Ile Met Gln Thr Ala Phe Phe Lys Leu Ala Gly Val Leu Pro Phe
                565                 570                 575
Glu Lys Ala Val Asp Leu Leu Lys Lys Ser Ile His Lys Ala Tyr Gly
            580                 585                 590
Lys Lys Gly Glu Lys Ile Val Lys Met Asn Thr Asp Ala Val Asp Gln
```

-continued

```
            595                 600                 605
Ala Val Thr Ser Leu Gln Glu Phe Lys Tyr Pro Asp Ser Trp Lys Asp
            610                 615                 620
Ala Pro Ala Glu Thr Lys Ala Glu Pro Met Thr Asn Glu Phe Phe Lys
625                 630                 635                 640
Asn Val Val Lys Pro Ile Leu Thr Gln Gln Gly Asp Lys Leu Pro Val
                645                 650                 655
Ser Ala Phe Glu Ala Asp Gly Arg Phe Pro Leu Gly Thr Ser Gln Phe
                660                 665                 670
Glu Lys Arg Gly Val Ala Ile Asn Val Pro Gln Trp Val Pro Glu Asn
                675                 680                 685
Cys Ile Gln Cys Asn Gln Cys Ala Phe Val Cys Pro His Ser Ala Ile
            690                 695                 700
Leu Pro Val Leu Ala Lys Glu Glu Leu Val Gly Ala Pro Ala Asn
705                 710                 715                 720
Phe Thr Ala Leu Glu Ala Lys Gly Lys Glu Leu Lys Gly Tyr Lys Phe
                725                 730                 735
Arg Ile Gln Ile Asn Thr Leu Asp Cys Met Gly Cys Gly Asn Cys Ala
            740                 745                 750
Asp Ile Cys Pro Pro Lys Glu Lys Ala Leu Val Met Gln Pro Leu Asp
            755                 760                 765
Thr Gln Arg Asp Ala Gln Val Pro Asn Leu Glu Tyr Ala Ala Arg Ile
            770                 775                 780
Pro Val Lys Ser Glu Val Leu Pro Arg Asp Ser Leu Lys Gly Ser Gln
785                 790                 795                 800
Phe Gln Glu Pro Leu Met Glu Phe Ser Gly Ala Cys Ser Gly Cys Gly
                805                 810                 815
Glu Thr Pro Tyr Val Arg Val Ile Thr Gln Leu Phe Gly Glu Arg Met
                820                 825                 830
Phe Ile Ala Asn Ala Thr Gly Cys Ser Ser Ile Trp Gly Ala Ser Ala
            835                 840                 845
Pro Ser Met Pro Tyr Lys Thr Asn Arg Leu Gly Gln Gly Pro Ala Trp
            850                 855                 860
Gly Asn Ser Leu Phe Glu Asp Ala Ala Glu Tyr Gly Phe Gly Met Asn
865                 870                 875                 880
Met Ser Met Phe Ala Arg Arg Thr His Leu Ala Asp Leu Ala Ala Lys
                885                 890                 895
Ala Leu Glu Ser Asp Ala Ser Gly Asp Val Lys Glu Ala Leu Gln Gly
                900                 905                 910
Trp Leu Ala Gly Lys Asn Asp Pro Ile Lys Ser Lys Glu Tyr Gly Asp
            915                 920                 925
Lys Leu Lys Leu Leu Ala Gly Gln Lys Asp Gly Leu Leu Gly Gln
            930                 935                 940
Ile Ala Ala Met Ser Asp Leu Tyr Thr Lys Lys Ser Val Trp Ile Phe
945                 950                 955                 960
Gly Gly Asp Gly Trp Ala Tyr Asp Ile Gly Tyr Gly Gly Leu Asp His
                965                 970                 975
Val Leu Ala Ser Gly Glu Asp Val Asn Val Phe Val Met Asp Thr Glu
                980                 985                 990
Val Tyr Ser Asn Thr Gly Gly Gln Ser Ser Lys Ala Thr Pro Thr Gly
                995                 1000                1005
Ala Val Ala Lys Phe Ala Ala Ala Gly Lys Arg Thr Gly Lys Lys
            1010                1015                1020
```

| Asp | Leu | Ala | Arg | Met | Val | Met | Thr | Tyr | Gly | Tyr | Val | Tyr | Val | Ala |
|     | 1025 |     |     |     | 1030 |     |     |     |     | 1035 |     |     |     |     |

| Thr | Val | Ser | Met | Gly | Tyr | Ser | Lys | Gln | Gln | Phe | Leu | Lys | Val | Leu |
|     | 1040 |     |     |     |     | 1045 |     |     |     |     | 1050 |     |     |     |

| Lys | Glu | Ala | Glu | Ser | Phe | Pro | Gly | Pro | Ser | Leu | Val | Ile | Ala | Tyr |
|     | 1055 |     |     |     |     | 1060 |     |     |     |     | 1065 |     |     |     |

| Ala | Thr | Cys | Ile | Asn | Gln | Gly | Leu | Arg | Lys | Gly | Met | Gly | Lys | Ser |
|     | 1070 |     |     |     |     | 1075 |     |     |     |     | 1080 |     |     |     |

| Gln | Asp | Val | Met | Asn | Thr | Ala | Val | Lys | Ser | Gly | Tyr | Trp | Pro | Leu |
|     | 1085 |     |     |     |     | 1090 |     |     |     |     | 1095 |     |     |     |

| Phe | Arg | Tyr | Asp | Pro | Arg | Leu | Ala | Ala | Gln | Gly | Lys | Asn | Pro | Phe |
|     | 1100 |     |     |     |     | 1105 |     |     |     |     | 1110 |     |     |     |

| Gln | Leu | Asp | Ser | Lys | Ala | Pro | Asp | Gly | Ser | Val | Glu | Glu | Phe | Leu |
|     | 1115 |     |     |     |     | 1120 |     |     |     |     | 1125 |     |     |     |

| Met | Ala | Gln | Asn | Arg | Phe | Ala | Val | Leu | Asp | Arg | Ser | Phe | Pro | Glu |
|     | 1130 |     |     |     |     | 1135 |     |     |     |     | 1140 |     |     |     |

| Asp | Ala | Lys | Arg | Leu | Arg | Ala | Gln | Val | Ala | His | Glu | Leu | Asp | Val |
|     | 1145 |     |     |     |     | 1150 |     |     |     |     | 1155 |     |     |     |

| Arg | Phe | Lys | Glu | Leu | Glu | His | Met | Ala | Ala | Thr | Asn | Ile | Phe | Glu |
|     | 1160 |     |     |     |     | 1165 |     |     |     |     | 1170 |     |     |     |

| Ser | Phe | Ala | Pro | Ala | Gly | Gly | Lys | Ala | Asp | Gly | Ser | Val | Asp | Phe |
|     | 1175 |     |     |     |     | 1180 |     |     |     |     | 1185 |     |     |     |

| Gly | Glu | Gly | Ala | Glu | Phe | Cys | Thr | Arg | Asp | Asp | Thr | Pro | Met | Met |
|     | 1190 |     |     |     |     | 1195 |     |     |     |     | 1200 |     |     |     |

| Ala | Arg | Pro | Asp | Ser | Gly | Glu | Ala | Cys | Asp | Gln | Asn | Arg | Ala | Gly |
|     | 1205 |     |     |     |     | 1210 |     |     |     |     | 1215 |     |     |     |

| Thr | Ser | Glu | Gln | Gln | Gly | Asp | Leu | Ser | Lys | Arg | Thr | Lys | Lys |
|     | 1220 |     |     |     |     | 1225 |     |     |     |     | 1230 |     |     |

<210> SEQ ID NO 7
<211> LENGTH: 1617
<212> TYPE: DNA
<213> ORGANISM: Clostridium autoethanogenum LZ1561

<400> SEQUENCE: 7

| atggttatga aagctgctga agcagttatc caatgtttaa aaaagaaaa tgtaaatatg | 60 |
| gtatttgggt atcctggtgc tgcagtggtt cctatatatg aagctttgag aaaatcagat | 120 |
| gtgaagcata tattagtaag acaggaacaa gctgcaggac actctgctag tggatatgct | 180 |
| aggtcaactg gagaagttgg agtctgtata gttacatcag gacctggcgc aactaatcta | 240 |
| attactgcca tgctgctgc atatatggat tccattcctc ttgttgttat tacgggtcag | 300 |
| gttaagtcta cattaatcgg aagggatgta ttccaagaat tagatatcac aggtgctaca | 360 |
| gaatctttta caaaatataa ttttcttgta agagatgcta aatctatacc taagactata | 420 |
| aaggaagcat tttatatagc tgaaactggt agaaaaggcc ctgtgcttgt agatatacct | 480 |
| atggatataa tggaagaaga tattgatttt gaatatcctg aaagtgtaaa tataagagga | 540 |
| tacaaaccta ctgttaaagg acactctggg caaataaaga aataatagaa agaatcaaa | 600 |
| gttagcaaga gacctcttat ttgtgcaggt ggcggagtta tactggcaaa tgcacaaaaa | 660 |
| gaactggagc aatttgttaa aaaatcacat atacctgttg ttcatactct tatgggaaaa | 720 |
| ggatgtataa atgaaaatag tgattattat gtaggtttaa taggtactca tggctttgct | 780 |
| tatgccaata agttgtaca aaatgcagat gtactaaatac ttattggagc tagagcttca | 840 |

-continued

```
gatagaactg tcagtggagt aaaaagtttt gcaaaggatg cagatataat tcatatagat    900
atcgatcctg ctgaaatagg taaaattctg aacacttata ttccagtggt tggtgattgt    960
ggaagtgttt tatcggattt aaataaagaa atagtagctc cacagacaga aaaatggatg   1020
gaagaaatta aaaattggaa aaagatttg tatatagaaa gaaagcctac agataaagtt   1080
aatcccaaat atgtgttaaa aactgttct gatacattag gagaagaggt tattttgaca   1140
gcagatgtag gacaaaatca gttgtggtgt gcccgtaatt ttaggatgac agggaataga   1200
aagttttaa cttctggagg cctcggaact atgggatatt ctctcccagc agctattggt   1260
gctaaaattg catgtcctga taagcaagtt atagcttttg caggtgatgg tggatttcaa   1320
atgagtcttt ttgaacttgg aactattgcc gaaaataatc taaacattat tatagtttg   1380
tttaacaact caggactggg tatggttagg gagatacaag acaataaata ttctggtgaa   1440
tttggagtaa atttaggac caatccagat tttgtaaaac ttgcagaagc ctatggatta   1500
aaagctaaga gagtagaaaa tgattctgaa tttaacggag ttttagaga agcattagat   1560
tcaagcaagg catttttaat agagtgcatt gtagatcctc atgagagaac ttttag    1617
```

<210> SEQ ID NO 8
<211> LENGTH: 538
<212> TYPE: PRT
<213> ORGANISM: Clostridium autoethanogenum LZ1561

<400> SEQUENCE: 8

```
Met Val Met Lys Ala Ala Glu Ala Val Ile Gln Cys Leu Lys Lys Glu
1               5                   10                  15

Asn Val Asn Met Val Phe Gly Tyr Pro Gly Ala Ala Val Pro Ile
            20                  25                  30

Tyr Glu Ala Leu Arg Lys Ser Asp Val Lys His Ile Leu Val Arg Gln
        35                  40                  45

Glu Gln Ala Ala Gly His Ser Ala Ser Gly Tyr Ala Arg Ser Thr Gly
    50                  55                  60

Glu Val Gly Val Cys Ile Val Thr Ser Gly Pro Gly Ala Thr Asn Leu
65                  70                  75                  80

Ile Thr Ala Ile Ala Ala Ala Tyr Met Asp Ser Ile Pro Leu Val Val
                85                  90                  95

Ile Thr Gly Gln Val Lys Ser Thr Leu Ile Gly Arg Asp Val Phe Gln
            100                 105                 110

Glu Leu Asp Ile Thr Gly Ala Thr Glu Ser Phe Thr Lys Tyr Asn Phe
        115                 120                 125

Leu Val Arg Asp Ala Lys Ser Ile Pro Lys Thr Ile Lys Glu Ala Phe
    130                 135                 140

Tyr Ile Ala Glu Thr Gly Arg Lys Gly Pro Val Leu Val Asp Ile Pro
145                 150                 155                 160

Met Asp Ile Met Glu Glu Asp Ile Asp Phe Glu Tyr Pro Glu Ser Val
                165                 170                 175

Asn Ile Arg Gly Tyr Lys Pro Thr Val Lys Gly His Ser Gly Gln Ile
            180                 185                 190

Lys Lys Ile Ile Asp Arg Ile Lys Val Ser Lys Arg Pro Leu Ile Cys
        195                 200                 205

Ala Gly Gly Gly Val Ile Leu Ala Asn Ala Gln Lys Glu Leu Glu Gln
    210                 215                 220

Phe Val Lys Lys Ser His Ile Pro Val Val His Thr Leu Met Gly Lys
225                 230                 235                 240
```

Gly Cys Ile Asn Glu Asn Ser Asp Tyr Tyr Val Gly Leu Ile Gly Thr
             245                 250                 255
His Gly Phe Ala Tyr Ala Asn Lys Val Val Gln Asn Ala Asp Val Leu
        260                 265                 270
Ile Leu Ile Gly Ala Arg Ala Ser Asp Arg Thr Val Ser Gly Val Lys
    275                 280                 285
Ser Phe Ala Lys Asp Ala Asp Ile Ile His Ile Asp Ile Asp Pro Ala
290                 295                 300
Glu Ile Gly Lys Ile Leu Asn Thr Tyr Ile Pro Val Val Gly Asp Cys
305                 310                 315                 320
Gly Ser Val Leu Ser Asp Leu Asn Lys Glu Ile Val Ala Pro Gln Thr
                325                 330                 335
Glu Lys Trp Met Glu Glu Ile Lys Asn Trp Lys Lys Asp Leu Tyr Ile
            340                 345                 350
Glu Arg Lys Pro Thr Asp Lys Val Asn Pro Lys Tyr Val Leu Lys Thr
        355                 360                 365
Val Ser Asp Thr Leu Gly Glu Glu Val Ile Leu Thr Ala Asp Val Gly
    370                 375                 380
Gln Asn Gln Leu Trp Cys Ala Arg Asn Phe Arg Met Thr Gly Asn Arg
385                 390                 395                 400
Lys Phe Leu Thr Ser Gly Gly Leu Gly Thr Met Gly Tyr Ser Leu Pro
                405                 410                 415
Ala Ala Ile Gly Ala Lys Ile Ala Cys Pro Asp Lys Gln Val Ile Ala
            420                 425                 430
Phe Ala Gly Asp Gly Gly Phe Gln Met Ser Leu Phe Glu Leu Gly Thr
        435                 440                 445
Ile Ala Glu Asn Asn Leu Asn Ile Ile Val Leu Phe Asn Asn Ser
    450                 455                 460
Gly Leu Gly Met Val Arg Glu Ile Gln Asp Asn Lys Tyr Ser Gly Glu
465                 470                 475                 480
Phe Gly Val Asn Phe Arg Thr Asn Pro Asp Phe Val Lys Leu Ala Glu
                485                 490                 495
Ala Tyr Gly Leu Lys Ala Lys Arg Val Glu Asn Asp Ser Glu Phe Asn
            500                 505                 510
Gly Val Phe Arg Glu Ala Leu Asp Ser Ser Lys Ala Phe Leu Ile Glu
        515                 520                 525
Cys Ile Val Asp Pro His Glu Arg Thr Phe
    530                 535

<210> SEQ ID NO 9
<211> LENGTH: 1677
<212> TYPE: DNA
<213> ORGANISM: Clostridium autoethanogenum LZ1561

<400> SEQUENCE: 9
atgaaaataa agggagctga agtactatta aaatgtatga tggagcaagg tgtagatact      60
gtattcggat atccgggagg agctgttta cctatttatg atgcactata tgctgctaag      120
ggaaagataa ctcacatatc gacttcacat gaacaagggg ctgctcatgc tgcagatgga      180
tatgcaagat ctacaggaaa ggtaggagtt gtaattgcaa catcagggcc gggagctact      240
aatacggtta cagcaattgc tacagcttat atggattccg tacctattgt agtatttaca      300
ggacaggttg cgagaagtct tcttggaaag gattctttc aagaagtaaa tattaaagat      360
attactgcat ccataactaa gaaaagttgc attgtagaaa aggtagagga tttagctgat      420

```
actgtaagag aggcatttca aattgcagtt agtggaagac caggacctgt agtagtagat    480
atacctaaag acgtacaatc agctgaagta gaatatgagc cttttagaag taagctttct    540
gaaattaaag aaaagaaata ttttaattta aatgagtatg gagacagttt aaataaggca    600
atagatatga taaataggag tgagagacct gtaatttatt caggtggagg aactgtcaca    660
tcaggagctc aaaatgaatt gatggaactt gtagaaaaaa tagattcacc aattacctgt    720
tcacttatgg gaataggagc tttcccggga acaatgaatt attatatggg tatggttgga    780
atgcatggaa gccgttgctc aaattatgca gtaagtaatt gtgacttatt aatagctata    840
ggagctaggt ttagtgatag ggttataagc aaggtaagtg cctttgctcc aaaagcaaga    900
ataatacaca tagacattga ccctaaggag tttggcaaaa acgtggatat agatgtagca    960
ataaaaggag atgtaaaaga ggtacttcaa aagattaatt gcaagttaga aaaggccgac   1020
cacagggatt ggatggagaa aataaaacag tggaaaagtg aacagtgtga acctttttaaa  1080 gaatgtaaat taagtcctaa gtttataatg gatacctgt ataatcttac aggaggagaa    1140
tgcataatta ctacagaagt tggccaaaat caaatttgga ctgcacaata ttttaaattc   1200
ttaaagccaa gaacatttgt atcttcaggc ggacttggaa ctatgggctt cggacttgga   1260
gcttctatag gagcatctat gggtaatcca gggaaaaagg taataaatgt agcagggat    1320 gggagcttta aaatgaattc tacagagctt gctactgttg ccaaatataa gctccctatt   1380
gtacaattgc ttttaaataa tcgtgcatta ggcatggtat atcaatgca ggatatgttc    1440 tatggaaaga ggttttcaaa tacagaactt ggaccagatg ttgatttcat gaaacttgga   1500
gaagcgtatg gtataaagac ttttaagata aagacaata gccaggtaga gaaatgctta   1560
aaggaagctc ttgacttaaa tgaacctgta attatagaat gtgatataga taggaaagaa   1620
aaggtatttc ctattgtacc tccgggagcg gctatatcag atttagtaga agagtaa     1677
```

<210> SEQ ID NO 10
<211> LENGTH: 558
<212> TYPE: PRT
<213> ORGANISM: Clostridium autoethanogenum LZ1561

<400> SEQUENCE: 10

```
Met Lys Ile Lys Gly Ala Glu Val Leu Leu Lys Cys Met Met Glu Gln
1               5                   10                  15

Gly Val Asp Thr Val Phe Gly Tyr Pro Gly Gly Ala Val Leu Pro Ile
            20                  25                  30

Tyr Asp Ala Leu Tyr Ala Ala Lys Gly Lys Ile Thr His Ile Ser Thr
        35                  40                  45

Ser His Glu Gln Gly Ala Ala His Ala Ala Asp Gly Tyr Ala Arg Ser
    50                  55                  60

Thr Gly Lys Val Gly Val Ile Ala Thr Ser Gly Pro Gly Ala Thr
65                  70                  75                  80

Asn Thr Val Thr Ala Ile Ala Thr Ala Tyr Met Asp Ser Val Pro Ile
                85                  90                  95

Val Val Phe Thr Gly Gln Val Ala Arg Ser Leu Leu Gly Lys Asp Ser
            100                 105                 110

Phe Gln Glu Val Asn Ile Lys Asp Ile Thr Ala Ser Ile Thr Lys Lys
        115                 120                 125

Ser Cys Ile Val Glu Lys Val Glu Asp Leu Ala Asp Thr Val Arg Glu
    130                 135                 140

Ala Phe Gln Ile Ala Val Ser Gly Arg Pro Gly Pro Val Val Val Asp
145                 150                 155                 160
```

-continued

```
Ile Pro Lys Asp Val Gln Ser Ala Glu Val Glu Tyr Glu Pro Phe Arg
            165                 170                 175

Ser Lys Leu Ser Glu Ile Lys Glu Lys Lys Tyr Phe Asn Leu Asn Glu
        180                 185                 190

Tyr Gly Asp Ser Leu Asn Lys Ala Ile Asp Met Ile Asn Arg Ser Glu
    195                 200                 205

Arg Pro Val Ile Tyr Ser Gly Gly Thr Val Thr Ser Gly Ala Gln
210                 215                 220

Asn Glu Leu Met Glu Leu Val Glu Lys Ile Asp Ser Pro Ile Thr Cys
225                 230                 235                 240

Ser Leu Met Gly Ile Gly Ala Phe Pro Gly Asn Asn Glu Tyr Tyr Met
            245                 250                 255

Gly Met Val Gly Met His Gly Ser Arg Cys Ser Asn Tyr Ala Val Ser
        260                 265                 270

Asn Cys Asp Leu Leu Ile Ala Ile Gly Ala Arg Phe Ser Asp Arg Val
    275                 280                 285

Ile Ser Lys Val Ser Ala Phe Ala Pro Lys Ala Arg Ile Ile His Ile
290                 295                 300

Asp Ile Asp Pro Lys Glu Phe Gly Lys Asn Val Asp Ile Asp Val Ala
305                 310                 315                 320

Ile Lys Gly Asp Val Lys Glu Val Leu Gln Lys Ile Asn Cys Lys Leu
            325                 330                 335

Glu Lys Ala Asp His Arg Asp Trp Met Glu Lys Ile Lys Gln Trp Lys
        340                 345                 350

Ser Glu Gln Cys Glu Pro Phe Lys Glu Cys Lys Leu Ser Pro Lys Phe
    355                 360                 365

Ile Met Asp Thr Leu Tyr Asn Leu Thr Gly Gly Glu Cys Ile Ile Thr
370                 375                 380

Thr Glu Val Gly Gln Asn Gln Ile Trp Thr Ala Gln Tyr Phe Lys Phe
385                 390                 395                 400

Leu Lys Pro Arg Thr Phe Val Ser Ser Gly Gly Leu Gly Thr Met Gly
            405                 410                 415

Phe Gly Leu Gly Ala Ser Ile Gly Ala Ser Met Gly Asn Pro Gly Lys
        420                 425                 430

Lys Val Ile Asn Val Ala Gly Asp Gly Ser Phe Lys Met Asn Ser Thr
    435                 440                 445

Glu Leu Ala Thr Val Ala Lys Tyr Lys Leu Pro Ile Val Gln Leu Leu
450                 455                 460

Leu Asn Asn Arg Ala Leu Gly Met Val Tyr Gln Trp Gln Asp Met Phe
465                 470                 475                 480

Tyr Gly Lys Arg Phe Ser Asn Thr Glu Leu Gly Pro Asp Val Asp Phe
            485                 490                 495

Met Lys Leu Gly Glu Ala Tyr Gly Ile Lys Thr Phe Lys Ile Glu Asp
        500                 505                 510

Asn Ser Gln Val Glu Lys Cys Leu Lys Glu Ala Leu Asp Leu Asn Glu
    515                 520                 525

Pro Val Ile Ile Glu Cys Asp Ile Asp Arg Lys Glu Lys Val Phe Pro
530                 535                 540

Ile Val Pro Pro Gly Ala Ala Ile Ser Asp Leu Val Glu Glu
545                 550                 555
```

<210> SEQ ID NO 11
<211> LENGTH: 486

```
<212> TYPE: DNA
<213> ORGANISM: Clostridium autoethanogenum LZ1561

<400> SEQUENCE: 11
catatgagtg tacttgtaga aaatcatagt ggtgtattaa gtaaagtagc aggattattt      60
agtagaagag gatataacat tcatagttta actgttggag taactggtga tcctgaaata     120
agtagaatga ctatagtaag tattggagat gattatatgt ttgaacaaat atctaaacag     180
cttaataaat tgatagaagt aataaaagta atagaattaa atcctgatgc aagtgtatat     240
agagaattaa gtcttataaa agtaagtgca gaaagtaata caaacttct  tataatggaa     300
agtgtaaata cttttagagg taaaatagta gatatgaatg aaaaaagtat gataatagaa     360
ataactggaa atgaaaaaaa aataagtgca tttatagaat taatgaaacc ttatggaata     420
aaagaaataa taagaactgg attaactgca ttacaaagag gatcaaaatt agaagattaa     480
gagctc                                                                486

<210> SEQ ID NO 12
<211> LENGTH: 158
<212> TYPE: PRT
<213> ORGANISM: Clostridium autoethanogenum LZ1561

<400> SEQUENCE: 12

Met Ser Val Leu Val Glu Asn His Ser Gly Val Leu Ser Lys Val Ala
1               5                   10                  15

Gly Leu Phe Ser Arg Arg Gly Tyr Asn Ile His Ser Leu Thr Val Gly
            20                  25                  30

Val Thr Gly Asp Pro Glu Ile Ser Arg Met Thr Ile Val Ser Ile Gly
        35                  40                  45

Asp Asp Tyr Met Phe Glu Gln Ile Ser Lys Gln Leu Asn Lys Leu Ile
    50                  55                  60

Glu Val Ile Lys Val Ile Glu Leu Asn Pro Asp Ala Ser Val Tyr Arg
65                  70                  75                  80

Glu Leu Ser Leu Ile Lys Val Ser Ala Glu Ser Asn Asn Lys Leu Leu
                85                  90                  95

Ile Met Glu Ser Val Asn Thr Phe Arg Gly Lys Ile Val Asp Met Asn
            100                 105                 110

Glu Lys Ser Met Ile Ile Glu Ile Thr Gly Asn Glu Lys Lys Ile Ser
        115                 120                 125

Ala Phe Ile Glu Leu Met Lys Pro Tyr Gly Ile Lys Glu Ile Ile Arg
    130                 135                 140

Thr Gly Leu Thr Ala Leu Gln Arg Gly Ser Lys Leu Glu Asp
145                 150                 155

<210> SEQ ID NO 13
<211> LENGTH: 486
<212> TYPE: DNA
<213> ORGANISM: Artificial sequence
<220> FEATURE:
<223> OTHER INFORMATION: Mutant Clostridium autoethanogenum LZ1561 IlvN
      (G-10-D) acetolactate synthase

<400> SEQUENCE: 13
catatgagtg tacttgtaga aaatcatagt gatgtattaa gtaaagtagc aggattattt      60
agtagaagag gatataacat tcatagttta actgttggag taactggtga tcctgaaata     120
agtagaatga ctatagtaag tattggagat gattatatgt ttgaacaaat atctaaacag     180
cttaataaat tgatagaagt aataaaagta atagaattaa atcctgatgc aagtgtatat     240
```

```
agagaattaa gtcttataaa agtaagtgca gaaagtaata acaaacttct tataatggaa    300
agtgtaaata cttttagagg taaaatagta gatatgaatg aaaaaagtat gataatagaa    360
ataactggaa atgaaaaaaa aataagtgca tttatagaat taatgaaacc ttatggaata    420
aaagaaataa taagaactgg attaactgca ttacaaagag gatcaaaatt agaagattaa    480
gagctc                                                               486
```

```
<210> SEQ ID NO 14
<211> LENGTH: 158
<212> TYPE: PRT
<213> ORGANISM: Artificial sequence
<220> FEATURE:
<223> OTHER INFORMATION: Mutant Clostridium autoethanogenum LZ1561 IlvN
      (G-10-D) acetolactate synthase

<400> SEQUENCE: 14
```

Met Ser Val Leu Val Glu Asn His Ser Asp Val Leu Ser Lys Val Ala
1               5                   10                  15

Gly Leu Phe Ser Arg Arg Gly Tyr Asn Ile His Ser Leu Thr Val Gly
            20                  25                  30

Val Thr Gly Asp Pro Glu Ile Ser Arg Met Thr Ile Val Ser Ile Gly
        35                  40                  45

Asp Asp Tyr Met Phe Glu Gln Ile Ser Lys Gln Leu Asn Lys Leu Ile
    50                  55                  60

Glu Val Ile Lys Val Ile Glu Leu Asn Pro Asp Ala Ser Val Tyr Arg
65                  70                  75                  80

Glu Leu Ser Leu Ile Lys Val Ser Ala Glu Ser Asn Asn Lys Leu Leu
                85                  90                  95

Ile Met Glu Ser Val Asn Thr Phe Arg Gly Lys Ile Val Asp Met Asn
            100                 105                 110

Glu Lys Ser Met Ile Ile Glu Ile Thr Gly Asn Glu Lys Lys Ile Ser
        115                 120                 125

Ala Phe Ile Glu Leu Met Lys Pro Tyr Gly Ile Lys Glu Ile Ile Arg
    130                 135                 140

Thr Gly Leu Thr Ala Leu Gln Arg Gly Ser Lys Leu Glu Asp
145                 150                 155

```
<210> SEQ ID NO 15
<211> LENGTH: 1671
<212> TYPE: DNA
<213> ORGANISM: Clostridium autoethanogenum LZ1561

<400> SEQUENCE: 15
atgaatagag atataaaaaa agaagtccaa ctaaatacag ctcaaatgct agtaaaatgt    60
ttagaagccg aaggagtaaa gtacatcttt ggtattcctg gtgaagaaaa cctagaaata   120
atgaatgcaa tttcagattc aactattgaa tttatcacaa cccgtcatga gcaaggtgct   180
gcatttatgg ccgacgttta tggacgttta acaggaaaag caggtgtttg cctatcaaca   240
ctaggaccag gtgccactaa cttagtaact ggtgtagcag atgctgatag tgatggtgct   300
ccggttgttg ctattacagg tcaagtaggt actgaaagaa tgcatataac atcgcaccaa   360
tttttagacc tttgcaaaat gttcgaacca atcacaaaga gaagtaaaca aatcgttcgt   420
cctgatactg taagtgagat tataagactt gttttaagt atgctgaaag tgaaaagcct   480
ggagcatgcc acattgattt acctgtaaat attgcaaaaa tgcccgtagg tgctttagaa   540
aagccttttg gaaaagaagat tccaccaaag gaacatgcag atttatcaac aattgaggaa   600
```

-continued

```
gctgcaagtg aaatcttcaa agcaaaaaat cctattatct tagctggaag cggtgctata    660
agaggaaatt cttcaaaagc tgttacggaa tttgcaacta aattgaaaat tccagtaatt    720
aatacgatga tggcaaaagg tattattcca atggataaca agtattcaat gtggacaata    780
ggtattccac aaaagatta tgtaaataaa attattgaag aggctgattt agtaattaca     840
attggatatg atattgtaga atatgcccca tccaaatgga atataaatgg ggacattaaa    900
attgtgcata tcgatgcaag accatcacac atcaataaac tttatcagcc catagtagaa    960
gtagttggtg atatttcaga tgctctatac aatatattga aagaacttc tagcaaagat     1020 gaaccagtaa aagctttgga aattaaatca gaaatgctag ctgaacatga aagctatgca    1080
aatgacaatg cttttccaat gaaaccccaa agaattttaa atgatgttag aaaggtcatg    1140
ggaccacatg acattgtcat atcagatgta ggtgcccata aatgtggat tgccagacat     1200 tataactgct atgagcccaa tacatgtatt atttcaaacg ttttgctac aatgggtatt     1260 ggtgttccag gtgcaattgc agccaaatta ttaatccag ataaaaagt attggctatt     1320 gttggtgatg cggtttcat gatgaataat caagaattag aaacagccct acgtattaaa    1380
actccaattg tagttttaat atttaatgac agtaactacg gttaataaaa gtggaaacaa    1440
gaagaacact atggtaaaag ctgttatgta gattttacta atccagactt tgtaaagctt    1500
gcagaaagta tgtatgcaaa aggatatcga gtagaaaaag cagaagattt aattccaact    1560
ttagaagaag ctttcaaaca aaatgtacct gcagttattg attgtcaagt tgactatggt    1620
gaaaatataa agcttacaaa gcatttaaaa gaagtttatg aaaatatgta a             1671
```

<210> SEQ ID NO 16
<211> LENGTH: 556
<212> TYPE: PRT
<213> ORGANISM: Clostridium autoethanogenum LZ1561

<400> SEQUENCE: 16

```
Met Asn Arg Asp Ile Lys Lys Glu Val Gln Leu Asn Thr Ala Gln Met
1               5                   10                  15

Leu Val Lys Cys Leu Glu Ala Glu Gly Val Lys Tyr Ile Phe Gly Ile
            20                  25                  30

Pro Gly Glu Glu Asn Leu Glu Ile Met Asn Ala Ile Ser Asp Ser Thr
        35                  40                  45

Ile Glu Phe Ile Thr Thr Arg His Glu Gln Gly Ala Ala Phe Met Ala
    50                  55                  60

Asp Val Tyr Gly Arg Leu Thr Gly Lys Ala Gly Val Cys Leu Ser Thr
65                  70                  75                  80

Leu Gly Pro Gly Ala Thr Asn Leu Val Thr Gly Val Ala Asp Ala Asp
                85                  90                  95

Ser Asp Gly Ala Pro Val Val Ala Ile Thr Gly Gln Val Gly Thr Glu
            100                 105                 110

Arg Met His Ile Thr Ser His Gln Phe Leu Asp Leu Cys Lys Met Phe
        115                 120                 125

Glu Pro Ile Thr Lys Arg Ser Lys Gln Ile Val Arg Pro Asp Thr Val
    130                 135                 140

Ser Glu Ile Ile Arg Leu Val Phe Lys Tyr Ala Glu Ser Glu Lys Pro
145                 150                 155                 160

Gly Ala Cys His Ile Asp Leu Pro Val Asn Ile Ala Lys Met Pro Val
                165                 170                 175

Gly Ala Leu Glu Lys Pro Leu Glu Lys Lys Ile Pro Pro Lys Glu His
```

```
            180                 185                 190
Ala Asp Leu Ser Thr Ile Glu Glu Ala Ala Ser Glu Ile Phe Lys Ala
            195                 200                 205

Lys Asn Pro Ile Ile Leu Ala Gly Ser Gly Ala Ile Arg Gly Asn Ser
            210                 215                 220

Ser Lys Ala Val Thr Glu Phe Ala Thr Lys Leu Lys Ile Pro Val Ile
225                 230                 235                 240

Asn Thr Met Met Ala Lys Gly Ile Ile Pro Met Asp Asn Lys Tyr Ser
            245                 250                 255

Met Trp Thr Ile Gly Ile Pro Gln Lys Asp Tyr Val Asn Lys Ile Ile
            260                 265                 270

Glu Glu Ala Asp Leu Val Ile Thr Ile Gly Tyr Asp Ile Val Glu Tyr
            275                 280                 285

Ala Pro Ser Lys Trp Asn Ile Asn Gly Asp Ile Lys Ile Val His Ile
            290                 295                 300

Asp Ala Arg Pro Ser His Ile Asn Lys Leu Tyr Gln Pro Ile Val Glu
305                 310                 315                 320

Val Val Gly Asp Ile Ser Asp Ala Leu Tyr Asn Ile Leu Arg Arg Thr
            325                 330                 335

Ser Ser Lys Asp Glu Pro Val Lys Ala Leu Glu Ile Lys Ser Glu Met
            340                 345                 350

Leu Ala Glu His Glu Ser Tyr Ala Asn Asp Asn Ala Phe Pro Met Lys
            355                 360                 365

Pro Gln Arg Ile Leu Asn Asp Val Arg Lys Val Met Gly Pro His Asp
            370                 375                 380

Ile Val Ile Ser Asp Val Gly Ala His Lys Met Trp Ile Ala Arg His
385                 390                 395                 400

Tyr Asn Cys Tyr Glu Pro Asn Thr Cys Ile Ile Ser Asn Gly Phe Ala
            405                 410                 415

Thr Met Gly Ile Gly Val Pro Gly Ala Ile Ala Ala Lys Leu Ile Asn
            420                 425                 430

Pro Asp Lys Lys Val Leu Ala Ile Val Gly Asp Gly Gly Phe Met Met
            435                 440                 445

Asn Asn Gln Glu Leu Glu Thr Ala Leu Arg Ile Lys Thr Pro Ile Val
            450                 455                 460

Val Leu Ile Phe Asn Asp Ser Asn Tyr Gly Leu Ile Lys Trp Lys Gln
465                 470                 475                 480

Glu Glu His Tyr Gly Lys Ser Cys Tyr Val Asp Phe Thr Asn Pro Asp
            485                 490                 495

Phe Val Lys Leu Ala Glu Ser Met Tyr Ala Lys Gly Tyr Arg Val Glu
            500                 505                 510

Lys Ala Glu Asp Leu Ile Pro Thr Leu Glu Glu Ala Phe Lys Gln Asn
            515                 520                 525

Val Pro Ala Val Ile Asp Cys Gln Val Asp Tyr Gly Glu Asn Ile Lys
            530                 535                 540

Leu Thr Lys His Leu Lys Glu Val Tyr Glu Asn Met
545                 550                 555
```

<210> SEQ ID NO 17
<211> LENGTH: 1680
<212> TYPE: DNA
<213> ORGANISM: Artificial sequence
<220> FEATURE:
<223> OTHER INFORMATION: Codon-optimized Clostridium autoethanogenum
      LZ1561 AlsS acetolactate synthase

<400> SEQUENCE: 17

```
catatgaata gagatataaa aaagaagta caattaaata ctgcacaaat gttagtaaaa      60
tgtttagaag cagaaggagt aaaatatata tttggaatac ctggagaaga aaatttagaa     120
ataatgaatg caatatctga tagtactata gaatttataa ctactagaca tgaacaagga     180
gcagcattta tggcagatgt atatggaaga ttaactggaa aagctggagt ttgtttaagt     240
actttaggac ctggagcaac taatttagta actggagtag cagatgcaga tagtgatgga     300
gcacctgtag tagcaataac tggacaagta ggaactgaaa gaatgcatat aactagtcat     360
caatttttag atttatgtaa aatgtttgaa cctataacta aagaagtaa acaaatagta      420
agacctgata ctgtaagtga ataataaga ttagtattta aatatgcaga aagtgaaaaa      480
cctggagcat gtcatataga tttacctgta aatatagcaa aaatgcctgt tggagcatta     540
gaaaaacctt tagaaaaaaa aatacctcct aaagaacatg cagatttaag tacaatagaa     600
gaagcagcat ctgaaatatt taagcaaaaa atcctataa tattagctgg aagtggagca      660
ataagaggaa atagtagtaa agcagtaact gaatttgcaa ctaaattaaa aatacctgta     720
ataaatacta tgatggcaaa aggaataata cctatggata taaaatatag tatgtggact     780
ataggaatac ctcaaaaaga ttatgtaaat aaaataatag aagaagctga tttagtaata     840
actataggat atgatatagt agaatatgca cctagtaaat ggaatataaa tggagatata     900
aaaatagtac atatagatgc aagacctagt catataaata aattatatca acctatagta     960
gaagtagttg gagatataag tgatgcatta tataatatat aagaagaac tagttcaaaa    1020
gatgaacctg taaaagcatt agaaataaaa agtgaaatgt tagcagaaca tgaaagttat    1080
gcaaatgata atgcatttcc tatgaaacct caaagaatat aaatgatgt aagaaaagta    1140
atgggaccctc atgatatagt aataagtgat gttggagcac ataaaatgtg gatagcaaga    1200
cattataatt gttatgaacc taatacttgt ataataagta atggatttgc aacaatggga    1260
ataggagtac ctgagcaat agcagcaaaa ttaataaatc ctgataaaaa agtattagca    1320
atagttggag atggaggatt tatgatgaat aatcaagaat tagaaactgc attaagaata    1380
aaaactccta tagtagtatt aatatttaat gatagtaatt atggattaat aaaatggaaa    1440
caagaagaac attatggaaa aagttgttat gtagatttta ctaatcctga ttttgtaaaa    1500
ttagcagaaa gtatgtatgc aaaaggatat agagtagaaa aagcagaaga tttaatacct    1560
actttagaag aagcatttaa acaaatgta cctgcagtaa tagattgtca agtagattat    1620
ggagaaaata taaaattaac taaacattta aaagaagtat atgaaaatat gtaagagctc    1680
```

<210> SEQ ID NO 18
<211> LENGTH: 556
<212> TYPE: PRT
<213> ORGANISM: Artificial sequence
<220> FEATURE:
<223> OTHER INFORMATION: Codon-optimized Clostridium autoethanogenum
      LZ1561 AlsS acetolactate synthase

<400> SEQUENCE: 18

```
Met Asn Arg Asp Ile Lys Lys Glu Val Gln Leu Asn Thr Ala Gln Met
1               5                   10                  15

Leu Val Lys Cys Leu Glu Ala Glu Gly Val Lys Tyr Ile Phe Gly Ile
            20                  25                  30

Pro Gly Glu Glu Asn Leu Glu Ile Met Asn Ala Ile Ser Asp Ser Thr
        35                  40                  45
```

-continued

```
Ile Glu Phe Ile Thr Thr Arg His Glu Gln Gly Ala Ala Phe Met Ala
 50                  55                  60

Asp Val Tyr Gly Arg Leu Thr Gly Lys Ala Gly Val Cys Leu Ser Thr
 65                  70                  75                  80

Leu Gly Pro Gly Ala Thr Asn Leu Val Thr Gly Val Ala Asp Ala Asp
                 85                  90                  95

Ser Asp Gly Ala Pro Val Val Ala Ile Thr Gly Gln Val Gly Thr Glu
            100                 105                 110

Arg Met His Ile Thr Ser His Gln Phe Leu Asp Leu Cys Lys Met Phe
            115                 120                 125

Glu Pro Ile Thr Lys Arg Ser Lys Gln Ile Val Arg Pro Asp Thr Val
130                 135                 140

Ser Glu Ile Ile Arg Leu Val Phe Lys Tyr Ala Glu Ser Glu Lys Pro
145                 150                 155                 160

Gly Ala Cys His Ile Asp Leu Pro Val Asn Ile Ala Lys Met Pro Val
                165                 170                 175

Gly Ala Leu Glu Lys Pro Leu Glu Lys Lys Ile Pro Pro Lys Glu His
            180                 185                 190

Ala Asp Leu Ser Thr Ile Glu Glu Ala Ser Glu Ile Phe Lys Ala
            195                 200                 205

Lys Asn Pro Ile Ile Leu Ala Gly Ser Gly Ala Ile Arg Gly Asn Ser
210                 215                 220

Ser Lys Ala Val Thr Glu Phe Ala Thr Lys Leu Lys Ile Pro Val Ile
225                 230                 235                 240

Asn Thr Met Met Ala Lys Gly Ile Ile Pro Met Asp Asn Lys Tyr Ser
                245                 250                 255

Met Trp Thr Ile Gly Ile Pro Gln Lys Asp Tyr Val Asn Lys Ile Ile
                260                 265                 270

Glu Glu Ala Asp Leu Val Ile Thr Ile Gly Tyr Asp Ile Val Glu Tyr
            275                 280                 285

Ala Pro Ser Lys Trp Asn Ile Asn Gly Asp Ile Lys Ile Val His Ile
            290                 295                 300

Asp Ala Arg Pro Ser His Ile Asn Lys Leu Tyr Gln Pro Ile Val Glu
305                 310                 315                 320

Val Val Gly Asp Ile Ser Asp Ala Leu Tyr Asn Ile Leu Arg Arg Thr
                325                 330                 335

Ser Ser Lys Asp Glu Pro Val Lys Ala Leu Glu Ile Lys Ser Glu Met
            340                 345                 350

Leu Ala Glu His Glu Ser Tyr Ala Asn Asp Asn Ala Phe Pro Met Lys
            355                 360                 365

Pro Gln Arg Ile Leu Asn Asp Val Arg Lys Val Met Gly Pro His Asp
370                 375                 380

Ile Val Ile Ser Asp Val Gly Ala His Lys Met Trp Ile Ala Arg His
385                 390                 395                 400

Tyr Asn Cys Tyr Glu Pro Asn Thr Cys Ile Ile Ser Asn Gly Phe Ala
                405                 410                 415

Thr Met Gly Ile Gly Val Pro Gly Ala Ile Ala Ala Lys Leu Ile Asn
                420                 425                 430

Pro Asp Lys Lys Val Leu Ala Ile Val Gly Asp Gly Gly Phe Met Met
            435                 440                 445

Asn Asn Gln Glu Leu Glu Thr Ala Leu Arg Ile Lys Thr Pro Ile Val
450                 455                 460

Val Leu Ile Phe Asn Asp Ser Asn Tyr Gly Leu Ile Lys Trp Lys Gln
```

| | | | | 465 | | | | | 470 | | | | | 475 | | | | | 480 |
|---|---|---|---|---|---|---|---|---|---|---|---|---|---|---|---|---|---|---|---|

Glu Glu His Tyr Gly Lys Ser Cys Tyr Val Asp Phe Thr Asn Pro Asp
                          485                 490                        495

Phe Val Lys Leu Ala Glu Ser Met Tyr Ala Lys Gly Tyr Arg Val Glu
            500                 505                     510

Lys Ala Glu Asp Leu Ile Pro Thr Leu Glu Glu Ala Phe Lys Gln Asn
           515                 520                   525

Val Pro Ala Val Ile Asp Cys Gln Val Asp Tyr Gly Glu Asn Ile Lys
      530                 535                 540

Leu Thr Lys His Leu Lys Glu Val Tyr Glu Asn Met
545                 550                 555

<210> SEQ ID NO 19
<211> LENGTH: 1722
<212> TYPE: DNA
<213> ORGANISM: Bacillus subtilis

<400> SEQUENCE: 19

```
catatgacta aagcaactaa agaacaaaaa agtttagtaa aaaatagagg tgcagaatta      60
gtagtagatt gtttagtaga acaaggtgta actcatgtat ttggaatacc tggtgcaaaa     120
atagatgcag tatttgatgc attacaagat aaaggacctg aaataatagt agcaagacat     180
gaacaaaatg cagcatttat ggcacaagca gtaggaagat taactggaaa acctggtgta     240
gtacttgtaa ctagtggacc tggtgcatca aatttagcaa ctggattatt aactgcaaat     300
actgaaggtg atcctgtagt agcattagct ggaaatgtaa taagagcaga tagattaaaa     360
agaactcatc aaagtttaga taatgcagca ttatttcaac ctataactaa atattctgta     420
gaagtacaag atgtaaaaaa tatacctgaa gcagtaacta atgcatttag aatagcaagt     480
gcaggacaag ctggtgcagc ttttgtaagt tttcctcagg atgtagtaaa tgaagtaact     540
aatactaaaa atgtaagagc agtagcagca cctaaattag acctgcagc agatgatgca     600
ataagtgcag caatagcaaa aatacaaact gcaaaattac ctgtagtatt agtaggaatg     660
aaaggtggta gacctgaagc aataaaagca gtaagaaaat tacttaaaaa agtacaatta     720
ccttttgtag aaacttatca agcagctgga actttaagta gagatttaga agatcaatat     780
tttggaagaa taggattatt tagaaatcaa cctggtgatt tattacttga caagcagat     840
gtagtattaa ctataggata tgatccaata gaatatgatc taaattttg gaatataaat     900
ggtgatagaa ctataataca tttagatgaa ataatagcag atatagatca tgcatatcaa     960
cctgatttag aattaattgg agatatacct agtactataa atcacataga acatgatgca    1020
gtaaaagtag aatttgcaga aagagaacaa aaaatactta gtgatttaaa acaatatatg    1080
catgaaggtg aacaagtacc tgcagattgg aaaagtgata gagcacatcc tttagaaata    1140
gtaaaagaat taagaaatgc agtagatgat catgtaactg taacttgtga tataggatct    1200
catgcaatat ggatgagtag atatttaga agttatgaac ctttaacttt aatgataagt    1260
aatggaatgc aaactcttgg agtagcatta ccttgggcaa ttggagcatc tttagtaaaa    1320
cctggtgaaa aagtagtaag tgtaagtggt gatggtggat tccttttag tgcaatggaa    1380
ttagaaactg cagtaagatt aaaagcacct atagtacata tagtatgaa tgatagtact    1440
tatgatatgg tagcatttca acaattaaaa aaatataata gaactagtgc agtagatttt    1500
ggaaatatag atatagtaaa atatgcagaa agttttggag caacaggatt aagagtagaa    1560
agtcctgatc aattagcaga tgtacttaga cagggaatga atgcagaagg accagtaata    1620
```

```
attgatgtac ctgtagatta tagtgataat ataaatttag caagtgataa attacctaaa    1680
gaatttggag aattaatgaa aactaaagca ttataagagc tc                       1722
```

<210> SEQ ID NO 20
<211> LENGTH: 570
<212> TYPE: PRT
<213> ORGANISM: Bacillus subtilis

<400> SEQUENCE: 20

```
Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
                20                  25                  30

Phe Gly Ile Pro Gly Ala Lys Ile Asp Ala Val Phe Asp Ala Leu Gln
            35                  40                  45

Asp Lys Gly Pro Glu Ile Ile Val Ala Arg His Glu Gln Asn Ala Ala
        50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
        115                 120                 125

Ala Leu Phe Gln Pro Ile Thr Lys Tyr Ser Val Glu Val Gln Asp Val
    130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
        275                 280                 285

Ile Glu Tyr Asp Pro Lys Phe Trp Asn Ile Asn Gly Asp Arg Thr Ile
    290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
            340                 345                 350

Ser Asp Leu Lys Gln Tyr Met His Glu Gly Glu Gln Val Pro Ala Asp
```

```
                    355                 360                 365
Trp Lys Ser Asp Arg Ala His Pro Leu Glu Ile Val Lys Glu Leu Arg
    370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
            420                 425                 430

Ile Gly Ala Ser Leu Val Lys Pro Gly Glu Lys Val Val Ser Val Ser
        435                 440                 445

Gly Asp Gly Gly Phe Leu Phe Ser Ala Met Glu Leu Glu Thr Ala Val
    450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Asp Val Pro Val
    530                 535                 540

Asp Tyr Ser Asp Asn Ile Asn Leu Ala Ser Asp Lys Leu Pro Lys Glu
545                 550                 555                 560

Phe Gly Glu Leu Met Lys Thr Lys Ala Leu
                565                 570

<210> SEQ ID NO 21
<211> LENGTH: 720
<212> TYPE: DNA
<213> ORGANISM: Clostridium autoethanogenum LZ1561

<400> SEQUENCE: 21
atggatgatg aggtgaaagt cccaaaccat atatatcaaa tgtctacaat aaatgcactt      60
gtttcggggc tgtatgatgg ctgtgtttca ttatctaaac ttcttaaaaa aggaaacttt     120
ggtataggta cttttaaagg tctagatggt gaactaactc tttaaatgg aacttttat      180 aggactaaac ctgatggcag cgtatacgta tgttccaaaa acgtatccgt tcctttgct      240 gtagtcactg aactggaaaa ttataatact tataatattc aaaatcgtac ttcttatgaa     300
gatataagaa aagaattgga cagctttata gaaagcaaaa atatattta tgctttctat     360 atggaaggta aatttaatta tgtaaaaaca cgtactgttg taaaacagaa tatgccttat     420
aagcctatgg ctgaagttgt taaagatcag cctatgtttg aatataacgg tgttgatgga     480
tatgtggttg gatttaggtg tcctgattat gttgaaggcc ttaatgtccc tggatatcat     540
tttcatttca taaataaaga taagaaattt ggtggacata aagtgaatt ttccattgaa      600 aatgcgaagg tttatgtaca gaactgttct tgctttagga tggaacttcc taaaaatgaa     660 agttttata atatgaaagt acaagataga aacgatgaga taacaagtgt tgaaaataa      720

<210> SEQ ID NO 22
<211> LENGTH: 239
<212> TYPE: PRT
<213> ORGANISM: Clostridium autoethanogenum LZ1561
```

<400> SEQUENCE: 22

```
Met Asp Asp Glu Val Lys Val Pro Asn His Ile Tyr Gln Met Ser Thr
1               5                   10                  15
Ile Asn Ala Leu Val Ser Gly Leu Tyr Asp Gly Cys Val Ser Leu Ser
            20                  25                  30
Lys Leu Leu Lys Lys Gly Asn Phe Gly Ile Gly Thr Phe Lys Gly Leu
        35                  40                  45
Asp Gly Glu Leu Thr Leu Leu Asn Gly Thr Phe Tyr Arg Thr Lys Pro
    50                  55                  60
Asp Gly Ser Val Tyr Val Cys Ser Lys Asn Val Ser Val Pro Phe Ala
65                  70                  75                  80
Val Val Thr Glu Leu Glu Asn Tyr Asn Thr Tyr Asn Ile Gln Asn Arg
            85                  90                  95
Thr Ser Tyr Glu Asp Ile Arg Lys Glu Leu Asp Ser Phe Ile Glu Ser
            100                 105                 110
Lys Asn Ile Phe Tyr Ala Phe Tyr Met Glu Gly Lys Phe Asn Tyr Val
            115                 120                 125
Lys Thr Arg Thr Val Val Lys Gln Asn Met Pro Tyr Lys Pro Met Ala
        130                 135                 140
Glu Val Val Lys Asp Gln Pro Met Phe Glu Tyr Asn Gly Val Asp Gly
145                 150                 155                 160
Tyr Val Val Gly Phe Arg Cys Pro Asp Tyr Val Glu Gly Leu Asn Val
                165                 170                 175
Pro Gly Tyr His Phe His Phe Ile Asn Lys Asp Lys Lys Phe Gly Gly
            180                 185                 190
His Ile Ser Glu Phe Ser Ile Glu Asn Ala Lys Val Tyr Val Gln Asn
        195                 200                 205
Cys Ser Cys Phe Arg Met Glu Leu Pro Lys Asn Glu Ser Phe Tyr Asn
        210                 215                 220
Met Glu Val Gln Asp Arg Asn Asp Glu Ile Thr Ser Val Glu Lys
225                 230                 235
```

<210> SEQ ID NO 23
<211> LENGTH: 745
<212> TYPE: DNA
<213> ORGANISM: Artificial sequence
<220> FEATURE:
<223> OTHER INFORMATION: Codon-optimized Clostridium autoethanogenum
    LZ1561 acetolactate decarboxylase

<400> SEQUENCE: 23

```
gagctcagga ggtaactaaa tgatgatga agtaaaagta cctaatcata tatatcaaat    60
gagtactata aatgcattag taagtggatt atatgatgga tgtgtaagtt tatctaaatt   120
attaaaaaaa ggaaattttg gaataggaac ttttaaagga ttagatggag aattaacttt   180
attaaatgga acttttata gaactaaacc tgatggaagt gtatatgtat gtagtaaaaa   240
tgtaagtgta ccttttgcag tagtaactga attagaaaat tataatactt ataatataca   300
aaatagaact tcttatgaag atataagaaa agaattagat agttttatag aaagtaaaaa   360
tatattttat gcattttata tggaaggaaa atttaattat gtaaaaacta gaactgtagt   420
aaaacaaaat atgccttata aacctatggc agaagtagta aagatcaac ctatgtttga   480
atataatgga gtagatggat atgtagtagg atttagatgt cctgattatg tagaaggatt   540
aaatgtacct ggatatcatt ttcattttat aaataaagat aaaaaatttg gaggacatat   600
aagtgaattt agtatagaaa atgcaaaagt atatgtacaa aattgtagtt gttttagaat   660
```

```
ggaattacct aaaaatgaaa gttttaataa tatggaagta caagatagaa atgatgaaat    720
aactagtgta gaaaaataag gtacc                                          745
```

```
<210> SEQ ID NO 24
<211> LENGTH: 239
<212> TYPE: PRT
<213> ORGANISM: Artificial sequence
<220> FEATURE:
<223> OTHER INFORMATION: Codon-optimized Clostridium autoethanogenum
      LZ1561 acetolactate decarboxylase

<400> SEQUENCE: 24
```

Met Asp Asp Glu Val Lys Val Pro Asn His Ile Tyr Gln Met Ser Thr
1               5                   10                  15

Ile Asn Ala Leu Val Ser Gly Leu Tyr Asp Gly Cys Val Ser Leu Ser
            20                  25                  30

Lys Leu Leu Lys Lys Gly Asn Phe Gly Ile Gly Thr Phe Lys Gly Leu
        35                  40                  45

Asp Gly Glu Leu Thr Leu Leu Asn Gly Thr Phe Tyr Arg Thr Lys Pro
    50                  55                  60

Asp Gly Ser Val Tyr Val Cys Ser Lys Asn Val Ser Val Pro Phe Ala
65                  70                  75                  80

Val Val Thr Glu Leu Glu Asn Tyr Asn Thr Tyr Asn Ile Gln Asn Arg
                85                  90                  95

Thr Ser Tyr Glu Asp Ile Arg Lys Glu Leu Asp Ser Phe Ile Glu Ser
            100                 105                 110

Lys Asn Ile Phe Tyr Ala Phe Tyr Met Glu Gly Lys Phe Asn Tyr Val
        115                 120                 125

Lys Thr Arg Thr Val Val Lys Gln Asn Met Pro Tyr Lys Pro Met Ala
    130                 135                 140

Glu Val Val Lys Asp Gln Pro Met Phe Glu Tyr Asn Gly Val Asp Gly
145                 150                 155                 160

Tyr Val Val Gly Phe Arg Cys Pro Asp Tyr Val Glu Gly Leu Asn Val
                165                 170                 175

Pro Gly Tyr His Phe His Phe Ile Asn Lys Asp Lys Phe Gly Gly
            180                 185                 190

His Ile Ser Glu Phe Ser Ile Glu Asn Ala Lys Val Tyr Val Gln Asn
        195                 200                 205

Cys Ser Cys Phe Arg Met Glu Leu Pro Lys Asn Glu Ser Phe Tyr Asn
    210                 215                 220

Met Glu Val Gln Asp Arg Asn Asp Glu Ile Thr Ser Val Glu Lys
225                 230                 235

```
<210> SEQ ID NO 25
<211> LENGTH: 806
<212> TYPE: DNA
<213> ORGANISM: Aeromonas hydrophila

<400> SEQUENCE: 25
```

```
gagctctaag gaggtcggac atggaaacta atagtagttg tgattgtgca atagaaataa    60
gtcaacaatt tgcaagatgg caggcaagac aaggtggtgg tgaagtatat caaagtagtc   120
ttatgagtgc attattagct ggtgtatatg aaggtgaaac tactatggca gatttactta   180
gacatggtga ttttggatta ggaacttta atagattaga tggtgaatta atagcatttg   240
aaagacaaat acatcaatta aaagcagatg gaagtgcaag acctgcaaga gcagaacaaa   300
```

```
aaactcctttt tgcagtaatg actcatttta gaccttgttt acaaagaaga tttgcacatc    360
ctttaagtag agaagaaata catcagtggg tagatagatt agtaggaact gataatgtat    420
ttgtagcatt tagacttgat ggattatttg aacaagcaca agtaagaact gtaccttgtc    480
aaagtcctcc ttataaacct atgttagaag caatagaagc acaacctttta tttagttttta   540 gtttaagaag aggaacttta gtaggattta gatgtcctcc ttttgtacag ggaataaatg    600
tagcaggata tcatgaacat tttataactg aagataaag aggtggtgga catatattag     660
attatgcaat gggacatgga caattacaat taagtgtagt acaacatctt aatatagaat    720
tacctagaaa tcctgcattt caacaagcag atcttaatcc tgcagattta gatagagcaa    780
taagagcagc agaaggataa ggtacc                                          806
```

<210> SEQ ID NO 26
<211> LENGTH: 259
<212> TYPE: PRT
<213> ORGANISM: Aeromonas hydrophila

<400> SEQUENCE: 26

```
Met Glu Thr Asn Ser Ser Cys Asp Cys Ala Ile Glu Ile Ser Gln Gln
1               5                   10                  15

Phe Ala Arg Trp Gln Ala Arg Gln Gly Gly Glu Val Tyr Gln Ser
            20                  25                  30

Ser Leu Met Ser Ala Leu Leu Ala Gly Val Tyr Glu Gly Glu Thr Thr
        35                  40                  45

Met Ala Asp Leu Leu Arg His Gly Asp Phe Gly Leu Gly Thr Phe Asn
    50                  55                  60

Arg Leu Asp Gly Glu Leu Ile Ala Phe Glu Arg Gln Ile His Gln Leu
65                  70                  75                  80

Lys Ala Asp Gly Ser Ala Arg Pro Ala Arg Ala Glu Gln Lys Thr Pro
                85                  90                  95

Phe Ala Val Met Thr His Phe Arg Pro Cys Leu Gln Arg Arg Phe Ala
            100                 105                 110

His Pro Leu Ser Arg Glu Glu Ile His Gln Trp Val Asp Arg Leu Val
        115                 120                 125

Gly Thr Asp Asn Val Phe Val Ala Phe Arg Leu Asp Gly Leu Phe Glu
    130                 135                 140

Gln Ala Gln Val Arg Thr Val Pro Cys Gln Ser Pro Pro Tyr Lys Pro
145                 150                 155                 160

Met Leu Glu Ala Ile Glu Ala Gln Pro Leu Phe Ser Phe Ser Leu Arg
                165                 170                 175

Arg Gly Thr Leu Val Gly Phe Arg Cys Pro Pro Phe Val Gln Gly Ile
            180                 185                 190

Asn Val Ala Gly Tyr His Glu His Phe Ile Thr Glu Asp Arg Arg Gly
        195                 200                 205

Gly Gly His Ile Leu Asp Tyr Ala Met Gly His Gly Gln Leu Gln Leu
    210                 215                 220

Ser Val Val Gln His Leu Asn Ile Glu Leu Pro Arg Asn Pro Ala Phe
225                 230                 235                 240

Gln Gln Ala Asp Leu Asn Pro Asp Leu Asp Arg Ala Ile Arg Ala
                245                 250                 255

Ala Glu Gly
```

<210> SEQ ID NO 27
<211> LENGTH: 761

```
<212> TYPE: DNA
<213> ORGANISM: Leuconostoc lactis

<400> SEQUENCE: 27
gagctctaag gaggtcggac atgactcatc aatataataa aatgagtaga ttatatcaac    60
atggaacttt agcaatgtta atgggaaaac aaatgcaggg aactataact gtagcagaac   120
ttagacaaca tggtgatact ggataggaa ctcttactgg attagatggt gaagtaatac    180
ttcttgatgg tgaagtttat caagcacaga gtgatggaca agtaaatcat ataactaatc   240
ctgatacttt aatgcctttt gcaagtgtac attttgatgc acctactcag cagttacctt   300
ttagtcaggt agattttagt acttaagtg caaaacttaa agcagaacaa ttacaaaatg    360
tatttgcagc agtgaaattt catggtgaat ttagtagagt acatgtaaga atagctccta   420
aacaagtacc tccttatcct tcattacttg cagtagcaga aaatcaacct gaatttgaaa   480
gagaacacgt aactggaact gtagtaggat actttgcacc tcaaatattt aatggaccta   540
ctgcagcagg atggcatgta cattttctta gtgatgatct tcaatttgca ggacatatat   600
tagattttag tgcaagtcaa ataagtggaa ctttacaaat atttgatgaa tttgtacaac   660
atttacctat acatgatcct gcatatagag aaatgacttt agattttgat ggattattag   720
ctggaataga agcaagtgaa ggtggacaac aataaggtac c                       761

<210> SEQ ID NO 28
<211> LENGTH: 244
<212> TYPE: PRT
<213> ORGANISM: Leuconostoc lactis

<400> SEQUENCE: 28
```

Met Thr His Gln Tyr Asn Lys Met Ser Arg Leu Tyr Gln His Gly Thr
 1               5                  10                  15

Leu Ala Met Leu Met Gly Lys Gln Met Gln Gly Thr Ile Thr Val Ala
            20                  25                  30

Glu Leu Arg Gln His Gly Asp Thr Gly Ile Gly Thr Leu Thr Gly Leu
        35                  40                  45

Asp Gly Glu Val Ile Leu Leu Asp Gly Glu Val Tyr Gln Ala Gln Ser
    50                  55                  60

Asp Gly Gln Val Asn His Ile Thr Asn Pro Asp Thr Leu Met Pro Phe
65                  70                  75                  80

Ala Ser Val His Phe Asp Ala Pro Thr Gln Gln Leu Pro Phe Ser Gln
                85                  90                  95

Val Asp Phe Ser Thr Leu Ser Ala Lys Leu Lys Ala Glu Gln Leu Gln
            100                 105                 110

Asn Val Phe Ala Ala Val Lys Phe His Gly Glu Phe Ser Arg Val His
        115                 120                 125

Val Arg Ile Ala Pro Lys Gln Val Pro Pro Tyr Pro Ser Leu Leu Ala
    130                 135                 140

Val Ala Glu Asn Gln Pro Glu Phe Glu Arg Glu His Val Thr Gly Thr
145                 150                 155                 160

Val Val Gly Tyr Phe Ala Pro Gln Ile Phe Asn Gly Pro Thr Ala Ala
                165                 170                 175

Gly Trp His Val His Phe Leu Ser Asp Asp Leu Gln Phe Ala Gly His
            180                 185                 190

Ile Leu Asp Phe Ser Ala Ser Gln Ile Ser Gly Thr Leu Gln Ile Phe
        195                 200                 205

Asp Glu Phe Val Gln His Leu Pro Ile His Asp Pro Ala Tyr Arg Glu

```
            210                 215                 220
Met Thr Leu Asp Phe Asp Gly Leu Leu Ala Gly Ile Glu Ala Ser Glu
225                 230                 235                 240

Gly Gly Gln Gln
```

RECOMBINANT MICROORGANISMS EXHIBITING INCREASED FLUX THROUGH A FERMENTATION PATHWAY

CROSS REFERENCE TO RELATED APPLICATIONS

This application claims the benefit of U.S. Patent Application 62/089,053 filed Dec. 8, 2014 and U.S. Patent Application 62/168,969 filed Jun. 1, 2015, the entirety of which are incorporated herein by reference.

BACKGROUND

Carboxydotrophic microorganisms may be engineered to produce products, such as fuels and chemicals, through fermentation of a gaseous substrate. Efforts to improve product concentration and substrate utilization have historically focused on strain selection and optimization of fermentation conditions (Abubackar, *Bioresour Technol*, 114: 518-522, 2012). The metabolism of natural microorganisms, however, did not evolve to achieve commercial objectives of high yields, rates, and titers, such that certain commercial objectives cannot be achieved through mere strain selection and optimization of fermentation conditions. Accordingly, there remains a need for improved microorganisms and methods for the production of useful products, such as fuels and chemicals.

SUMMARY OF THE INVENTION

The invention provides a recombinant, carboxydotrophic *Clostridium* bacterium comprising one or more enzymes selected from the group consisting of pyruvate:ferredoxin oxidoreductase (EC 1.2.7.1), acetolactate synthase (EC 2.2.1.6), and acetolactate decarboxylase (EC 4.1.1.5), wherein each enzyme is an overexpressed endogenous enzyme, a mutated endogenous enzyme, or an exogenous enzyme. The recombinant bacterium may express one, two, or all three of these enzymes.

The recombinant bacterium may be derived from any *Clostridium* microorganism. In one embodiment, the recombinant bacterium is derived from *C. autoethanogenum, C. ljungdahlii*, or *C. ragsdalei*. In a preferred embodiment, the recombinant bacterium is derived from *C. autoethanogenum* deposited under DSMZ Accession No. DSM23693 (*C. autoethanogenum* LZ1561).

The invention further provides a method of producing a fermentation product, comprising fermenting the recombinant bacterium in the presence of a gaseous substrate comprising CO to produce one or more of ethanol, butanol, isopropanol, isobutanol, higher alcohols, butanediol, 2,3-butanediol, succinate, isoprenoids, fatty acids, biopolymers, and mixtures thereof.

DETAILED DESCRIPTION OF THE INVENTION

Figure 1:
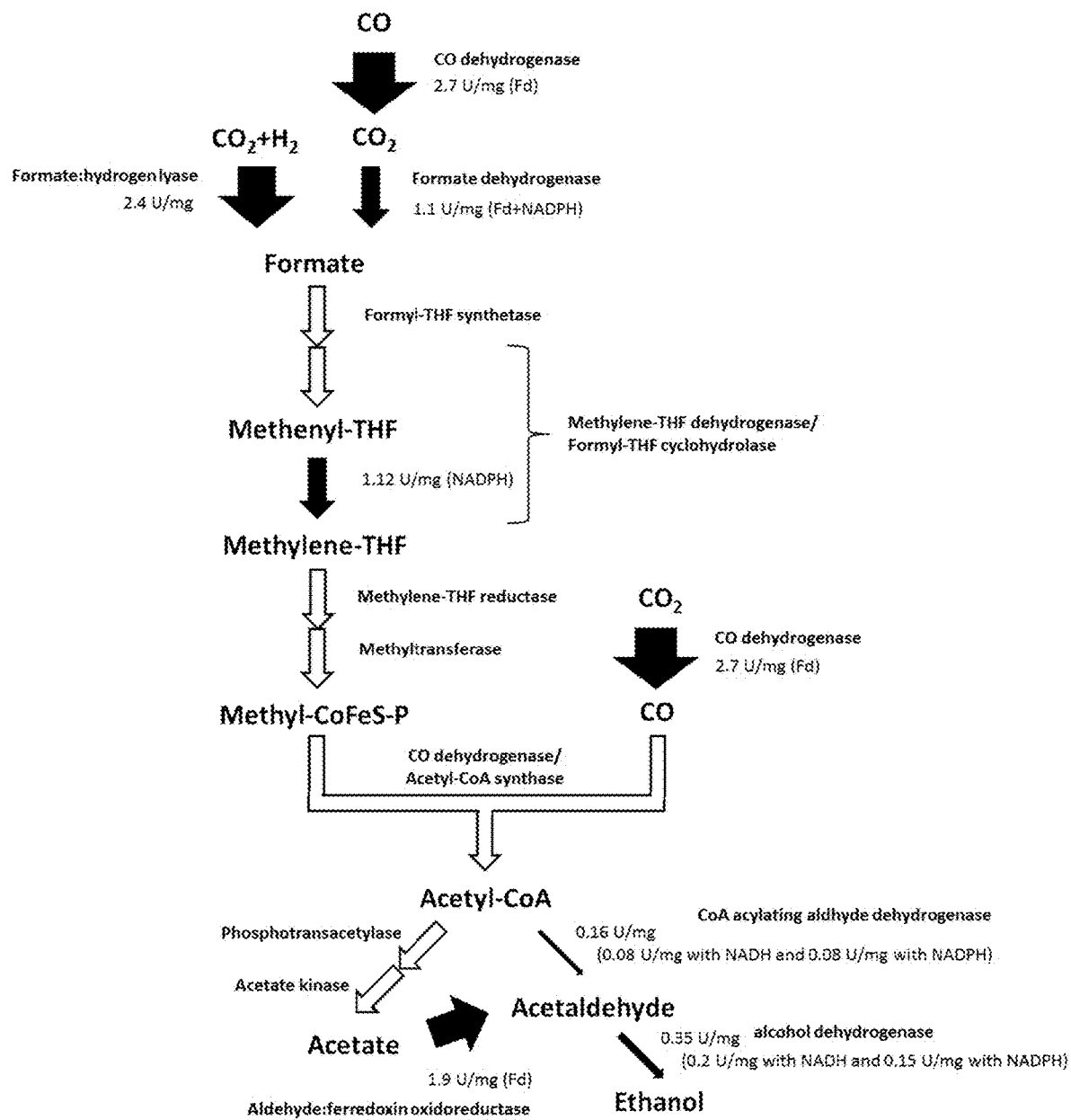
FIG. 1 is a flux map of the ethanol biosynthesis pathway detailing the measured enzyme activities and flux through a carboxydotrophic microorganism for ethanol formation via acetyl-CoA, which allows for the identification of rate-limiting pathway reactions. The thickness of the arrows is proportional to the activity of the particular pathway reaction.

A fermentation pathway is a cascade of biochemical reactions (pathway reactions) by which a substrate, preferably a gaseous substrate, is converted to a fermentation product. Pathway reactions typically involve enzymes that catalyse or increase the rate of the pathway reaction.

"Flux" refers to the flow of metabolites through one or more reactions in a fermentation pathway. The flux through individual pathway reactions has an upper and lower limit. Therefore, the flux may be changed by adjusting conditions or factors that affect enzymatic activity. Adjustment of the flux through one pathway reaction may alter the overall flux of the fermentation pathway. Flux may be measured according to any method known in the art. By way of example, flux may be measured using flux-balance analysis (FBA) (Gianchandani, *Systems Biol Medicine*, 2: 372-382, 2010). Flux through the pathway may also be measured by the level of metabolites and products (metabolomics) (Patti, *Nat Rev Molec Cell Biol*, 13: 263-269, 2012) and/or labelling experiments as C13 (fluxomics) (Niittylae, *Methods Mol Biol*, 553: 355-372, 2009; Tang, *Mass Spectrom Rev*, 28:362-375, 2009).

The efficiency of a fermentation pathway can be increased by increasing the reaction flux through the pathway. The increased flux results in one or more of: an increased rate of growth of microorganisms performing the fermentation, an increased rate of growth and/or product production rate at elevated product concentrations, an increased fermentation product concentration in the fermentation broth, an increased volume of fermentation product produced per volume of substrate consumed, an increased rate of production or level of production of the fermentation product.

Preferably, the increased efficiency results in an increased fermentation product production rate.

One method to identify rate limiting reactions (bottlenecks) is to measure enzyme activities for all reactions involved in the fermentation pathway from substrate to product. This can be done by analysing the enzymatic activity of reactions in cells growing under process conditions to identify the reactions with the lowest rates. These can then be adjusted so as not to be rate limiting, thus increasing the flux throughout the system. Enzymatic activity may be measured by any method known in the art, such as the methods described in Huang, *J Bacteriol*, 194: 3689-3699, 2012.

The inventors have analysed the activity of enzymes involved in fermentation pathways and found that some pathway reactions exhibit substantially lower enzymatic activity than other reactions in the same pathway. The recombinant microorganisms and methods described herein have particular utility for pathways where the product yield in a parental microorganism may lack the product yield to be a viable commercial target.

Examples of fermentation pathways that are amenable to analysis of enzyme activity include the Wood-Ljungdahl pathway, fermentation pathways to produce ethanol, 2,3-butanediol or a precursor thereof such as acetyl-CoA and pyruvate, and biosynthesis pathways for cofactors tetrahydrofolate and cobalamine ($B_{12}$) which may be required in fermentation pathways. The Wood-Ljungdahl pathway is composed of a number of reactions catalysed by enzymes, as described in FIG. 1 and FIG. 2. The steps subsequent to the Wood-Ljungdahl pathway which lead to the production of desirable fermentation products are also considered to be part of the fermentation pathway. In a particular embodiment, the fermentation pathway results in the production of a fermentation product selected from the group consisting of ethanol, butanol, isopropanol, isobutanol, higher alcohols, butanediol, 2,3-butanediol, succinate, isoprenoids, fatty acids, biopolymers, and mixtures thereof.

The invention provides a recombinant, carboxydotrophic *Clostridium* bacterium comprising one or more enzymes selected from the group consisting of pyruvate:ferredoxin oxidoreductase (EC 1.2.7.1), acetolactate synthase (EC 2.2.1.6), and acetolactate decarboxylase (EC 4.1.1.5), wherein each enzyme is an overexpressed endogenous enzyme, a mutated endogenous enzyme, or an exogenous enzyme.

A "parental microorganism" is a microorganism used to generate a recombinant microorganism of the invention. The parental microorganism may be one that occurs in nature (i.e., a wild type microorganism) or one that has been previously modified (i.e. a recombinant microorganism). The recombinant microorganisms of the invention may be modified to express or overexpress one or more enzymes that were or were not expressed or overexpressed in the parental microorganism, or may be modified to exhibit increased availability of one or more co-factors. In one embodiment, the parental organism may be *C. autoethanogenum*, *C. ljungdahlii*, or *C. ragsdalei*. In a particularly preferred embodiment, the parental organism is *C. autoethanogenum* LZ1561, which is deposited under DSMZ accession DSM23693.

A "recombinant microorganism" is a microorganism that has undergone genetic modification when compared to a parental microorganism. Genetic modification includes insertion, deletion, or substitution of nucleic acids, for example.

In general, the term "derived from" indicates that a nucleic acid, protein, or microorganism is modified or adapted from a different (i.e., a parental or wild-type) nucleic acid, protein, or microorganism, respectively, so as to produce a new recombinant microorganism.

Methods of genetic modification of a parental microorganism include molecular methods such as heterologous gene expression, genome insertion or deletion, altered gene expression or inactivation of genes, or enzyme engineering methods. Such techniques are described, for example, in Sambrook, Molecular Cloning: A Laboratory Manual, Cold Spring Harbor Laboratory Press, Cold Spring Harbor, N.Y., 2001; Pleiss, *Curr Opin Biotechnol*, 22: 611-617, 2011; Park, Protein Engineering and Design, CRC Press, 2010. Expression constructs/vectors may contain, for example, one or more promoters or ribosomal binding sites. Nucleic acids and construct/vector sequences described herein may also contain standard linker nucleotides such as those required for ribosome binding sites and/or restriction sites.

Nucleic acids and nucleic acid constructs, including expression constructs/vectors of the invention may be constructed using any method known in the art. For example, chemical synthesis or recombinant techniques may be used. Such techniques are described, for example, in Sambrook, Molecular Cloning: A Laboratory Manual, Cold Spring Harbor Laboratory Press, Cold Spring Harbor, N. Y., 1989. Essentially, the individual genes and regulatory elements may be operably linked to one another such that the genes can be expressed to form the desired proteins. Suitable vectors will be appreciated by those of ordinary skill in the art. However, by way of example, the following vectors may be suitable: pMTL80000 vectors, pIMP1, pJIR750, and other plasmids.

Nucleic acids may be delivered to a microorganism using any method known in the art. For example, nucleic acids may be delivered to a microorganism as naked nucleic acids or may be formulated with one or more agents (e.g., liposomes) to facilitate the transformation process to the microorganism. The nucleic acids may be DNA, RNA, cDNA, or combinations thereof, as is appropriate. Restriction inhibitors may be used in certain embodiments (Murray, *Microbiol Molec Biol Rev*, 64: 412-434, 2000). Additional vectors include include plasmids, viruses (including bacteriophage), cosmids, and artificial chromosomes. In a preferred embodiment, nucleic acids are delivered to a microorganism using a plasmid. By way of example only, transformation (including transduction or transfection) may be achieved by electroporation, ultrasonication, polyethylene glycol-mediated transformation, chemical or natural competence, protoplast transformation, prophage induction or conjugation. Suitable transformation techniques are described for example in, Sambrook, Molecular Cloning: A Laboratory Manual, Cold Spring Harbor Laboratory Press, Cold Spring Harbor, N.Y., 1989.

The use of electroporation has been reported for several carboxydotrophic acetogens, including *C. ljungdahlii* (Koepke, *PNAS*, 107:13087-13092, 2010; WO/2012/053905), *C. autoethanogenum* (WO/2012/053905), *C. aceticum* (Schiel-Bengelsdorf, *Synthetic Biol*, 15: 2191-2198, 2012), and *A. woodii* (Strätz, *Appl Environ Microbiol*, 60: 1033-1037, 1994). The use of electroporation has also been reported in *Clostridia*, including *C. acetobutylicum* (Mermelstein, *Biotechnol*, 10: 190-195, 1992), and *C. cellulolyticum* (Jennert, *Microbiol*, 146: 3071-3080, 2000). Additionally, prophage induction has been demonstrated for carboxydotrophic acetogens, including *C. scatologenes* (Parthasarathy, Development of a Genetic Modification System in *Clostridium scatologenes* ATCC 25775 for Generation of Mutants, Masters Project, Western Kentucky University, 2010), and conjugation has been described for many *Clostridia*, including *C. difficile* (Herbert, *FEMS Microbiol Lett*, 229: 103-110, 2003) and *C. acetobuylicum* (Williams, *J Gen Microbiol*, 136: 819-826, 1990). Similar methods could be used in carboxydotrophic acetogens.

The invention provides a recombinant carboxydotrophic *Clostridium* bacterium adapted to exhibit increased flux through a fermentation pathway relative to a parental microorganism. In one particular embodiment of the invention, the parental microorganism is selected from the group of carboxydotrophic *Clostridia* comprising *C. autoethanogenum, C. ljungdahlii, C. ragsdalei, C. carboxidivorans, C. drakei, C. scatologenes, C. aceticum, C. formicoaceticum*, and *C. magnum*.

The recombinant bacterium may be derived from the cluster of carboxydotrophic *Clostridia* comprising the species *C. autoethanogenum, C. ljungdahlii, C. ragsdalei*, and related isolates. These include but are not limited to strains *C. autoethanogenum* JAI-1T (DSM10061) (Abrini, *Arch Microbiol*, 161: 345-351, 1994), *C. autoethanogenum* LBS1560 (DSM19630) (WO 2009/064200), *C. autoethanogenum* LZ1561 (DSM23693), *C. ljungdahlii* PETCT (DSM13528=ATCC 55383) (Tanner, *Int J Syst Bacteriol*, 43: 232-236, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), *C. ragsdalei* P11T (ATCC BAA-622) (WO 2008/028055), related isolates such as "*C. coskatii*" (U.S. Publication 2011/0229947), or mutated strains such as *C. ljungdahlii* OTA-1 (Tirado-Acevedo, Production of Bioethanol from Synthesis Gas Using *Clostridium ljungdahlii*, PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055). The strains of this cluster are defined by common characteristics, having both a similar genotype and phenotype, and they all share the same mode of energy conservation and fermentative metabolism. The strains of this cluster lack cytochromes and conserve energy via an Rnf complex.

All species of the above-referenced cluster have a similar morphology and size (logarithmic growing cells are between 0.5-0.7×3-5 µm), are mesophilic (optimal growth temperature between 30-37° C.), and are strictly anaerobic (Abrini, *Arch Microbiol*, 161: 345-351, 1994; Tanner, *Int J Syst Bacteriol*, 43: 232-236, 1993; and WO 2008/028055). Moreover, they all share the same major phylogenetic traits, such as same pH range (pH 4-7.5, with an optimal initial pH of 5.5-6), strong autotrophic growth on CO-containing gases with similar growth rates, and a similar metabolic profile with ethanol and acetic acid as main fermentation end products, and small amounts of 2,3-butanediol and lactic acid formed under certain conditions (Abrini, *Arch Microbiol*, 161: 345-351, 1994; Köpke, *Curr Opin Biotechnol*, 22: 320-325, 2011; Tanner, *Int J Syst Bacteriol*, 43: 232-236, 1993; and WO 2008/028055). Indole production was observed with all three species as well. However, the species differentiate in substrate utilization of various sugars (e.g., rhamnose, arabinose), acids (e.g., gluconate, citrate), amino acids (e.g., arginine, histidine), or other substrates (e.g., betaine, butanol). Moreover some of the species were found to be auxotrophic to certain vitamins (e.g., thiamine, biotin) while others were not. The organization and number of Wood-Ljungdahl pathway genes, responsible for gas uptake, has been found to be the same in all species, despite differences in nucleic and amino acid sequences (Köpke, *Curr Opin Biotechnol*, 22: 320-325, 2011). Also, reduction of carboxylic acids into their corresponding alcohols has been shown in a range of these microorganisms (Perez, *Biotechnol Bioeng*, 110:1066-1077, 2012). These traits are therefore not specific to one organism like *C. autoethanogenum* or *C. ljungdahlii*, but rather general traits for carboxydotrophic, ethanol-synthesizing *Clostridia* and it can be anticipated that mechanisms work similarly across these strains, although there may be differences in performance.

In one embodiment, the parental microorganism is *C. autoethanogenum, C. ljungdahlii*, or *C. ragsdalei*. Preferably, the parental microorganism is wild-type *C. autoethanogenum* or *C. autoethanogenum* deposited under DSMZ accession number DSM10061 or DSM23693 (*C. autoethanogenum* LZ1561). In one embodiment, the recombinant bacterium is derived from *C. autoethanogenum, C. ljungdahlii*, or *C. ragsdalei*. Preferably, the recombinant bacterium is derived from wild-type *C. autoethanogenum* or *C. autoethanogenum* deposited under DSMZ accession number DSM23693 (*C. autoethanogenum* LZ1561).

The enzymes and genes of the invention may be overexpressed endogenous enzymes and genes, mutated endogenous enzymes and genes, or exogenous enzymes and genes.

"Endogenous" refers to a nucleic acid or protein that is present in the wild-type or parental bacterium from which the recombinant bacterium of the invention is derived. In one embodiment, the expression of an endogenous gene may be controlled by an exogenous regulatory element, such as an exogenous promoter.

"Exogenous" refers to a nucleic acid or protein that is not present in the wild-type or parental bacterium from which the recombinant bacterium of the invention is derived. In one embodiment, an exogenous gene or enzyme may be derived from a heterologous strain or species and introduced to or expressed in the recombinant bacterium. In another embodiment, an exogenous gene or enzyme may be artificially or recombinantly created. Exogenous nucleic acids may be adapted to integrate into the genome of the bacterium or to remain in an extra-chromosomal state in the bacterium, for example, in a plasmid.

"Enzyme activity" refers broadly to enzymatic activity, including, but not limited, to the activity of an enzyme, the amount of an enzyme, or the availability of an enzyme to catalyse a reaction. Accordingly, "increasing" enzyme activity includes an increase in the activity of an enzyme, an increase in the amount of an enzyme, or an increase in the availability of an enzyme to catalyse a reaction.

The genes and enzymes of the invention may be developed or engineered using any method known in the art, including, for example, directed evolution, knowledge-based design, random mutagenesis methods, gene shuffling, codon optimization, use of site-specific libraries, and use of site evaluation libraries.

"Mutated" refers to a nucleic acid or protein that has been modified in the recombinant bacterium of the invention compared to the wild-type or parental bacterium from which the recombinant bacterium of the invention is derived. In one embodiment, the mutation may be a deletion, insertion, or substitution in a gene encoding an enzyme. In another embodiment, the mutation may be a deletion, insertion, or substitution of one or more amino acids in an enzyme.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes encoding the enzymes of the invention are codon optimized for expression in *Clostridium*, particularly *C. autoethanogenum, C. ljungdahlii*, and/or *C. ragsdalei*. In a further preferred embodiment, the genes encoding the enzymes of the invention are codon optimized for expression in *C. autoethanogenum* LZ1561.

"Overexpressed" refers to any increase in expression of a nucleic acid or protein in the recombinant bacterium of the invention compared to the wild-type or parental bacterium from which the recombinant bacterium of the invention is derived. Overexpression may be achieved by any means known in the art, including modifying gene copy number, gene transcription rate, gene translation rate, or enzyme degradation rate.

"Overexpressed endogenous enzyme" refers to an endogenous enzyme that is present at higher levels in the recombinant bacterium of the invention compared to the wild-type or parental bacterium from which the recombinant bacterium of the invention is derived. The overexpressed endogenous enzyme may likewise be encoded by an endogenous gene, which may be modified, for example, to be controlled by a strong or constitutive promoter. Similarly, "overexpressed endogenous gene" refers to an endogenous gene that is present or transcripted at higher rates or levels in the recombinant bacterium of the invention compared to the wild-type or parental bacterium from which the recombinant bacterium of the invention is derived.

"Mutated endogenous enzyme" refers to an endogenous enzyme that is mutated or modified in the recombinant bacterium of the invention compared to the wild-type or parental bacterium from which the recombinant bacterium of the invention is derived. Similarly, "mutated endogenous gene" refers to an endogenous gene that is mutated or modified in the recombinant bacterium of the invention compared to the wild-type or parental bacterium from which the recombinant bacterium of the invention is derived.

"Exogenous enzyme" refers to an enzyme that is not present in the wild-type or parental bacterium from which the recombinant bacterium of the invention is derived. Similarly, "exogenous gene" refers to a gene that is not present in the wild-type or parental bacterium from which the recombinant bacterium of the invention is derived. Typically, the exogenous enzyme or gene is derived from a heterologous strain or species and introduced to or expressed in the recombinant bacterium.

The invention may be practiced using variant nucleic acids or proteins whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have a similar ability to promote expression of one or more genes. Such nucleic acids or proteins may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered examples of functionally equivalent variants of the sequences specifically exemplified herein. These include homologous genes in species such as *C. acetobutylicum, C. beijerinckii*, or *C. ljungdahlii*, the details of which are publicly available on websites such as Genbank or NCBI. Functionally equivalent variants also includes nucleic acids whose sequence varies as a result of codon optimization for a particular organism. A functionally equivalent variant of a nucleic acid will preferably have at least approximately 70%, approximately 80%, approximately 85%, approximately 90%, approximately 95%, approximately 98%, or greater nucleic acid sequence identity with the specified nucleic acid. A functionally equivalent variant of a protein will preferably have at least approximately 70%, approximately 80%, approximately 85%, approximately 90%, approximately 95%, approximately 98%, or greater amino acid identity with the specified protein. Such variants include a fragment of a protein or peptide wherein the fragment comprises a truncated form of the protein or peptide wherein deletions may be from 1 to 5, to 10, to 15, to 20, to 25 amino acids, and may extend from residue 1 through 25 at either terminus of the polypeptide, and wherein deletions may be of any length within the region or may be at an internal location. The functional equivalence of a variant nucleic acid or protein may be evaluated using any method known in the art. However, by way of example, assays to test for the activity of certain enzymes are described in Huang, *J Bacteriol*, 194: 3689-3699, 2012.

In certain embodiments having active restriction enzyme systems, it may be necessary to methylate a nucleic acid before introduction of the nucleic acid into a microorganism.

Generally, methylation is performed using a shuttle microorganism, preferably a restriction negative shuttle microorganism, such as *E. coli, B. subtillis*, or *L. lactis*, that facilitates the methylation of the nucleic acid sequences that make up the expression construct/vector. The methylation construct/vector comprises a nucleic acid sequence encoding a methyltransferase. Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any method known in the art. In one embodiment, both construct/vector are concurrently isolated. The expression construct/vector may be introduced into the destination microorganism using any method known in the art. Since the expression construct/vector is methylated, the nucleic acid sequences present on the expression construct/vector are able to be incorporated into the destination microorganism and be successfully expressed.

A methyltransferase gene may be introduced into a shuttle microorganism and overexpressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

The expression construct/vector and the methylation construct/vector may be combined to provide a composition of matter. Such a composition has particular utility in circumventing restriction barrier mechanisms to produce the recombinant microorganisms of the invention. In one particular embodiment, the expression construct/vector and/or the methylation construct/vector are plasmids. A number of suitable methyltransferases may be used, including, for example, *B. subtilis* phage ΦT1 methyltransferase or the methyltransferase described in WO 2012/053905. Similarly, a number of constructs/vectors adapted to allow expression of a methyltransferase gene may be used to generate the methylation construct/vector.

By way of example, in one embodiment, a recombinant microorganism of the invention may be produced by a method comprising (a) introduction into a shuttle microorganism of (i) of an expression construct/vector comprising a nucleic acid as described herein and (ii) a methylation construct/vector comprising a methyltransferase gene; and (b) expression of the methyltransferase gene; isolation of one or more constructs/vectors from the shuttle microorganism; and introduction of the one or more construct/vector into a destination microorganism. In one embodiment, the methyltransferase gene of step (b) is expressed constitutively. In another embodiment, expression of the methyltransferase gene of step (b) is induced.

The recombinant bacterium of the invention comprises one or more of pyruvate:ferredoxin oxidoreductase, acetolactate synthase, and acetolactate decarboxylase.

Pyruvate:ferredoxin oxidoreductase (PFOR or POR) (EC 1.2.7.1) is an enzyme belonging to a family of oxidoreductases that catalyses the transfer of electrons from one molecule (the reductant, or electron donor) to another (the oxidant, or electron acceptor). Specifically, pyruvate:ferredoxin oxidoreductase catalyses the interconversion of pyruvate and acetyl-CoA: pyruvate+CoA+2 oxidized ferredoxin↔acetyl-CoA+$CO_2$+2 reduced ferredoxin+2 $H^+$. Conversion of acetyl-CoA to pyruvate links the Wood-Ljungdahl pathway of autotrophic CO(2) fixation to the reductive tricarboxylic acid cycle, which in autotrophic anaerobes is the stage for biosynthesis of all cellular macromolecules (Furdi, *J Biol Chem*, 15: 28494-28499, 2000). Pyruvate:ferredoxin oxidoreductase may also be known as pyruvate:ferredoxin 2-oxidoreductase (CoA-acetylating), pyruvate oxidoreductase, pyruvate synthase, pyruvate synthetase, or pyruvic-ferredoxin oxidoreductase.

The pyruvate:ferredoxin oxidoreductase enzyme of the invention may be an overexpressed endogenous enzyme, a mutated endogenous enzyme, or an exogenous enzyme. Similarly, the pyruvate:ferredoxin oxidoreductase enzyme of the invention may be encoded by an endogenous pyruvate:ferredoxin oxidoreductase gene that has been engineered for overexpression, may be encoded by a mutated endogenous pyruvate:ferredoxin oxidoreductase gene, or may be encoded by an exogenous pyruvate:ferredoxin oxidoreductase gene. In a preferred embodiment, the pyruvate:ferredoxin oxidoreductase enzyme is overexpressed endogenous pyruvate:ferredoxin oxidoreductase, such as overexpressed endogenous *C. autoethanogenum*, *C. ljungdahlii*, or *C. ragsdalei* pyruvate:ferredoxin oxidoreductase. Pyruvate:ferredoxin oxidoreductase enzymes are often unstable in the presence of oxygen. In a preferred embodiment, the pyruvate:ferredoxin oxidoreductase enzyme is oxygen stable or demonstrates at least some degree of oxygen insensitivity. In a further preferred embodiment, the pyruvate:ferredoxin oxidoreductase enzyme is exogenous *Desulfovibrio africanus* pyruvate:ferredoxin oxidoreductase, or an enzyme derived therefrom. Expression of *D. africanus* pyruvate:ferredoxin oxidoreductase has been demonstrated in *E. coli* (Pieulle, *J Bacteriol*, 179: 5684-5692, 1997), but not in a *Clostridium* microorganism.

Acetolactate synthase (Als) (EC 2.2.1.6) is an enzyme that catalyses the first step in the synthesis of branched-chain amino acids, such as valine, leucine, and isoleucine. In particular, acetolactate synthase is a transketolase that has both catabolic and anabolic forms, and catalyses the conversion of two pyruvate molecules to an acetolactate molecule and carbon dioxide: 2 $CH_3COCOO^- \leftrightarrow CH_3COCOHCH_3COO^- + CO_2$. Acetolactate synthase may also be known as acetohydroxy acid synthase.

The acetolactate synthase enzyme of the invention may be an overexpressed endogenous enzyme, a mutated endogenous enzyme, or an exogenous enzyme. Similarly, the acetolactate synthase enzyme of the invention may be encoded by an endogenous acetolactate synthase gene that has been engineered for overexpression, may be encoded by a mutated endogenous acetolactate synthase gene, or may be encoded by an exogenous acetolactate synthase gene. The acetolactate synthase may be anabolic or catabolic. In a preferred embodiment, the acetolactate synthase enzyme is overexpressed endogenous acetolactate synthase, such as overexpressed endogenous *C. autoethanogenum*, *C. ljungdahlii*, or *C. ragsdalei* acetolactate synthase. In particular, the acetolactate synthase enzyme may be overexpressed endogenous IlvB, ILvB ORF2059, IlvB ORF2336, IlvC, IlvN, IlvBN, or AlsS acetolactate synthase. In a preferred embodiment, the acetolactate synthase enzyme is mutated endogenous acetolactate synthase, such as mutated acetolactate synthase derived from any endogenous *C. autoethanogenum*, *C. ljungdahlii*, or *C. ragsdalei* acetolactate synthase. In particular, the mutated endogenous acetolactate synthase may be feedback-insensitive IlvN acetolactate synthase. In a preferred embodiment, the acetolactate synthase enzyme is exogenous acetolactate synthase, such as *Bacillus subtilis* acetolactate synthesis, particularly feedback-insensitive *B. subtilis* AlsS acetolactate synthase. The expression of *B. subtilis* AlsS has been shown in *Synechococcus elongatus* sp. strain PCC 7942 (Oliver, *Metabol Eng*, 22: 76-82, 2014), but not in a *Clostridium* microorganism.

Acetolactate decarboxylase (EC 4.1.1.5) is an enzyme belonging to a family of lyases, specifically the carboxylyases, which cleave carbon-carbon bonds. Acetolactate decarboxylase catalyses the reaction of (S)-2-hydroxy-2-methyl-3-oxobutanoate to (R)-2-acetoin and $CO_2$: (S)-2-hydroxy-2-methyl-3-oxobutanoate↔(R)-2-acetoin+$CO_2$. Acetolactate decarboxylase may also be known as alpha-acetolactate decarboxylase or (S)-2-hydroxy-2-methyl-3-oxobutanoate carboxy-lyase.

The acetolactate decarboxylase enzyme of the invention may be an overexpressed endogenous enzyme, a mutated endogenous enzyme, or an exogenous enzyme. Similarly, the acetolactate decarboxylase enzyme of the invention may be encoded by an endogenous acetolactate decarboxylase gene that has been engineered for overexpression, may be encoded by a mutated endogenous acetolactate decarboxylase gene, or may be encoded by an exogenous acetolactate decarboxylase gene. In a preferred embodiment, the acetolactate decarboxylase enzyme is overexpressed endogenous acetolactate decarboxylase, such as overexpressed endogenous *C. autoethanogenum*, *C. ljungdahlii*, or *C. ragsdalei* acetolactate decarboxylase. The overexpressed endogenous acetolactate decarboxylase may be BudA acetolactate decarboxylase or AlsD acetolactate decarboxylase. In a preferred embodiment, the acetolactate decarboxylase enzyme is exogenous acetolactate decarboxylase, such as *Aeromonas hydrophila* acetolactate decarboxylase or *Leuconostoc lactis* acetolactate decarboxylase. The expression of *B. subtilis* AlsD has been shown in *Synechococcus elongatus* sp. strain PCC 7942 (Oliver, *Metabol Eng*, 22: 76-82, 2014), but not in a *Clostridium* microorganism.

The pyruvate:ferredoxin oxidoreductase, acetolactate synthase, and acetolactate dehydrogenase enzymes may comprise or may be derived from any of the amino acid sequences in the following table. Similarly, the genes encoding the pyruvate:ferredoxin oxidoreductase, acetolactate synthase, and acetolactate dehydrogenase enzymes may comprise or may be derived from any of the nucleic acid sequences in the following table. Moreover, any of the enzymes or genes may be variants of the sequences in the following table. For example, the enzymes or genes may have about 80%, about 90%, about 95%, or about 99% sequence identity to the sequences in the following table.

| SEQ ID NO: | Description |
|---|---|
| 1 | native pyruvate:ferredoxin oxidoreductase, *C. autoethanogenum* LZ1561, nucleic acid sequence |
| 2 | native pyruvate:ferredoxin oxidoreductase, *C. autoethanogenum* LZ1561, amino acid sequence |
| 3 | codon-optimized pyruvate:ferredoxin oxidoreductase with XbaI and NheI, *C. autoethanogenum* LZ1561, nucleic acid sequence |
| 4 | codon-optimized pyruvate:ferredoxin oxidoreductase, *C. autoethanogenum* LZ1561, amino acid sequence |
| 5 | pyruvate:ferredoxin oxidoreductase with XbaI and NehI, *D. africanus*, nucleic acid sequence |
| 6 | pyruvate:ferredoxin oxidoreductase, *D. africanus*, amino acid sequence |
| 7 | native IlvB ORF2059 acetolactate synthase, *C. autoethanogenum* LZ1561, nucleic acid sequence |
| 8 | native IlvB ORF2059 acetolactate synthase, *C. autoethanogenum* LZ1561, amino acid sequence |
| 9 | native IlvB ORF2336 acetolactate synthase, *C. autoethanogenum* LZ1561, nucleic acid sequence |
| 10 | native IlvB ORF2336 acetolactate synthase, *C. autoethanogenum* LZ1561, amino acid sequence |
| 11 | native IlvN acetolactate synthase (regulatory subunit) with NdeI and SacI, *C. autoethanogenum* LZ1561, nucleic acid sequence |
| 12 | native IlvN acetolactate synthase (regulatory subunit), *C. autoethanogenum* LZ1561, amino acid sequence |
| 13 | mutant IlvN (G-10-D) acetolactate synthase (regulatory subunit) with NdeI and SacI, *C. autoethanogenum* LZ1561, nucleic acid sequence |
| 14 | mutant IlvN (G-10-D) acetolactate synthase (regulatory subunit), *C. autoethanogenum* LZ1561, amino acid sequence |
| 15 | native AlsS acetolactate synthase, *C. autoethanogenum* LZ1561, nucleic acid sequence |
| 16 | native AlsS acetolactate synthase, *C. autoethanogenum* LZ1561, amino acid sequence |
| 17 | codon-optimized AlsS acetolactate synthase with NdeI and SacI, *C. autoethanogenum* LZ1561, nucleic acid sequence |
| 18 | codon-optimized AlsS acetolactate synthase, *C. autoethanogenum* LZ1561, amino acid sequence |
| 19 | acetolactate synthase with NdeI and SacI, *B. subtillis*, nucleic acid sequence |
| 20 | acetolactate synthase, *B. subtillis*, amino acid sequence |
| 21 | native acetolactate decarboxylase, *C. autoethanogenum* LZ1561, nucleic acid sequence |
| 22 | native acetolactate decarboxylase, *C. autoethanogenum* LZ1561, amino acid sequence |
| 23 | codon-optimized acetolactate decarboxylase with SacI and KpnI, *C. autoethanogenum* LZ1561, nucleic acid sequence |
| 24 | codon-optimized acetolactate decarboxylase, *C. autoethanogenum* LZ1561, amino acid sequence |
| 25 | acetolactate decarboxylase, *A. hydrophila*, nucleic acid sequence |
| 26 | acetolactate decarboxylase, *A. hydrophila*, amino acid sequence |
| 27 | acetolactate decarboxylase with SacI and KpnI, *L. lactis*, nucleic acid sequence |
| 28 | acetolactate decarboxylase, *L. lactis*, amino acid sequence |

The recombinant bacterium of the invention may also comprise any combination of pyruvate:ferredoxin oxidoreductase, acetolactate synthase, and acetolactate decarboxylase. The bacterium may comprise pyruvate:ferredoxin oxidoreductase and acetolactate synthase, but not acetolactate decarboxylase. The bacterium may comprise pyruvate:ferredoxin oxidoreductase and acetolactate decarboxylase, but not acetolactate synthase. The bacterium may comprise acetolactate synthase and acetolactate decarboxylase, but not pyruvate:ferredoxin oxidoreductase. Finally, the bacterium may comprise each of pyruvate:ferredoxin oxidoreductase, acetolactate synthase, and acetolactate decarboxylase.

The recombinant bacterium of the invention may further express or be engineered to express or overexpress one or more of alcohol dehydrogenase (EC 1.1.1.1), aldehyde dehydrogenase (acylating) (EC 1.2.1.10), formate dehydrogenase (EC 1.2.1.2), formyl-THF synthetase (EC 6.3.2.17), methylene-THF dehydrogenase/formyl-THF cyclohydrolase (EC:6.3.4.3), methylene-THF reductase (EC 1.1,1.58), CO dehydrogenase/acetyl-CoA synthase (EC 2.3.1.169), aldehyde ferredoxin oxidoreductase (EC 1.2.7.5), phosphotransacetylase (EC 2.3.1.8), acetate kinase (EC 2.7.2.1), CO dehydrogenase (EC 1.2.99.2), hydrogenase (EC 1.12.7.2), pyruvate:formate lyase (EC 2.3.1.54), 2,3-butanediol dehydrogenase (EC 1.1.1.4), primary:seconday alcohol dehydrogenase (EC 1.1.1.1), formate dehydrogenase (EC 1.2.1.2), formyl-THF synthetase (EC 6.3.2.17), methylene-THF dehydrogenase/formyl-THF cyclohydrolase (EC:6.3.4.3), methylene-THF reductase (EC 1.1,1.58), CO dehydrogenase/acetyl-CoA synthase (EC 2.3.1.169), CO dehydrogenase (EC 1.2.99.2), and hydrogenase (EC 1.12.7.2).

An "enzyme co-factor" or simply a "co-factor" is a non-protein compound that binds to an enzyme to facilitate the biological function of the enzyme and thus the catalysis of a reaction. Non-limiting examples of co-factors include NAD+, NADP+, cobalamine, tetrahydrofolate and ferredoxin. "Nicotinamide adenine dinucleotide" (NADH) refers to either NAD+ (oxidized form), NADH+H+ (reduced form) or the the redox couple of both NAD+ and NADH+H+. "Nicotinamide adenine dinucleotide phosphate" (NADPH) refers to either NADP+ (oxidized form), NADPH+H+ (reduced form) or the redox couple of both NADP+ and NADPH+H+. Increase in the overall availability of the co-factor can increase the rate of a pathway reaction. Factors that may affect production of the co-factor include the expression of co-factor biosynthesis genes which may be altered to achieve increased availability of the co-factor. Other factors known to one of skill in the art may also be used to achieve increased availability of the co-factor. Lack of availability of co-factors can have rate-limiting effects on pathway reactions. Methods for the determination of availability of co-factors are known in the art.

The recombinant bacterium of the invention may further express or be engineered to express or overexpress an enzyme involved in the biosynthesis of a co-factor. In a particular embodiment, the co-factor comprises tetrahydrofolate. Enzymes that are involved in the biosynthesis of tetrahydrofolate are detailed below. Accordingly, in a particular embodiment, the recombinant microorganism exhibits increased expression of GTP cyclohydrolase I (EC 3.5.4.16), alkaline phosphatase (EC 3.1.3.1), dihydroneopterin aldolase (EC 4.1.2.25), 2-amino-4-hydroxy-6-hydroxymethyldihydropteridine diphosphokinase (EC 2.7.6.3), dihydropteroate synthase (2.5.1.15), dihydropteroate synthase (EC 2.5.1.15), dihydrofolate synthase (EC 6.3.2.12), folylpolyglutamate synthase (6.3.2.17), dihydrofolate reductase (EC 1.5.1.3), thymidylate synthase (EC 2.1.1.45), dihydromonapterin reductase (EC 1.5.1.-). In a particular embodiment, the co-factor comprises cobalamine ($B_{12}$). Enzymes that are involved in the biosynthesis of cobalamine are detailed below. Accordingly, in a particular embodiment, the recombinant microorganism exhibits increased expression of 5-aminolevulinate synthase (EC 2.3.1.37), 5-aminolevulinate:pyruvate aminotransferase (EC 2.6.1.43), adenosylcobinamide kinase/adenosylcobinamide-phosphate guanylyltransferase (EC 2.7.1.156/2.7.7.62), adenosylcobinamide-GDP ribazoletransferase (EC 2.7.8.26), adenosylcobinamide-phosphate synthase (EC 6.3.1.10), adenosylcobyric acid synthase (EC 6.3.5.10), alpha-ribazole phosphatase (EC 3.1.3.73), cob(I)alamin adenosyltransferase (EC 2.5.1.17), cob(II)yrinic acid a,c-diamide reductase (EC 1.16.8.1), cobalt-precorrin 5A hydrolase (EC 3.7.1.12), cobalt-precorrin-5B (C1)-methyltransferase (EC 2.1.1.195), cobalt-precorrin-7 (C15)-methyltransferase (EC 2.1.1.196), cobaltochelatase CobN (EC 6.6.1.2), cobyrinic acid a,c-diamide synthase (EC 6.3.5.9/6.3.5.11), ferritin (EC 1.16.3.1), glutamate-1-semialdehyde 2,1-aminomutase (EC 5.4.3.8), glutamyl-tRNA reductase (EC 1.2.1.70), glutamyl-tRNA synthetase (EC 6.1.1.17), hydroxymethylbilane synthase (EC 2.5.1.61), nicotinate-nucleotide-dimethylbenzimidazole phosphoribosyltransferase (EC 2.4.2.21), oxygen-independent coproporphyrinogen III oxidase (EC 1.3.99.22), porphobilinogen synthase (EC 4.2.1.24), precorrin-2 dehydrogenase/sirohydrochlorin ferrochelatase (EC 1.3.1.76/4.99.1.4), precorrin-2/cobalt-factor-2 C20-methyltransferase (EC 2.1.1.130/2.1.1.151), precorrin-3B synthase (EC 1.14.13.83), precorrin-3B C17-methyltransferase (EC 2.1.1.131), precorrin-4 C11-methyltransferase (EC 2.1.1.133), precorrin-6X reductase (EC 1.3.1.54), precorrin-6Y C5,15-methyltransferase (EC 2.1.1.132), precorrin-8W decarboxylase (EC 1.-.-.-), precorrin-8X methylmutase (EC 5.4.1.2), sirohydrochlorin cobaltochelatase (EC 4.99.1.3), threonine-phosphate decarboxylase (EC 4.1.1.81), uroporphyrinogen decarboxylase (EC 4.1.1.37), uroporphyrinogen III methyltransferase/synthase (EC 2.1.1.107/4.2.1.75). Without wishing to be bound by theory, it is believed that an increase in the availability of a co-factor is achieved through over-expression of enzymes or genes involved in the biosynthesis pathway of said co-factor. As a result, reactions dependent on this co-factor are no longer limiting.

The invention also provides methods for the production of one or more products by fermentation of a substrate comprising CO. Preferably, the product is one or more of ethanol, butanol, isopropanol, isobutanol, higher alcohols, butanediol, 2,3-butanediol, succinate, isoprenoids, fatty acids, biopolymers, and mixtures thereof.

In one embodiment, the substrate comprising CO is a gaseous substrate comprising CO. In one embodiment, the substrate will typically contain a major proportion of CO, such as about 20% to about 100% CO by volume, from 20% to 70% CO by volume, from 30% to 60% CO by volume, or from 40% to 55% CO by volume. In particular embodiments, the substrate comprises about 25%, about 30%, about 35%, about 40%, about 45%, about 50% CO, about 55% CO, or about 60% CO by volume.

While it is not necessary for the substrate to contain any hydrogen, the presence of hydrogen should not be detrimental to product formation in accordance with methods of the invention. In particular embodiments, the presence of hydrogen results in an improved overall efficiency of alcohol production. For example, in particular embodiments, the substrate may comprise an approx. 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, less than 4%, less than 3%, less than 2%, or less than 1% $H_2$. In further embodiments, the substrate stream is substantially hydrogen-free. The substrate may also contain some $CO_2$, for example, about 1% to about 80% $CO_2$ by volume, or 1% to about 30% $CO_2$ by volume. In one embodiment the substrate comprises less than or equal to about 20% $CO_2$ by volume. In particular embodiments, the substrate comprises less than or equal to about 15% $CO_2$ by volume, less than or equal to about 10% $CO_2$ by volume, less than or equal to about 5% $CO_2$ by volume, or substantially no $CO_2$.

Embodiments of the invention are described in terms of delivering and fermenting a "gaseous substrate containing CO." However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak, *Appl Biochem Biotechnol*, 101: 211-227, 2002) could be used. By way of further example, the gaseous substrate containing CO may be adsorbed onto a solid support. Such alternative methods are encompassed by the term "substrate comprising CO" and the like.

The gaseous substrate may be a CO-containing waste gas obtained as a by-product of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Typically, the fermentation is performed in a bioreactor. The term "bioreactor" includes a fermentation device consisting of one or more vessels and/or towers or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors, where appropriate. As used herein, the terms "fermenting," "fermentation process," "fermentation reaction," and the like encompass both the growth phase and product biosynthesis phase of the fermentation process.

In certain embodiments a culture of a bacterium of the invention is maintained in an aqueous culture medium that contains nutrients, vitamins, and/or minerals sufficient to permit growth of the microorganism. Preferably the aqueous culture medium is a minimal anaerobic microbial growth medium. Suitable media are known in the art and described for example in U.S. Pat. Nos. 5,173,429, 5,593,886, and WO 2002/008438.

The fermentation should desirably be carried out under appropriate fermentation conditions for the production of the fermentation product to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of fermentation. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 2002/008438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is controlled to ensure that the concentration of CO in the liquid phase does not become limiting, since products may be consumed by the culture under CO-limited conditions.

The composition of gas streams used to feed a fermentation reaction can have a significant impact on the efficiency and/or cost of the reaction. For example, $O_2$ may reduce the efficiency of an anaerobic fermentation process. Processing of unwanted or unnecessary gases in stages of a fermentation process before or after fermentation can increase the burden on such stages. For example, where the gas stream is compressed before entering a bioreactor, unnecessary energy may be used to compress gases that are not needed in the fermentation. Accordingly, it may be desirable to treat substrate streams, particularly substrate streams derived from industrial sources, to remove unwanted components and increase the concentration of desirable components.

EXAMPLES

The following examples further illustrate the invention but, of course, should not be construed to limit its scope in any way.

Example 1

This example describes the analysis of fermentation pathways of carboxydotrophic bacteria such as *C. autoethanogenum*, *C. ljungdahlii*, or *C. ragsdalei* for bottlenecks in the production of ethanol and 2,3-butanediol.

Oxidoreductase enzyme steps of the Wood-Ljungdahl pathway and fermentation pathways to ethanol and 2,3-butanediol were assayed to determine their activity. Oxidoreductase reactions are particularly suitable since they are coupled with one or more co-factors whose reduction or oxidation can be measured. A synthetic redox dye such as methylviologen or benzylviologen can be used for this purpose as well. The enzymes in these pathways are involved in autotrophic growth including uptake and utilization of CO, $CO_2$, and $H_2$ gases, as well as product formation.

The enzymes assayed and their activities are detailed in FIG. 1. All assays were performed using a synthetic redox dye as control, either methyl viologen (MV) or benzyl viologen (BV). Co-factors ferredoxin (Fd), NADH, and NADPH or a combination thereof were then tested. Enzyme assays were performed using crude extracts from a fermentation growing autotrophically on CO and hydrogen.

Fermentations with *C. autoethanogenum* were carried out in 1.5 L bioreactors at 37° C. using CO-containing steel mill gas as a sole energy and carbon source. The fermentation media contained, per litre, MgCl, $CaCl_2$ (0.5 mM), KCl (2 mM), $H_3PO_4$ (5 mM), Fe (100 µM), Ni, Zn (5 µM), Mn, B, W, Mo, and Se (2 µM). The media was transferred into a bioreactor and autoclaved at 121° C. for 45 minutes. After autoclaving, the media was supplemented with thiamine, pantothenate (0.05 mg) and biotin (0.02 mg) and reduced with 3 mM cysteine-HCl. To achieve anaerobic conditions, the reactor vessel was sparged with nitrogen through a 0.2

μm filter. Prior to inoculation, the gas was switched to CO-containing steel mill gas, feeding continuously to the reactor. The feed gas composition was 2% $H_2$, 42% CO, 20% $CO_2$, and 36% $N_2$. The pH of the culture was maintained between 5 and 5.2.

At the time of harvesting the cells (biomass of 3.9 g cells/l fermentation broth), the gas consumption was 5 moles CO $L^{-1}$ $day^{-1}$ and 10 milimoles $H_2$ $L^{-1}$ $day^{-1}$, with the following metabolites produced: 14 g $L^{-1}$ $day^{-1}$ acetate and 19.5 g $L^{-1}$ $day^{-1}$ ethanol. The pH of the culture was adjusted to pH 6 with $K_2CO_3$ and the reactor chilled in an ice-water bath. Approximately 1.2 L of culture was collected on ice. The culture was divided between two 1-L centrifuge bottles (this and all subsequent steps were carried out in an anaerobic chamber to ensure anoxic conditions to avoid inactivation of the enzymes) and cells were pelleted at 5000 rpm for 10 min. The supernatant was decanted and residual liquid removed. Each pellet was resuspended in approximately 30 mL of 50 mM K $PO_4$ pH 7.0 with 10 mM DTT. Resuspensions were transferred to pre weighed 50-mL-Falcon-tubes and cells repelleted at maximum speed (5000 g) for 15 min. The tubes were removed from the anaerobic chamber and immediately frozen on liquid $N_2$ before assaying.

Cells were harvested from a continuous reactor under anoxic conditions. They were disrupted by three passes through a French press. Unbroken cells and cell debris were removed by centrifugation at 20,000×g and 4° C. for 30 min. The supernatant was used for enzyme assays. Except where indicated, all assays were performed at 37° C. in 1.5-ml anaerobic cuvettes closed with a rubber stopper filled with 0.8 ml reaction mixture and 0.7 ml $N_2$ or $H_2$ or CO at $1.2 \times 10^5$ Pa. Enzymes were assayed as described below or by Huang, *J Bacteriol*, 194: 3689-3699, 2012. After the start of the reaction with enzyme, the reduction of $NAD(P)^+$ or $NAD^+$ was monitored spectrophotometrically at 340 nm ($\varepsilon = 6.2$ $mM^{-1}$ $cm^{-1}$) or at 380 nm ($\varepsilon = 1.2$ $mM^{-1}$ $cm^{-1}$), *C. pasteurianum* ferredoxin reduction at 430 nm ($\varepsilon\Delta_{ox-red} \approx 13.1$ $mM^{-1}$ $cm^{-1}$), methyl viologen reduction at 578 nm (6=9.8 $mM^{-1}$ $cm^{-1}$) and benzyl viologen reduction at 578 nm ($\varepsilon = 8.6$ $mM^{-1}$ $cm^{-1}$).

CO dehydrogenase was measured using an assay mixture that contained 100 mM Tris/HCl (pH 7.5), 2 mM DTT and about 30 μM ferredoxin and/or 1 mM $NAD^+$ or 1 mM $NADP^+$. The gas phase was 100% CO. 0083 Hydrogenase activity was measured using an assay mixture of 100 mM Tris/HCl (pH 7.5) or 100 mM potassium phosphate, 2 mM DTT and, 25 μM ferredoxin and/or 1 mM $NADP^+$ and/or 10 mM methyl viologen. The gas phase was 100% $H_2$.

Formate-hydrogen lyase activity for reduction of $CO_2$ with $H_2$ to formate was measured with an assay mixture containing 100 mM potassium phosphate, 2 mM DTT, and 30 mM [$^{14}$C]$K_2CO_3$ (24,000 dpm/μmol). The gas phase was 100% $H_2$. The serum bottles were continuously shaken at 200 rpm to ensure equilibration of the gas phase with the liquid phase. After start of the reaction with enzyme, 100 μl liquid samples were withdrawn every 1.5 min and added into a 1.5-ml safe seal micro tube containing 100 μl of 150 mM acetic acid to stop the reaction by acidification. The 200 μl mixture was then incubated at 40° C. for 10 min with shaking at 1,400 rpm in a Thermomixer to remove all $^{14}CO_2$ leaving behind the $^{14}$C-formate formed. Subsequently, 100 μl of the mixture was added to 5 ml of Quicksave A scintillation fluid (Zinsser Analytic, Frankfurt, Germany) and analyzed for $^{14}$C radioactivity in a Beckman LS6500 liquid scintillation counter (Fullerton, Calif.).

Formate dehydrogenase measurement was carried out with an assay mixtures containing 100 mM Tris/HCl (pH 7.5) or 100 mM potassium phosphate, 2 mM DTT, 20 mM formate and, where indicated 25 μM ferredoxin, 1 mM $NADP^+$, 1 mM $NAD^+$ and/or 10 mM methyl viologen. The gas phase was 100% $N_2$.

Methylene-$H_4$F dehydrogenase was measured using an assay mixture containing 100 mM MOPS/KOH (pH 6.5), 50 mM 2-mercaptoethanol, 0.4 mM tetrahydrofolate, 10 mM formaldehyde and 0.5 mM $NADP^+$ or 0.5 mM $NAD^+$. The gas phase was 100% $N_2$.

Methylene-$H_4$F reductase was assayed under the following conditions. The assay mixtures contained 100 mM Tris/HCl (pH 7.5), 20 mM ascorbate, 10 μM FAD. 20 mM benzyl viologen and 1 mM methyl-$H_4$F. Before start of the reaction with enzyme, benzyl viologen was reduced to an ΔA555 of 0.3 with sodium dithionite.

Aldehyde:ferredoxin oxidoreductase was assayed using a mixture containing 100 mM Tris/HCl (pH 7.5), 2 mM DTT, 1.1 mM acetaldehyde, and about 25 μM ferredoxin. The gas phase was 100% $N_2$.

CoA acetylating acetaldehyde dehydrogenase was measured using a mixture contained 100 mM Tris/HCl (pH 7.5), 2 mM DTT, 1.1 mM acetaldehyde, 1 mM coenzyme A, and 1 mM NADP+ or 1 mM NAD+. The gas phase was 100% $N_2$.

Alcohol and butanediol dehydrogenases were measured in an assay with 100 mM potassium phosphate (pH 6), 2 mM DTT, 1.1 mM acetaldehyde or acetoin respectively and 1 mM NADPH or 1 mM NADH. The gas phase was 100% $N_2$.

Ferredoxin was purified from *C. pasteurianum* as described by Schönheit, *FEBS Lett*, 89: 219-222, 1978.

All oxidoreductase reactions in the pathways to ethanol and 2,3-butanediol of carboxydotrophic bacterium *C. autoethanogenum* were assayed and successfully detected, with the exception of the methylene-THF reductase which the inventors believe requires an as yet unknown coupling site (Köpke, *PNAS USA*, 107: 13087-13092, 2010; Poehlein, *PLoS One*, 7: e33439, 2012). Activity of this enzyme could not previously be detected in other organisms. Results are provided in FIG. 1 and FIG. 2. This data was used to analyze and determine bottlenecks in these pathways that would typically occur during a fermentation process.

Example 2

This example demonstrates increasing the flux through a fermentation pathway.

The general methods described in Example 3 of PCT/US2014/041188 may also be used to introduce pyruvate:ferredoxin oxidoreductase, acetolactate synthase, and/or acetolactate decarboxylase gene into the recombinant *Clostridium* microorganism of the invention.

Example 3

This example identifies the conversion of acetyl CoA to pyruvate by pyruvate:ferredoxin oxidoreductase as a bottleneck in the production of 2,3-butanediol.

Figure 2:
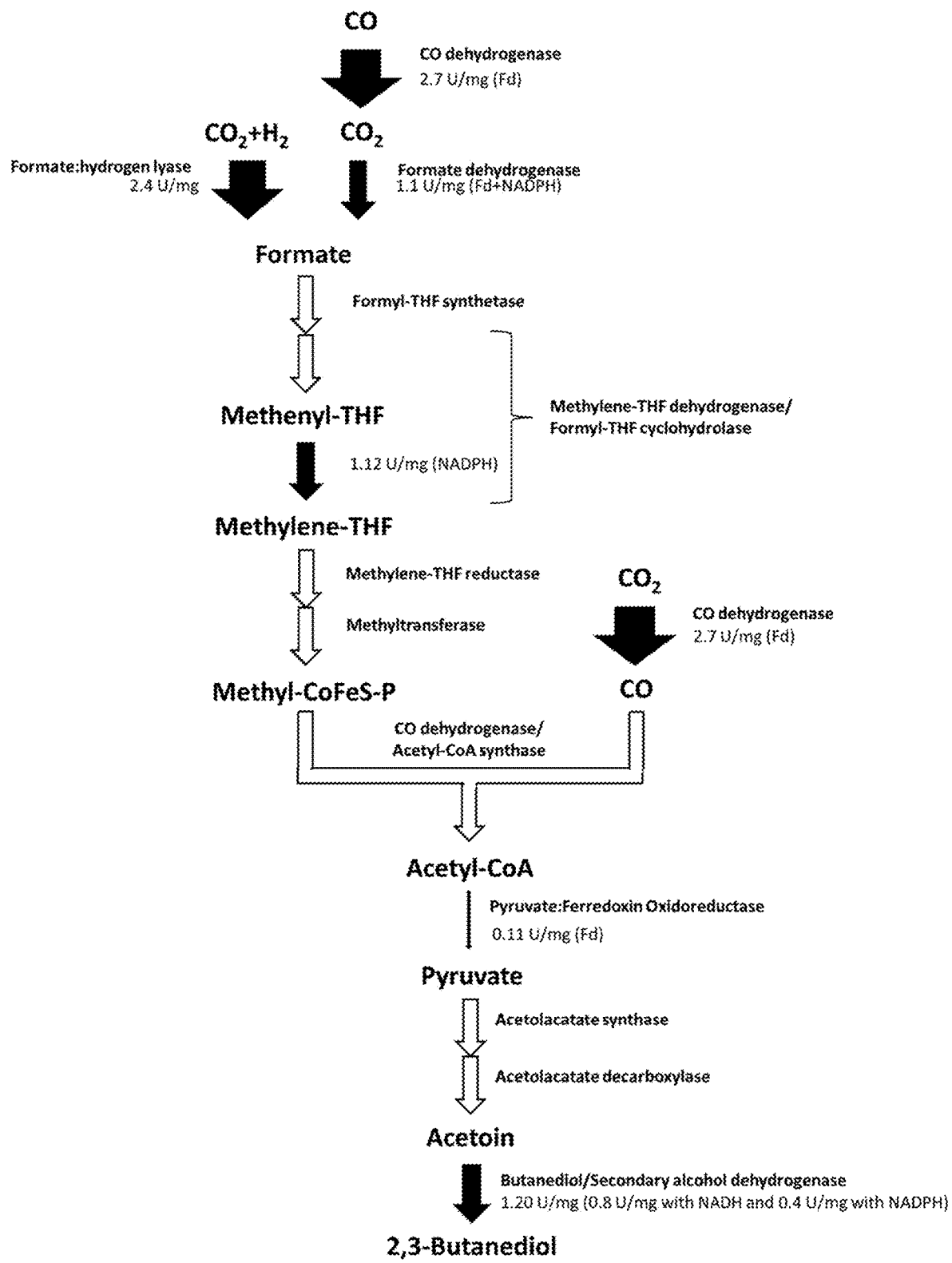
FIG. 2 is a flux map detailing the measured enzyme activities and flux through a carboxydotrophic microorganism for 2,3-butanediol formation via pyruvate, which allows for the identification of rate-limiting pathway reactions.
Figure 3:
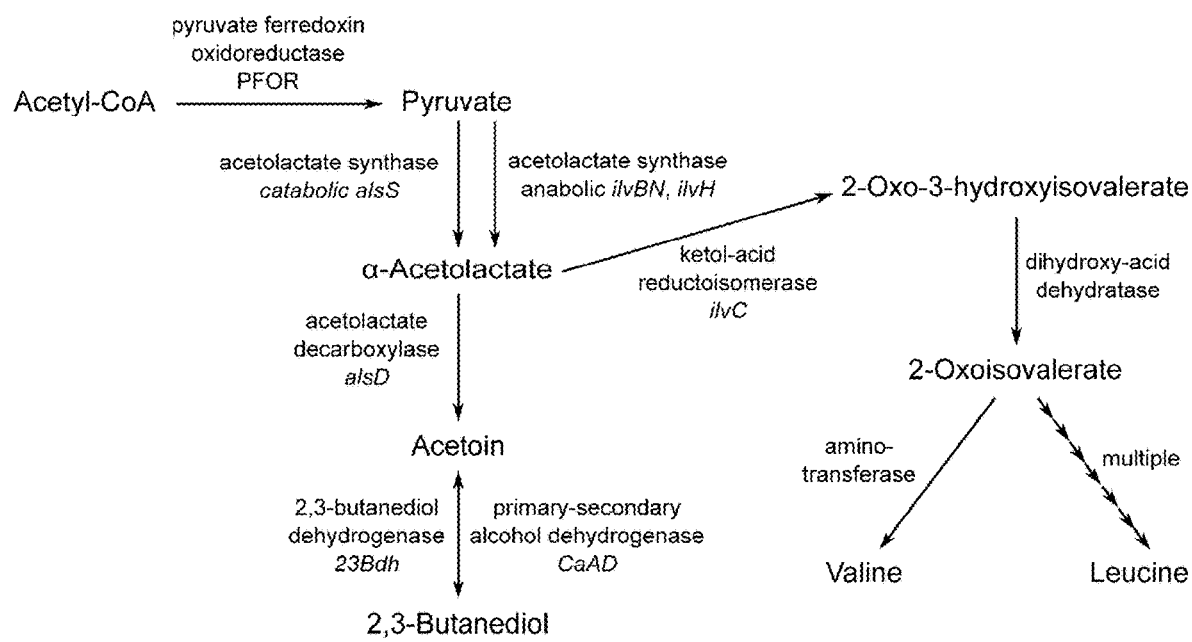
FIG. 3 is a diagram showing the 2,3-butanediol pathway and the associated branched-chain amino acid biosynthesis pathway. Pyruvate is converted to α-acetolactate, the intermediate for both the 2,3-butanediol and the branched-chain amino acid biosynthesis pathways. Experiments were performed to overexpress PFOR, alsS and alsD.
Figure 4:
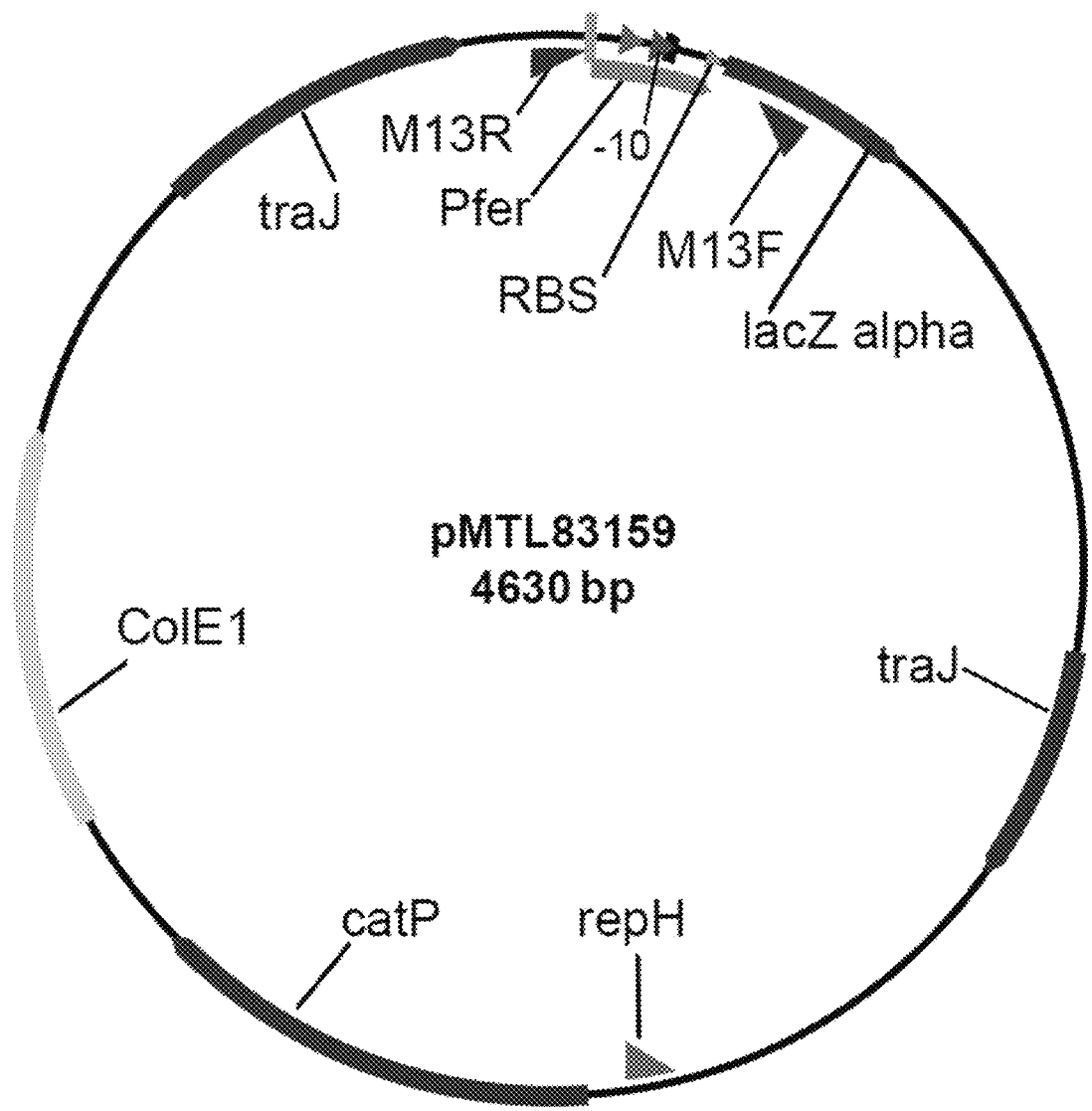
FIG. 4 is a schematic representation of the pMTL83159 plasmid. The plasmid contains a Gram negative origin of replication (ColE1) gene, a Gram positive origin of replication (repH) gene, the transfer gene traJ, the catP gene encoding for the chloramphenicol/thiamphenicol resistance, a multiple cloning site locating within lacZ alpha coding sequence and, a ferredoxin gene promoter ($P_{fdx}$).
Figure 5:
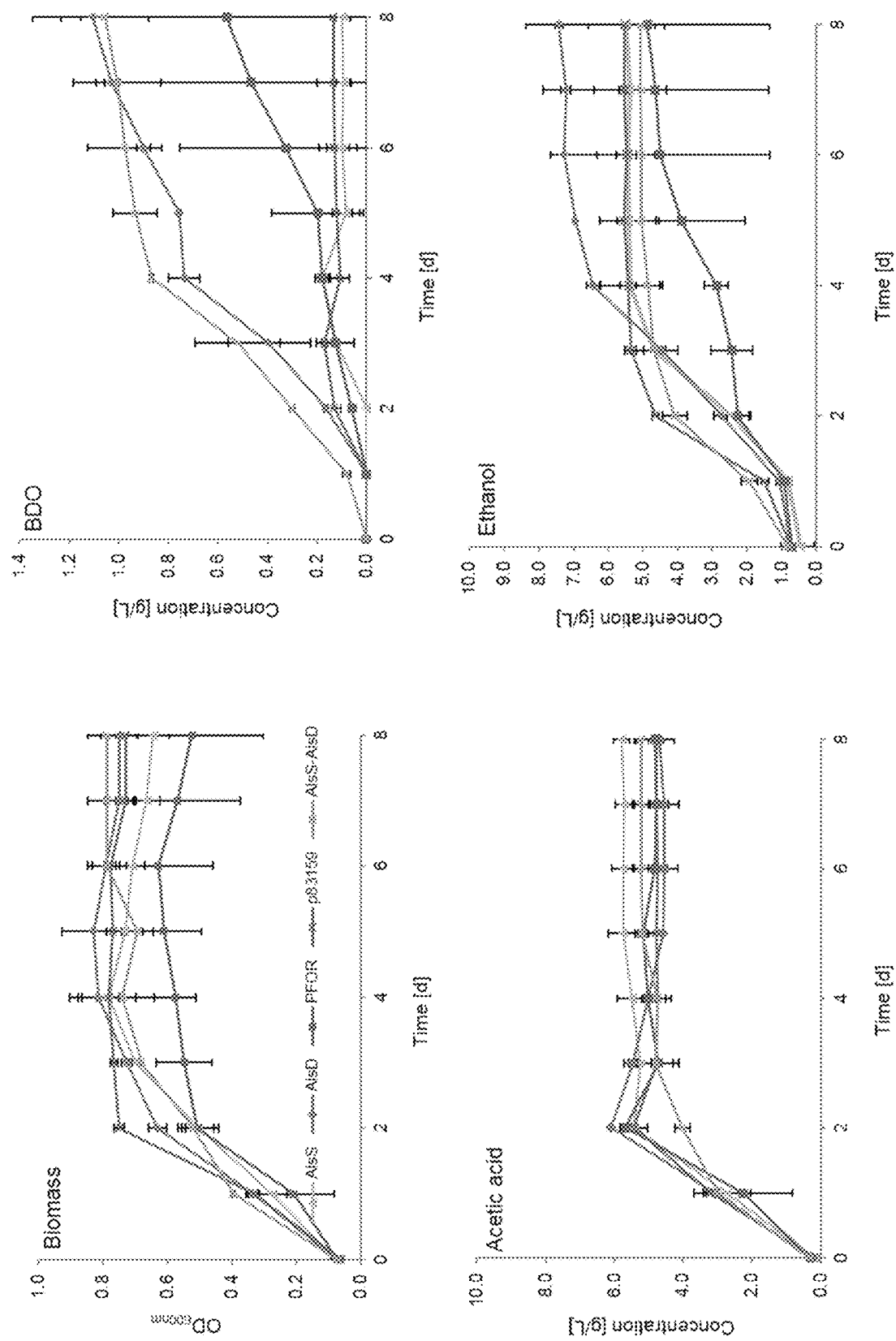
FIG. 5 is a set of graphs showing of the growth and metabolite profiles (biomass, 2,3-butanediol (BDO), acetic acid, and ethanol) versus time of five strains grown in Schott bottles.

As seen in FIG. 2, the bottleneck for 2,3-butanediol production is the reaction from acetyl CoA to pyruvate catalyzed by pyruvate:ferredoxin oxidoreductase. While all other measured reactions showed at least an activity of 1.1 U/mg, this rate limiting reaction exhibited an enzyme activity of only 0.11 U/mg (10%) in the presence of ferredoxin. This is 90% less than all other reactions in the pathway. To go at least some way towards overcoming this bottleneck and increase the product yield from the fermentation, an endogenous pyruvate:ferredoxin oxidoreductase enzyme may be overexpressed or an exogenous pyruvate:ferredoxin oxidoreductase enzyme may be introduced and expressed.

Example 4

This example demonstrates increasing the flux through the 2,3-butanediol production pathway by removing bottlenecks.

The reaction catalysing the conversion of acetyl-CoA to pyruvate has been identified in FIG. 2 to be the rate limiting step in 2,3-butanediol formation in *C. autoethanogenum, C. ljungdahlii,* or *C. ragsdalei.* This can be overcome by overexpressing the gene that encodes pyruvate:ferredoxin oxidoreductase in *C. autoethanogenum.*

The gene is codon-optimized to minimize issues with expression and designed to reduce homology to the native gene to prevent undesired integration events. The gene is flanked by restriction enzyme cut sites, XbaI (3'-end) and NheI (5'-end) for subcloning into pMTL83155. The synthesized construct and pMTL83155 are digested with XbaI and NheI (Fermentas), and the PFOR gene is ligated into pMTL83155 with T4 DNA ligase (Fermentas). The ligation mix is used to transform *E. coli* TOP10 (Invitrogen, LifeTechnologies) and colonies containing the desired plasmid are identified by plasmid miniprep (Zymo Research) and restriction digestion (Fermentas). The desired plasmid is methylated and transformed in *C. autoethanogenum.* Successful transformants are identified by thiamphenicol resistance and PCR analysis with primers repHF and CatR which will yield a 1584 base pair product when the plasmid is present.

Transformants identified as containing the desired plasmid are grown in serum bottles containing PETC-MES media in the presence of mill gas, and their metabolite production, measured by HPLC analysis, is compared to that of a parental microorganism not harbouring the plasmid. The pyruvate:ferredoxin oxidoreductase activity in the transformed strain is also measured in crude extracts to confirm that the observed bottleneck in the parental strain is alleviated. Overexpression of pyruvate:ferredoxin oxidoreductase increases the overall activity within the cell, alleviating the bottleneck in the pathway, and leading to an increase in the flux through pyruvate, and an increase in 2,3-butanediol production.

Example 5

This example demonstrates an increase in flux from pyruvate to 2-hydroxy-2-methyl-3-ketobutyrate (acetolactate) via overexpression of native catabolic acetolactate synthase.

The native catabolic acetolactate synthase gene (alsS) of *C. autoethanogenum* is cloned into the NdeI and NheI sites of pMTL83155 (WO 2013/185123) to generate an overexpression plasmid, expressing alsS under the control of the promoter region of the phosphotransacetylase-acetate kinase operon.

The overexpression plasmid can be similarly produced using a catabolic acetolactate synthase from another microorganism, a native anabolic acetolactate synthase, or an anabolic acetolactate synthase from another microorganism.

The use of either a catabolic acetolactate synthase from another microorganism or an anabolic acetolactate synthase from another microorganism may have a higher affinity toward pyruvate and faster reaction kinetics. An anabolic acetolactate synthase from another microorganism may be an enzyme which is identified to be insensitive to feedback inhibition. The small subunit of the anabolic acetolactate synthase mutant which is insensitive to feedback inhibitions may also be overexpressed.

The overexpression plasmid is introduced into *C. autoethanogenum.* This results in a *C. autoethanogenum* strain adapted to increase flux from pyruvate to acetolactate.

Example 6

This example describes a metabolic engineering approach to overexpression of pyruvate:ferredoxin oxidoreductase, acetolactate synthase, and/or acetolactate decarboxylase.

In order to boost 2,3-butanediol production, the pool of pyruvate, a precursor molecule of 2,3-butanediol, was increased. The first target was the PFOR gene which encodes the PFOR enzyme, which catalyzes the conversion of acetyl-CoA to pyruvate. In the *C. autoethanogenum* genome, there are two copies of the PFOR gene. It is known that the PFOR gene (CAETHG 0928) is constitutively expressed at a high level while the other gene (CAETHG 3029) is only up-regulated at the end of the growth in a batch culture (Köpke, *Appl Environ Microbiol,* 77: 5467-5475, 2011). Thus, the highly expressed PFOR gene was chosen to be overexpressed.

Acetolactate synthase, which links two pyruvate molecules to form α-acetolactate, is proposed to exist in three forms coded by three different genes in *C. autoethanogenum* and in closely related microorganisms (Köpke, *PNAS USA,* 107: 13087-13092, 2010; Köpke, *Appl Environ Microbiol,* 77: 5467-5475, 2011): one catabolic acetolactate synthase and two forms of anabolic acetolactate synthase. The alsS gene (CAETHG 1740) is predicted to code for the catabolic acetolactate synthase and to be involved in the formation of 2,3-butanediol. The two genes ilvBN (CAETHG 0406) and ilvH (CAETHG 0124) are predicted to code for anabolic acetolactate synthases which are likely to be involved in the formation of branched chain amino acids.

α-acetolactate is decarboxylated to acetoin via the activity of acetolactate decarboxylase encoded by the alsD gene (CAETHG 2932). In other microorganisms, the alsD gene transcript levels and the enzyme activity have been found to be regulated by the concentration of branched-chain amino acids present in the cell. It is still unknown if the branched-chain amino acids in *C. autoethanogenum* produce any feedback inhibition of the alsD gene transcription or the activity of the corresponding enzyme.

The reduction step from acetoin to 2,3-butanediol by the action of 2,3-butanediol dehydrogenase (EC 1.1.1.4) is not a rate limiting step. This has been demonstrated in batch and continuous cultures of *C. autoethanogenum* by the addition of acetoin to the fermentation media. In batch cultures, up to 40 g/L of acetoin was added and quantitatively converted to 2,3-butanediol after 24 hours of incubation. In fact, the putative 2,3-butanediol dehydrogenase gene was found to be expressed constitutively during both growth and stationary phase in a batch culture (Köpke, *Appl Environ Microbiol,* 77: 5467-5475, 2011). Furthermore, it has been shown that *C. autoethanogenum* contains a strictly NADPH-dependent primary-secondary alcohol dehydrogenase which also reduces acetoin and other ketones to 2,3-butanediol and other secondary alcohols (Köpke, *Catalyst Rev,* 27: 7-12, 2014).

The three native genes, PFOR, alsS, and alsD, were overexpressed individually and in combination of alsS-alsD and in combination of all three genes. To introduce the genes into *C. autoethanogenum,* the genes were cloned into a recombinant plasmid that carried an antibiotic resistant gene as a selection marker. For this reason, the control strain for this set of experiments carried the plasmid with the antibiotic resistance gene but without any active 2,3-butanediol gene insertion, so it could be exposed to antibiotic stress and compared to the performance of the overexpression strains. An important aspect of overexpression is the promoter choice to regulate the expression of inserted genes. In this research, the ferredoxin gene promoter ($P_{fdx}$) was chosen as it is known to be one of the strongest promoters in *Clostridia*. Furthermore, to avoid homologous recombination between the native gene in the genome and the gene present in the plasmid, the DNA sequence of the added genes was altered according to a proprietary optimizing process (GeneOptimizer) of the DNA synthesizing company (GeneArt).

Four heterologous genes were also targeted. A PFOR gene isolated from *Desulfovibrio africanus* has been shown to produce a PFOR enzyme that is highly stable in the presence of oxygen which could be advantageous in commercial anaerobe fermentation (Pieulle, *J Bacteriol*, 179: 5684-5692, 1997). The alsS gene isolated from *Bacillus substilis* and two heterologous alsD genes isolated from *Leuconostoc lactis* and from *Aeromonas hydrophila* were also tested. The alsS gene isolated from *Bacillus substilis* was used to construct the 2,3-butanediol pathway in a number of heterologous hosts (Ng, *Microb Cell Factories*, 11: 68, 2012; Oliver, *PNAS*, 110: 1249-1254, 2013). The alsD isolated from *Aeromonas hydrophila* was shown to have highest enzyme activity among several other heterogolous alsD isolated from other microorganisms in a recent study (Oliver, *PNAS*, 110: 1249-1254, 2013). These properties make these genes the ideal candidates for genetic manipulation experiments.

Example 7

This example describes cloning, conjugation, and characterization of strains overexpressing pyruvate:ferredoxin oxidoreductase, acetolactate synthase, and/or acetolactate decarboxylase.

*C. autoethanogenum* strain LZ1561 (DSM23693) was used in this research. Two *E. coli* donor strains were used as tools for genetic manipulation; the TOP 10 (Invitrogen) strain was used for plasmid cloning and the CA434 strain was used for conjugation with *C. autoethanogenum*.

A *Clostridium-E. coli* shuttle plasmid series pMTL83159 (4600 base pairs) was chosen to overexpress PFOR, alsS, and alsD genes (Heap, *J Microbiol Meth*, 78: 79-85, 2009). The plasmid was designed to contain a Gram-positive replicon, a Gram negative replicon, a traJ gene, an antibiotic resistant gene, the multiple cloning sites located within the lacZ alpha coding sequence, and the ferredoxin gene promoter ($P_{fdx}$). The Gram-positive replicon (repH gene) originated from the *C. butylicum* pCB102 plasmid. To clone the plasmid in *E. coli* the Gram-negative replicon ColE1 was chosen due to the high copy number of plasmids it produces. A traJ or transfer gene allows the genetic material to be transferred between donor and recipient cell. The catP gene encoded for the chloramphenicol/thiamphenicol resistance was the selection marker.

The three genes, PFOR, alsS, and alsD, were synthesized by a DNA synthesizing company (GeneArt). To clone them into the pMTL83159 plasmid, a pair of restriction enzyme recognition sequences and a ribosomal binding site sequence were added to each gene sequence and synthesized together with the gene. The original plasmids carrying the gene were first transformed into the *E. coli* TOP 10 strain. A ZYPPY™ plasmid miniprep kit (Zymo Research) was used to extract the plasmids. To transfer the targeted gene from its original plasmid to a pMTL83159 plasmid, both plasmids were cut with the same pair of restriction enzymes. The digested DNA was separated by gel electrophoresis on a 0.6% agarose gel which ran at 75 volts for one hour. After the plasmid pMTL83159 (vector) and the DNA sequence (insert) of each gene were recovered from the gel, they were ligated together by using T4 DNA ligase (Invitrogen). The ligated plasmids were then transformed into the *E. coli* Top 10 culture. To ensure sure that the extracted plasmids contained the insert, 1 μL of the plasmid was digested with appropriate restriction enzymes and the digested plasmid was then separated by gel electrophoresis on a 0.8% agarose gel.

The plasmids were transformed into *E. coli* CA434 donor cells and then conjugated with *C. autoethanogenum*. To confirm the presence of the targeted plasmid in the *C. autoethanogenum* transformants, PCR was performed using samples taken from the cultures in serum bottles.

The initial characterization of all the gene overexpression and gene disruption strains were first performed in 1 L-Schott bottles to screen which strain had produced the highest concentration of 2,3-butanediol. These strains were then further tested in CSTR continuous cultures, which allows for accurate control of fermentation parameters such that metabolite and biomass selectivities can be calculated.

The goals of the overexpression experiments were to overexpress three native genes in the 2,3-butanediol pathway individually and in combinations of two and three genes.

| Overexpression strain | Strain availability | Schott bottle data availability |
|---|---|---|
| Plasmid control | + | + |
| Native PFOR | + | + |
| Native AlsS | + | + |
| Native AlsD | + | + |
| Native AlsS-AlsD | + | + |
| Native PFOR-AlsS-AlsD | + | − |

In Schott bottle experiments, the OD, metabolite concentrations in the media, pH of the media and headspace pressure were monitored over the course of eight days by analyzing daily samples. At that point no further growth or significant metabolic activity was observed, the pH of all the cultures had dropped to between 3.8 and 4, and no further gas consumption was measured. A graphic representation of the growth and metabolite profiles versus time of the five strains are shown in FIG. 5. All five strains with Schott bottle data availability quickly grew during the first two days of incubation. Thereafter, the growth rate reduced significantly and then ceased on day 4. The maximum optical density values were approximately 0.75. Similarly to the biomass, the acetic acid concentrations increased steeply during the first two days in all the cultures. Between day 3 and day 4, the plasmid control and the alsS overexpression strains appeared to have stopped all metabolic activities, as no further changes in metabolite concentrations were observed. The other three strains showed activity until end of the experiments.

Conversion of acetate to ethanol (AOR activity) could still be observed in three strains after the growth slowed down. The most notable drop in acetate was observed in the alsD overexpression strain, and as a result, the highest ethanol concentration of around 7 g/L was reached by this strain. Two strains, the alsD and the combined alsS-alsD overexpression strains, produced higher amounts of 2,3-butanediol than the other strains, producing most of it during the active growth phase. Thereafter, during the stationary phase from day 4 they continued producing 2,3-butanediol at slower rates until the end of the experiment on day 8. The PFOR overexpression strain was the other strain that produced 2,3-butanediol to a higher concentration than the plasmid control strain. In contrast to the first two strains, the PFOR overexpression strain started producing most of the 2,3-butanediol during the onset of the stationary phase. The production rate was similar to the rates of the other two strains during the stationary phase.

Overexpression of the alsS gene alone did not appear to increase the amount of 2,3-butanediol. These results suggest that the 2,3-butanediol increase observed is primarily associated with the overexpression of the alsD gene. Overexpressing both alsS and alsD genes resulted in a slightly higher 2,3-butanediol concentration than just overexpressing the alsD gene alone. A positive additional effect of the alsS might be feasible. Overexpression of the PFOR gene appeared to have contributed to a higher 2,3-butanediol production during the stationary phase where no more growth was observed. Because of all of these positive results and the fact that no detrimental effect had been observed in these strains, the overexpression strain carrying all three gene was further tested in the continuous culture in CSTR.

To explore the full potential of the microbe using a CO-containing gaseous substrate, the overexpression strain carrying all three native genes and the plasmid control strain were further characterized in CSTR-based continuous cultures. The media pH was controlled during the entire fermentation by adding a base (5 M $NH_4OH$-solution) to compensate for the acid production and replenish media nitrogen levels. The substrate was continuously supplied by sparging a CO-containing gas mix through the stirred fermentation broth. The gas composition of the fresh incoming gas and the used outflowing gas was monitored hourly by gas chromatography. Based on the differences in gas composition between the inflowing and outflowing gases, the flow rate of the incoming gas, and the liquid volume of the fermentation; the gas utilization and rate of product synthesis at the time of sampling were calculated. The values are expressed in mol/L/d.

The OD and metabolite concentrations were measured three times a day and the dilution rate and the specific growth rate were measured and calculated daily to determine the productivity of each metabolite. The product selectivity of each metabolite was calculated using the CO consumption, $CO_2$ production, and the metabolite productivity. CO uptake rates of 4 mol/L/d and 8 mol/L/d were established to determine whether the product selectivity is dependent on the volumetric productivity. At a CO uptake of 4 mol/L/d, the dilution rate of the system was maintained at 1 $d^{-1}$ and the specific growth rate at 0.5 $d^{-1}$. At higher CO uptake of 8 mol/L/d and correspondingly higher metabolite production rates the dilution rate of the culture was increased to 1.7 $d^{-1}$ to lower the metabolite concentrations to a similar range as in the 4 mol/L/d experiments. The specific growth rate was also increased to 0.75 $d^{-1}$.

Figure 6:
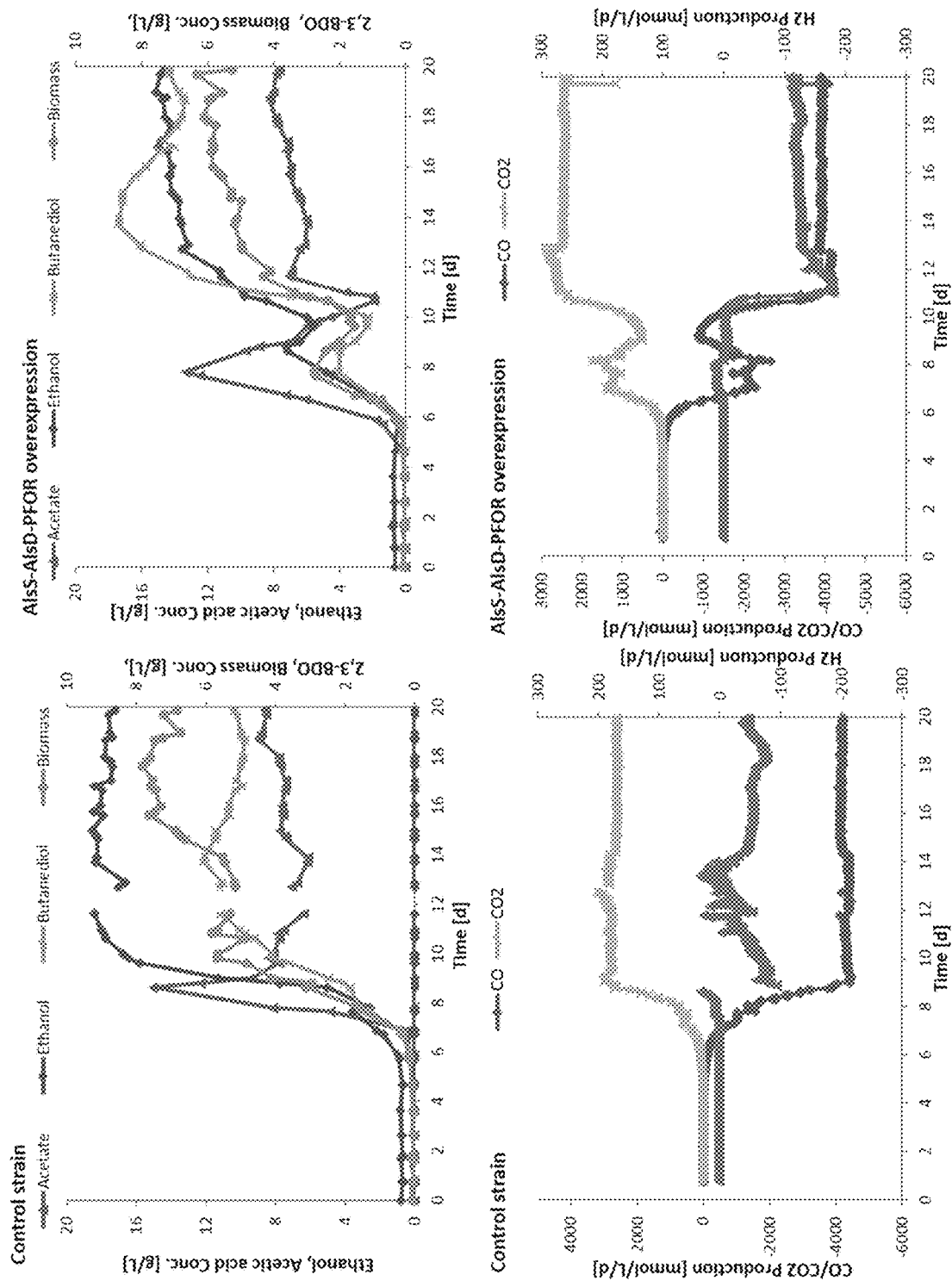
FIG. 6 is a set of graphs showing the metabolite profile (top graphs) and gas profile (bottom graphs) of the combined PFOR, alsS and alsD overexpression strain and the plasmid control strain at a 4 mol/L/d CO uptake over the course of 20 days.

The metabolite and gas profile of the combined PFOR, alsS, and alsD overexpression strain and the plasmid control strain was monitored at a 4 mol/L/d CO uptake over the course of 20 days (FIG. 6). Although the preparation of the inoculum of each strain went well through several rounds of serum bottle sub-culturing in regular intervals, the CSTR cultures exhibited an unusual, almost identical long lag phase of five days. At around day 5.5, both CSTR cultures started normal exponential growth (within hours of each other).

Despite the long lag phase in both cultures and the fluctuation in the growth pattern of the overexpression strain between days 8 and 10, both cultures were maintained at a stable gas uptake of 4 mol/L/d for 10 days. With a dilution rate of 1 $d^{-1}$ and a specific growth rate of 0.5 $d^{-1}$, it takes about six days to replace 95% of the bacterial load in the fermenters. With the constant gas uptake measured during this period, the latest values were used for analysis. The final results showed that the overexpression strain consistently produced higher 2,3-butanediol levels compared to the plasmid control strain.

Figure 7:
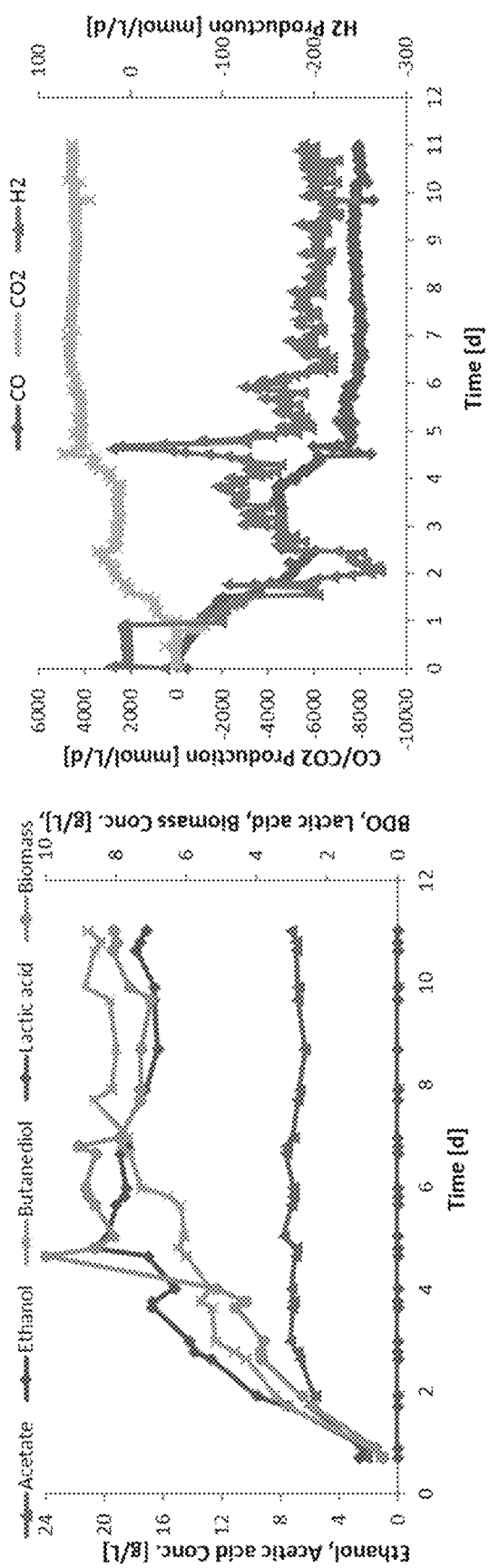
FIG. 7 is a set of graphs showing the metabolite and the gas profiles of the overexpression culture at an 8 mol/L/d CO uptake over the course of 11 days.

The metabolite and the gas profiles of the overexpression culture was monitored at an 8 mol/L/d CO uptake over the course of 11 days (FIG. 7). The culture was inoculated from the 4 mol/L/d CO uptake culture. No lag phase was observed in this culture, and an appropriate specific CO supply and dilution rate was applied during exponential growth to keep the culture under optimal growing conditions. Therefore a stable production of acetic acid was reached after day three of incubation while other metabolites continued to accumulate. The target of CO uptake was doubled from 4 mol/L/d to 8 mol/L/d.

To avoid product inhibition, the overall dilution rate of the culture was increased from 1 $d^{-1}$ to 1.7 $d^{-1}$ and the specific growth rate was increased proportionally. Metabolite concentrations slowly increased and reached a stable production rate after seven days. Both the hydrogen uptake and the CO uptake were maintained in a stable manner for six days, indicating that the fermentation of the overexpression strain has the potential to be operated stably for extended time periods.

Among the liquid products, ethanol was produced at the highest rate followed by acetate. The specific CO supply strategy was aimed to maintain a certain ratio of acetate to ethanol that allows the fermentation to be operated stably for extended periods of time. The LZ1561 strain and the plasmid control exhibited similar 2,3-butanediol and biomass profiles. The 2,3-butanediol to biomass production rate ratios were between 1.26 to 1.47 in these cultures. However, in the overexpression strain, this ratio was 2.45 at 4 mol/L/d CO uptake and 2.24 at the 8 mol/L/d CO uptake culture.

| Strain | LZ1561 | Control | Over-expression | LZ1561 | Over-expression |
|---|---|---|---|---|---|
| | Gas uptake rate (mol/L/d) | | | | |
| CO consumption | 4 | 4 | 4 | 8 | 8 |
| $CO_2$ production | 2.45 | 2.53 | 2.43 | 4.53 | 4.34 |
| Product | Production rate ($10^{-3}$ mol/L/d) | | | | |
| 2,3-Butanediol | 59 | 57 | 81 | 122 | 168 |
| Biomass | 37 | 44 | 33 | 83 | 75 |
| Ethanol | 447 | 450 | 367 | 798 | 823 |
| Acetic acid | 128 | 133 | 125 | 258 | 214 |

The product selectivity for 2,3-butanediol, biomass, ethanol and acetate for the overexpression, control and LZ1561 strains was measured at a gas uptake of 4 mol/L/d and 8 mol/L/d. With the optimized fermentation parameters, more than 50% of the carbon was directed to ethanol formation. The data shows that 2,3-butanediol selectivity of the overexpression strain increased from an average of 15% in the LZ1561 and the plasmid control cultures to 22.5%. The elevated 2,3-butanediol selectivity of the overexpression strain appeared to be maintained at different CO uptake rates. The increase in 2,3-butanediol selectivity is contributed to the decrease of ethanol selectivity at 4 mol/L/d or the decrease in the acetate selectivity at 8 mol/L/d. The exact contribution of ethanol and acetate cannot be separated, because their selectivity can be influenced easily by the specific gas supplies, which in turn are easily influenced by small differences between run parameters. For instance, pH, impeller position, probe location among others, can all affect these results.

Example 8

This example demonstrates expression of exogenous acetolactate decarboxylase to increase flux toward 2,3-butanediol.

Acetolactate decarboxylase genes from *A. hydrophila* and *L. lactis* were synthesized with codons selected for expression in *C. autoethanogenum* (GeneArt) and cloned into pMTL83159 as described above. The resulting plasmids, and pMTL83159 as a control, were transformed into *C. autoethanogenum* strain LZ1561 as described above.

Strains were grown in 1-L Schott bottles containing 40 mL of PETC-MES medium with no yeast extract and the headspace was replaced with 1.5 bar(gauge) synthetic mill gas (50% CO, 29% $N_2$, 18% $CO_2$, and 3% $H_2$) as the carbon and energy source. To maintain the plasmid, 15 mg $L^{-1}$ thiamphenicol was added. Biomass and metabolite concentrations were recorded through the growth of the cultures.

Figure 8:
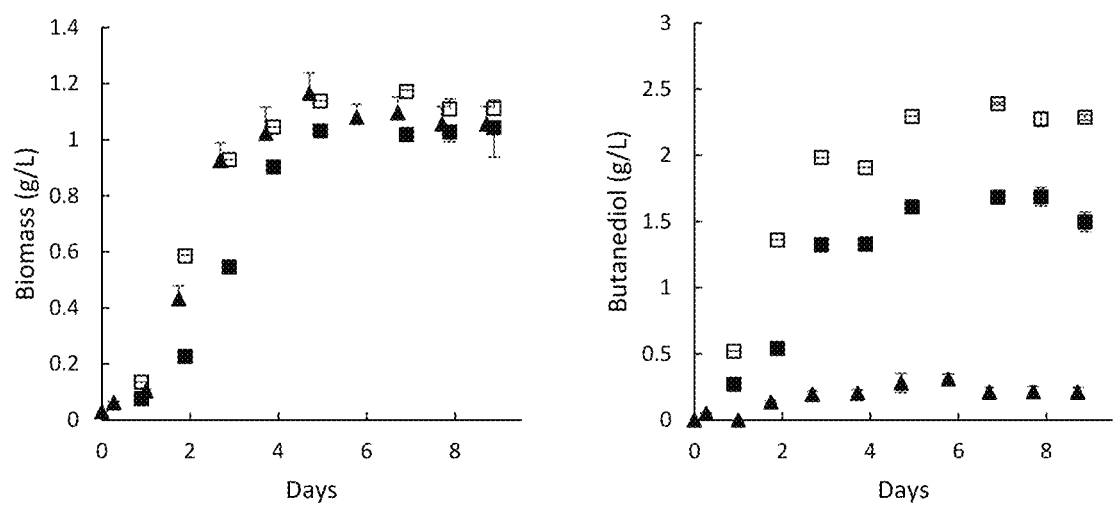
FIG. 8 is a set of graphs showing biomass and butanediol production of cultures expressing *A. hydrophila* alsD (open squares), *L. lactis* alsD (closed squares), and empty plasmid control (triangles). Values are the average of three replicates and error bars represent one standard deviation.

Expression of either exogenous acetolactate decarboxylase led to an increase of 2,3-butanediol production during growth on synthetic mill gas as compared to the strain harboring the empty plasmid as a control. Expression of alsD from *A. hydrophila* and *L. lactis* led to production of 2.3±0.08 and 1.6±0.16 g $L^{-1}$ 2,3-butanediol, respectively, compared to a production of 0.3±0.12 g $L^{-1}$ by the empty-plasmid-control-strain (FIG. 8).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A recombinant bacterium comprising a pyruvate:ferredoxin oxidoreductase (EC 1.2.7.1), an acetolactate synthase (EC 2.2.1.6), and an acetolactate decarboxylase (EC 4.1.1.5), wherein each enzyme is an overexpressed endogenous enzyme or an exogenous enzyme, wherein the bacterium is derived from *Clostridium autoethanogenum*, *Clostridium ljungdahlii*, or *Clostridium ragsdalei*, and wherein the bacterium produces 2,3-butanediol and acetate.

2. The bacterium of claim 1, wherein the pyruvate:ferredoxin is an overexpressed endogenous pyruvate:ferredoxin oxidoreductase.

3. The bacterium of claim 1, wherein the pyruvate:ferredoxin oxidoreductase is *Desulfovibrio africanus* pyruvate:ferredoxin oxidoreductase.

4. The bacterium of claim 1, wherein the acetolactate synthase is an overexpressed endogenous IlvB acetolactate synthase, an overexpressed endogenous IlvN acetolactate synthase, or an overexpressed endogenous AlsS acetolactate synthase.

5. The bacterium of claim 1, wherein the acetolactate synthase is a feedback-insensitive IlvN acetolactate synthase.

6. The bacterium of claim 1, wherein the acetolactate synthase is an exogenous *Bacillus subtilis* acetolactate synthase.

7. The bacterium of claim 1, wherein the acetolactate decarboxylase is an overexpressed endogenous AlsD acetolactate decarboxylase or an overexpressed endogenous BudA acetolactate decarboxylase.

8. The bacterium of claim 1, wherein the acetolactate decarboxylase is an exogenous *Aeromonas hydrophila* acetolactate decarboxylase.

9. The bacterium of claim 1, wherein the acetolactate decarboxylase is an exogenous *Leuconostoc lactis* acetolactate decarboxylase.

10. The bacterium of claim 1, wherein the bacterium is derived from *Clostridium autoethanogenum*.

11. The bacterium of claim 1, wherein the bacterium is derived from *Clostridium autoethanogenum* deposited under DSMZ Accession No. DSM23693.

12. The bacterium of claim 1, wherein the bacterium does not comprise an overexpressed endogenous or an exogenous 2,3-butanediol dehydrogenase (EC 1.1.1.4) enzyme.

13. The bacterium of claim 1, wherein the bacterium produces higher amounts of 2,3-butanediol than a bacterium that does not comprise the overexpressed endogenous or the exogenous pyruvate:ferredoxin oxidoreductase, acetolactate synthase, and acetolactate decarboxylase.

14. The bacterium of claim 1, wherein the bacterium produces 2,3-butanediol at a rate greater than 57 mmol/L/day.

15. The bacterium of claim 1, wherein the bacterium produces 2,3-butanediol at a rate greater than 122 mmol/L/day.

16. A method of producing 2,3-butanediol, comprising fermenting the bacterium of claim 1 in the presence of a gaseous substrate comprising CO to produce 2,3-butanediol.

* * * * *